US012606633B2

(12) United States Patent
Jiang et al.

(10) Patent No.: US 12,606,633 B2
(45) Date of Patent: Apr. 21, 2026

(54) METHODS AND COMPOSITIONS FOR ANTI-CD73 ANTIBODIES AND VARIANTS

(71) Applicants: SHANGHAI HENLIUS BIOTECH, INC., Shanghai (CN); SHANGHAI HENLIUS BIOPHARMACEUTICAL CO., LTD., Shanghai (CN); SHANGHAI HENLIUS BIOLOGICS CO., LTD., Shanghai (CN)

(72) Inventors: Wei-Dong Jiang, Shanghai (CN); I-yin Chen, Shanghai (CN); Chi-Ling Tseng, Shanghai (CN)

(73) Assignees: SHANGHAI HENLIUS BIOTECH, INC., Shanghai (CN); SHANGHAI HENLIUS BIOPHARMACEUTICAL CO., LTD., Shanghai (CN); SHANGHAI HENLIUS BIOLOGICS CO., LTD., Shanghai (CN)

( * ) Notice: Subject to any disclaimer, the term of this patent is extended or adjusted under 35 U.S.C. 154(b) by 1082 days.

(21) Appl. No.: 17/584,258

(22) Filed: Jan. 25, 2022

(65) Prior Publication Data

US 2022/0162334 A1    May 26, 2022

Related U.S. Application Data

(63) Continuation of application No. PCT/CN2020/102678, filed on Jul. 17, 2020.

(30) Foreign Application Priority Data

Jul. 26, 2019    (CN) .......................... 201910683287.5

(51) Int. Cl.
| | |
|---|---|
| *C07K 16/28* | (2006.01) |
| *A61K 39/00* | (2006.01) |
| *A61K 39/395* | (2006.01) |
| *A61K 45/06* | (2006.01) |
| *A61K 47/68* | (2017.01) |
| *A61P 35/00* | (2006.01) |
| *G01N 33/574* | (2006.01) |

(52) U.S. Cl.
CPC ...... *C07K 16/2896* (2013.01); *A61K 39/3955* (2013.01); *A61K 45/06* (2013.01); *A61K 47/6849* (2017.08); *A61P 35/00* (2018.01); *G01N 33/57492* (2013.01); *A61K 2039/505* (2013.01); *C07K 2317/31* (2013.01); *C07K 2317/33* (2013.01); *C07K 2317/565* (2013.01); *C07K 2317/77* (2013.01)

(58) Field of Classification Search
CPC ............ C07K 16/2896; C07K 2317/31; C07K 2317/33; C07K 2317/565; C07K 2317/77; C07K 2317/52; C07K 2317/55; C07K 2317/76; C07K 2317/92; C07K 16/40; C07K 2317/56; A61K 39/3955; A61K 45/06; A61K 47/6849; A61K 2039/505; A61P 35/00; G01N 33/57492
See application file for complete search history.

(56) References Cited

U.S. PATENT DOCUMENTS

| | | | |
|---|---|---|---|
| 11,479,600 B2 * | 10/2022 | Walker .................... A61P 31/14 |
| 2016/0129108 A1 | 5/2016 | Sachsenmeier et al. |
| 2016/0145350 A1 | 5/2016 | Lonberg et al. |
| 2017/0275362 A1 * | 9/2017 | Brentjens ......... C07K 14/70578 |
| 2018/0127513 A1 | 5/2018 | Lonberg et al. |

FOREIGN PATENT DOCUMENTS

| | | |
|---|---|---|
| CN | 107001474 A | 8/2017 |
| CN | 109154611 A | 1/2019 |
| CN | 109476740 A | 3/2019 |
| JP | 2017-537620 A | 12/2017 |
| JP | 2018-501197 A | 1/2018 |
| WO | WO 2016/075099 A1 | 5/2016 |
| WO | WO 2016/081748 A2 | 5/2016 |
| WO | WO 2016/131950 A1 | 8/2016 |
| WO | WO 2017/100670 A1 | 6/2017 |
| WO | WO 2017/152085 A1 | 9/2017 |
| WO | WO 2018/013611 A1 | 1/2018 |
| WO | WO 2018/110555 A1 | 6/2018 |
| WO | WO 2018/137598 A1 | 8/2018 |

(Continued)

OTHER PUBLICATIONS

Rudikoff et al Proc Natl Acad Sci USA 1982 vol. 79 p. 1979 (Year: 1982).*

(Continued)

*Primary Examiner* — Gregory S Emch
*Assistant Examiner* — Kathleen Cunningchen
(74) *Attorney, Agent, or Firm* — Finnegan, Henderson, Farabow, Garrett & Dunner, LLP

(57)    ABSTRACT

Provided are anti-CD73 antibodies, variants, and antigen binding fragments thereof. The antibodies, the variants, and the antigen binding fragments thereof bind to human CD73 with high affinity, and suppress the enzymatic activity of CD73, and optionally induce CD73 internalization. Further provided are isolated nucleic acid molecules encoding the anti-CD73 antibodies, the variants, and the antigen binding fragments thereof, and a related expression vector and a host cell. Provided is a method for preparing the anti-CD73 antibodies, the variants, and the antigen binding fragments thereof. Further provided are related pharmaceutical compositions and a method for using said pharmaceutical compositions in treating a subject.

17 Claims, 23 Drawing Sheets

Specification includes a Sequence Listing.

(56)          References Cited

FOREIGN PATENT DOCUMENTS

| WO | WO 2018/215535 A1 | 11/2018 |
| WO | WO 2018/237157 A1 | 12/2018 |
| WO | WO 2018/237173 A1 | 12/2018 |

OTHER PUBLICATIONS

Almagro et. al., Front. Immunol. 2018; 8:1751 (Year: 2018).*

Chiu ML et al. Antibodies 2019 8, 55, 1-80 (Year: 2019).*

International Search Report for International Application No. PCT/CN2020/102678 mailed Nov. 26, 2020 (9 pages).

Stagg, John et al., "Anti-CD73 Antibody Therapy Inhibits Breast Tumor Growth and Metastasis," Anti-CD73 Antibody Therapy Inhibits Breast Tumor Growth and Metastasis, Proceedings of the National Academy of Sciences, vol. 107, No. 4, Jan. 26, 2010, pp. 1547-1552.

Terp, Mikkel G et al., "Anti-Human CD73 Monoclonal Antibody Inhibits Metastasis Formation in Human Breast Cancer by Inducing Clustering and Internationalization of CD73 Expressed on the Surface of Cancer Cells," The Journal of Immunology, vol. 191, No. 8, Sep. 16, 2013, pp. 4165-4173.

Zheng, Q. et al., "A Novel Specific Anti-CD73 Antibody Inhibits Triple-Negative Breast Cancer Cell Motility by Regulating Autophagy," International Journal of Molecular Sciences, vol. 20, No. 5, Feb. 28, 2019, part 1057, pp. 1-15.

Sela-Culang et al., "The structural basis of antibody-antigen recognition," Frontiers in Immunology, vol. 4, No. 302, pp. 1-13 (2013).

Wirsdörfer, Florian et al., "Extracellular adenosine production by ecto-5'-nucleotidase (CD73) enhances radiation-induced lung fibrosis," Cancer Research, vol. 76, No. 10, pp. 3045-3056 (2016).

*Strahlenther Onkol*, vol. 19, pp. S14-S15 (2015) (184 pages).

* cited by examiner

Figure 1A

```
          1                                                  50
N1_LC   QT.VVTQEPS ASGTPGQRVT ISCSGSSSNI GS.NTVNWYQ QLPGTAPKLL
N2_LC   LNPMLTQPHS VSESPGKTVT ISCTCSGGRI ANNY.VQWYQ QRPGTSPTTV
N4_LC   .QAVLTQPSS VSGAPGQRVT ISCTGTSSNI GAGYDIHWYQ QLPGTAPKLL 51                                                 100
N1_LC   IYSNNQRPSG VPDRFSGS.. KSGISASLAI SGLQSEDEAD YYCAAWDDSL
N2_LC   IYEDNLRPSG VPDRFSGSID RASNSASLTI SDLRTEDEAH YYCQSYDSND
N4_LC   MYRFTRRPSG VPDRFSGS.. KSGTSASLTI TGLQVEDEAD YYCQSYDSGL 101                                                150
N1_LC   NGRVFGGGTK LTVLGQPKAA PSVTLFPPSS EELQANKATL VCLISDFYPG
N2_LC   GVA.FGGGTK LTVLGQPKAA PSVTLFPPSS EELQANKATL VCLISDFYPG
N4_LC   RGWVFGGGTK LAVLGQPKAA PSVTLFPPSS EELQANKATL VCLISDFYPG 151                                                200
N1_LC   AVTVAWKADS SPVKAGVETT TPSKQSNNKY AASSYLSLTP EQWKSHKSYS
N2_LC   AVTVAWKADS SPVKAGVETT TPSKQSNNKY AASSYLSLTP EQWKSHRSYS
N4_LC   AVTVAWKADS SPVKAGVETT TPSKQSNSKY AASSYLSLTP EQWKSHRSYS 201              220
N1_LC   CQVTHEGSTV EKTVALTECS
N2_LC   CQVTHGGSTV EKTVALTECS
N4_LC   CQVTHEGSTV EKTVALTECS
```

Figure 1B

```
          1                                                  50
N1_VH   EVQLVESGGG LVQPGRSLRL SCAASGFTFD DYAMHWVRQA PGKGLEWVSG
N2_VH   QVQLQQWGAG LLKPSETLSL TCAVYGGSFS GYYWSWIRQF PGKGLEWIGE
N4_VH   QVQLVQSGAE VKKSGSSVKV SCKASGGTFS SYAISWVRQA PGQGLEWMGG 51                                                100
N1_VH   ISWNSGSIGY ADSVRGRFTI SRDNAKNSLY LQMNSLRAED TALYYCAKDM
N2_VH   INH.SGSTNY NPSLKSRVTI SVDTSKNQFS LKLSSVTAAD TAVYYCAR.G
N4_VH   IIPIFGTANY AQKFQGRVTI TADESTSIAY MELSSLRSED TAVYYCASDG 101              125
N1_VH   GWELLKTYYY GMDVWGQGTT VTVSS
N2_VH   RYDFWSGYYA YFDYWGQGTL VTVSS
N4_VH   AVAAYD.... AFDIWGQGTM VTVSS
```

Figure 9

```
           1                                                                   50
    N1#2_VL   QTVVTQEPSA SGTPGQRVTI SCSGSSSNIG G.NTVNWYQQ LPGTAPKLLI
    N1#9_VL   QTVVTQEPSA SGTPGQRVTI SCSGSSSNIG S.NKVNWYQQ LPGTAPKLLI
    N4#1_VL   QAVLTQPSSV SGAPGQRVTI SCTGTSSNIG AGYDIHWYQQ LPGTAPKLLM
    N4#4_VL   QAVLTQPSSV SGAPGQRVTI SCTGTSSNIG AGYDIHWYQQ LPGTAPKLLM
  N4#4-3_VL   QAVLTQPSSV SGAPGQRVTI SCTGTSSNIG QGYDIHWYQQ LPGTAPKLLM
    N4#5_VL   QAVLTQPSSV SGAPGQRVTI SCTGTSSNIG AGYDIHWYQQ LPGTAPKLLM
    N4#6_VL   QAVLTQPSSV SGAPGQRVTI SCTGTSSNIG AGYDIHWYQQ LPGTAPKLLM
  N4#6-2_VL   QAVLTQPSSV SGAPGQRVTI SCTGTSSNIG HGYDIHWYQH LPGTAPKLLM
  N4#6-3_VL   QAVLTQPSSV SGAPGQRVTI SCTGTSSNIG LGYDIHWYQH LPGTAPKLLM
  N4#6-4_VL   QAVLTQPSSV SGAPGQRVTI SCTGTSSNIG AGFDIHWYQQ LPGTAPKLLM
  N4#6-5_VL   QAVLTQPSSV SGAPGQRVTI SCTGTSSNIG TGYDIHWYQQ LPGTAPKLLM 51                                                                 100
    N1#2_VL   YSNNQRPSGV PDRFSGSKSG ISASLAISGL QSEDEADYYC AAWDDSLNGR
    N1#9_VL   YSNNQRPSGV PDRFSGSKSG ISASLAISGL QSEDEADYYC AAWDISLNGR
    N4#1_VL   YRFTRRPSGV PDRFSGSKSG TSASLTITGL QVEDEADYYC QSYDSGLRGW
    N4#4_VL   YRFTRRPSGV PDRFSGSKSG TSASLTITGL QVEDEADYYC QSYDSGLRGW
  N4#4-3_VL   YRFTRRPSGV PDRFSGSKSG TSASLTITGL QVEDEADYYC QSYDSGLRGW
    N4#5_VL   YRFTRRPSGV PDRFSGSKSG TSASLTITGL QVEDEADYYC QSYDSGLRGL
    N4#6_VL   YRFTRRPSGV PDRFSGSKSG TSASLTITGL QVEDEADYYC QSYDSGQRGW
  N4#6-2_VL   YRFVRRPSGV PDRFSGSKSG TSASLTITGL QVEDEADYYC QSYDSGQRGW
  N4#6-3_VL   YRFDRRPSGV PDRFSGSKSG TSASLTITGL QVEDEADYYC QSYDSGQRGW
  N4#6-4_VL   YRFSRRPSGV PDRFSGSKSG TSASLTITGL QVEDEADYYC QSYDSGQRGW
  N4#6-5_VL   YRFTRRPSGV PDRFSGSKSG TSASLTITGL QVEDEADYYC QSYDSGQRGW 101        111
    N1#2_VL   VFGGGTKLTV L
    N1#9_VL   VFGGGTKLTV L
    N4#1_VL   YFGGGTKLTV L
    N4#4_VL   AFGGGTKLTV L
  N4#4-3_VL   AFGGGTKLTV L
    N4#5_VL   VFGGGTKLTV L
    N4#6_VL   VFGGGTKLTV L
  N4#6-2_VL   VFGGGTKLTV L
  N4#6-3_VL   VFGGGTKLTV L
  N4#6-4_VL   VFGGGTKLTV L
  N4#6-5_VL   VFGGGTKLTV L
```

Figure 10

```
         1                                                          50
  N1#2_VH   EVQLVESGGG LVQPGRSLRL SCAASGLTFD DYAMHWVRQA PGKGLEWVSG
  N1#9_VH   EVQLVESGGG LVQPGRSLRL SCAASGFTFD DYAMHWVRLA PGKGLEWVSG
  N4#1_VH   QVQLVQSGAE VKKSGSSVKV SCKASGYTFS SYAITWVRQA PGQGLEWMGG
  N4#4_VH   QVQLVQSGAE VKKSGSSVKV SCKASGGTFA SYAISWVRQA PGQGLEWMGG
N4#4-3_VH   QVQLVQSGAE VKKSGSSVKV SCKASGGTFA SYAISWVRQA PGQGLEWMGG
  N4#5_VH   QVQLVQSGAE VKKSGSSVKV SCKASGGTFS SYAIAWVRQA PGQGLEWMGG
  N4#6_VH   QVQLVQSGAE VKKSGSSVKV SCKASGGTFS SYAISWVRQA PGQGLEWMGG
N4#6-2_VH   QVQLVQSGAE VKKSGSSVKV SCKASGGTFS SYAISWVRQA PGQGLEWMGR
N4#6-3_VH   QVQLVQSGAE VKKSGSSVKV SCKASGGTFS SYAISWVRQA PGQGLEWMGG
N4#6-4_VH   QVQLVQSGAE VKKSGSSVKV SCKASGGTFS SYAISWVRQA PGQGLEWMGM
N4#6-5_VH   QVQLVQSGAE VKKSGSSVKV SCKASGGTFS SYAISWVRQA PGQGLEWMGR 51                                                        100
  N1#2_VH   ISWNSNSIGY ADPVRGRFTI SRDNAKNSLY LQMNSLRAED TALYYCAKDM
  N1#9_VH   ISWNSGSIGY ADSVRGRFTI SRDNAKNSLY LQMNSLRAED TALYYCAKDM
  N4#1_VH   IIPIFGTANY AQKFQGRVTI TADESTSIAY MELSSLRSED TAVYYCASDG
  N4#4_VH   IIPIFGTTNY AQKFQGRVTI TADESTSIAY MELSSLRSED TAVYYCASDG
N4#4-3_VH   IIPIFGTVNY AQKFQGRVTI TADESTSIAY MELSSLRSED TAVYYCASDG
  N4#5_VH   IIPIFGTVNY AQKFQGRVTI TADESTSIAY MELSSLRSED TAVYYCASDG
  N4#6_VH   IIPIFGTTNY AQKFQGRVTI TADESTSIAY MELSSLRSED TAVYYCASDG
N4#6-2_VH   IIPIFGTTNY AQKFQGRVTI TADESTSIAY MELSSLRSED TAVYYCASDG
N4#6-3_VH   IIPIFGTANY AQKFQGRVTI TADESTSIAY MELSSLRSED TAVYYCASDG
N4#6-4_VH   IIPIFGTANY AQKFQGRVTI TADESTSIAY MELSSLRSED TAVYYCASDG
N4#6-5_VH   IIPIFGTTNY AQKFQGRVTI TADESTSIAY MELSSLRSED TAMYYCASDG 101                         125
  N1#2_VH   GWELLKTSYY GMDVWGQGTT VTVSS
  N1#9_VH   GWSLLKTNYY GMDVWGQGTT VTVSS
  N4#1_VH   ....AVAAYD AFDIWGQGTM VTVSS
  N4#4_VH   ....AVAAYD AFDIWGQGTM VTVSS
N4#4-3_VH   ....AVAAYD AFDIWGQGTM VTVSS
  N4#5_VH   ....AVAAYD AFSIWGQGTM VTVSS
  N4#6_VH   ....AVAAYD AFLIWGQGTM VTVSS
N4#6-2_VH   ....AVAAYD AFLIWGQGTM VTVSS
N4#6-3_VH   ....AVAAYD AFLIWGQGTM VTVSS
N4#6-4_VH   ....AVAAYD AFLIWGQGTM VTVSS
N4#6-5_VH   ....AVAAYD AFLIWGQGTM VTVSS
```

Figure 14

```
           1                                                       50
N1#2-P_LC  QTVVTQEPSA SGTPGQRVTI SCSGSSSNIG G.NTVNWYQQ LPGTAPKLLI
N1#9-PH_LC QTVVTQEPSA SGTPGQRVTI SCSGSSSNIG S.NKVNWYQQ LPGTAPKLLI
N4#6-3-P_LC QAVLTQPSSV SGAPGQRVTI SCTGTSSNIG LGYDIHWYQQ LPGTAPKLLM
N4#6-4-P_LC QAVLTQPSSV SGAPGQRVTI SCTGTSSNIG AGFDIHWYQQ LPGTAPKLLM 51                                                      100
N1#2-P_LC  YSNNQRPSGV PDRFSGSKSG ISASLAISGL QSEDEADYYC AAWDDSLNGR
N1#9-PH_LC YSNNQRPSGV PDRFSGSKSG ISASLAISGL QSEDEADYYC AAWDISLNGR
N4#6-3-P_LC YRFDRRPSGV PDRFSGSKSG TSASLTITGL QVEDEADYYC QSYDSGQRGW
N4#6-4-P_LC YRFSRRPSGV PDRFSGSKSG TSASLTITGL QVEDEADYYC QSYDSGQRGW 101                                                     150
N1#2-P_LC  VFGGGTKLTV LGQPKAAPSV TLFPPSSEEL QANKATLVCL ISDFYPGAVT
N1#9-PH_LC VFGGGTKLTV LGQPKAAPSV TLFPPSSEEL QANKATLVCL ISDFYPGAVT
N4#6-3-P_LC VFGGGTKLTV LGQPKAAPSV TLFPPSSEEL QANKATLVCL ISDFYPGAVT
N4#6-4-P_LC VFGGGTKLTV LGQPKAAPSV TLFPPSSEEL QANKATLVCL ISDFYPGAVT 151                                                     200
N1#2-P_LC  VAWKADSSPV KAGVETTTPS KQSNNKYAAS SYLSLTPEQW KSHKSYSCQV
N1#9-PH_LC VAWKADSSPV KAGVETTTPS KQSNNKYAAS SYLSLTPEQW KSHKSYSCQV
N4#6-3-P_LC VAWKADSSPV KAGVETTTPS KQSNNKYAAS SYLSLTPEQW KSHKSYSCQV
N4#6-4-P_LC VAWKADSSPV KAGVETTTPS KQSNNKYAAS SYLSLTPEQW KSHKSYSCQV 201        217
N1#2-P_LC  THEGSTVEKT VAPTECS
N1#9-PH_LC THEGSTVEKT VAPTECS
N4#6-3-P_LC THEGSTVEKT VAPTECS
N4#6-4-P_LC THEGSTVEKT VAPTECS
```

Figure 15

```
           1                                                       50
N1#2-P_VH  EVQLVESGGG LVQPGRSLRL SCAASGFTFD DYAMHWVRQA PGKGLEWVSG
N1#9-PH_VH EVQLVESGGG LVQPGRSLRL SCAASGFTFD DYAMHWVRLA PGKGLEWVSG
N4#6-3-P_VH QVQLVQSGAE VKKSGSSVKV SCKASGGTFS SYAISWVRQA PGQGLEWMGG
N4#6-4-P_VH QVQLVQSGAE VKKSGSSVKV SCKASGGTFS SYAISWVRQA PGQGLEWMGM 51                                                      100
N1#2-P_VH  ISWNSNSIGY ADSVRGRFTI SRDNAKNSLY LQMNSLRAED TALYYCAKDM
N1#9-PH_VH ISWNSGSIGY ADSVRGRFTI SRDNAKNSLY LQMNSLRAED TALYYCAKDM
N4#6-3-P_VH IIPIFGTANY AQKFQGRVTI TADESTSIAY MELSSLRSED TAVYYCASDG
N4#6-4-P_VH IIPIFGTANY AQKFQGRVTI TADESTSIAY MELSSLRSED TAVYYCASDG 101        125
N1#2-P_VH  GWELLKTSYY GMDVWGQGTT VTVSS
N1#9-PH_VH GWSLLKTNYY GMDVWGQGTT VTVSS
N4#6-3-P_VH ....AVAAYD AFLIWGQGTM VTVSS
N4#6-4-P_VH ....AVAAYD AFLIWGQGTM VTVSS
```

METHODS AND COMPOSITIONS FOR ANTI-CD73 ANTIBODIES AND VARIANTS

This is a continuation of International Application No. PCT/CN2020/102678, filed Jul. 17, 2020, which claims priority to CN 201910683287.5, filed Jul. 26, 2019; all of which are incorporated herein by reference.

STATEMENT REGARDING SEQUENCE LISTING

The sequence listing associated with this application, which was submitted electronically as an ASCII text file with the filing of this application, is hereby incorporated by reference in its entirety. The ASCII text file is named 15080_0002-FPCH21160406US_SEQUENCE_LISTING. TXT, was created on Jan. 24, 2022, and is 105,427 bytes in size.

FIELD

The present disclosure relates generally to anti-CD73 antibodies, their variants or mutants, or antigen binding fragment thereof, and methods of use thereof, in the treatment of human cancers.

BACKGROUND

CD73, known as ecto-5'-nucleotidase (NT5E, EC 3.1.3.5) is a glycosyl-phosphatidylinositol (GPI)-linked 70-kDa cell surface enzyme found in most tissues (Zhang B., *Cancer Res.,* 70(16): 6407-6411, 2010). CD73, originally defined as a lymphocyte differentiation antigen, is thought to function as a co-signaling molecule on T lymphocytes, and as an adhesion molecule that is important for lymphocyte binding to endothelium. Recent studies have implicated CD73 in the control of a variety of physiologic responses, including epithelial ion and fluid transport, ischemic preconditioning, tissue injury, platelet function, hypoxia, and vascular leak (Zhang B., *Cancer Res.,* 70(16): 6407-6411 (2010)).

Immunosuppression effects of extracellular adenosine have been demonstrated (Stagg J. et al., *Oncogene,* 29(39): 5346-5358, 2010). Adenosine interacts with its receptors can suppress most immune cell functions, including Natural Killer (NK) cells cytotoxicity, macrophage phagocytosis, T cell cytotoxicity and cytokine release (Goto T. et al., *J. Immunol.,* 130(3): 1350-1355 (1983); Ohta A. et al., *J. Immunol.,* 183(9): 5487-5493 (2009)). Blockade of adenosine signaling can improve immunotherapies. CD73 is a key molecule involved in adenosine signaling. CD73 hydrolyzes adenosine monophosphate (AMP), a product from adenosine triphosphate (ATP) hydrolysis pathway by CD39, to adenosine to affect tumor microenvironment (Allard B. et al., *Immunol. Rev.,* 276(1): 121-144 (2017); Resta R. et al., *Immunol. Rev.,* 161:95-109 (1998)). The CD73-adenosine axis constitutes one of the most promising pathways in immuno-oncology.

Studies reported that CD73 participates in cell-cell and cell-matrix interactions and implicated CD73 in drug resistance and tumor promotion (Spychala J., *Pharmacol. Ther.,* 87(2-3): 161-173 (2000)). CD73 overexpression in several kinds of cancer cells have been confirmed (Gao Z W. et al., *Biomed. Res. Int.,* 2014:460654 (2014)) and the expression is correlated with poor prognosis or patient survival of some cancers (Loi S. et al., *Proc. Natl. Acad. Sci. USA,* 110(27): 11091-11096 (2013); Turcotte M. et al., *Cancer Res.,* 75(21): 4494-4503 (2015); Xiong L. et al., *Cell Tissue Res.,*

355(2): 365-374 (2014)). In some cases, anti-CD73 monoclonal antibodies (mAb) treatment can inhibit metastasis and tumor angiogenesis (Allard B. et al., *Int. J. Cancer,* 134 (6): 1466-1473 (2014); Terp M G. et al., *J. Immunol.,* 191(8): 4165-4173 (2013)). In addition, researchers have demonstrated the immunosuppressive role of CD73-adenosine in cancer and provided that the targeted blockade of CD73 or adenosine receptors could effectively promote anti-tumor immunity and enhance the activity of first-generation immune checkpoint blockers (Allard D. et al., *Immunotherapy,* 8(2): 145-163 (2016)).

Over recent years, targeting CD73 has resulted in favorable antitumor effects in preclinical models, and the combined treatment of CD73 blockade with other immune-modulating agents is a particularly attractive therapeutic option (Antonioli L. et al., *Trends Cancer,* 2(2): 95-109 (2016)). Combination with anti-CD73 mAb can significantly enhance the anti-tumor activity of anti-CTLA-4 (cytotoxic T lymphocyte antigen 4) mAb and anti-PD-1 (programmed cell death protein 1) mAb (Allard B. et al., *Clin. Cancer Res.,* 19(20): 5626-5635 (2013)).

However, despite advances in research directed to CD73 and utilization of this protein for clinical benefit, there remains a need for the development of effective, safe, and potent antibody agents directed against CD73. These needs and other needs are satisfied by the present disclosure.

SUMMARY

In accordance with the purpose(s) of the present disclosure, as embodied and broadly described herein, the disclosure, in one aspect, relates to anti-CD73 antibodies, variants, mutants, and/or antigen binding fragments thereof, methods of making same, pharmaceutical compositions comprising same, and methods of treating a human subject using same. For example, the disclosed anti-CD73 antibodies and their affinity variants and/or mutants or antigen binding fragments can be used alone or in combination with other agents in treating a disease associated with CD73 expression, CD73 overexpression, and/or abnormal CD73 function, such as a cancer or fibrosis. The antibodies provided herein can also be used for detecting CD73 protein in patients or patient samples by administering the anti-CD73 antibodies, and/or their affinity variants/mutants or antigen binding fragments thereof, to patients and detecting the anti-CD73 antibody, and/or variants/mutants, or antigen binding fragments thereof, bound to the CD73 protein in a sample from the patient (e.g., in vivo or ex vivo) or by contacting the anti-CD73 antibodies, and/or variants/mutants or antigen binding fragments thereof, with samples from patients and detecting qualitatively or quantitatively the anti-CD73 antibody, and/or affinity variant/mutant or antigen binding fragment thereof, bound to the CD73 protein.

Provided by the present disclosure are anti-CD73 antibodies and variants, and/or antigen binding fragments thereof. In certain embodiments, the present disclosure provides at least eighteen (18) anti-CD73 antibodies, variants, and/or antigen binding fragments thereof, namely, anti-CD73 antibodies, and/or variants N1 and its variants: N1 #2, N1 #2-P, N1 #9 and N1 #9-PH, variant N2, variants N4 and its variants: N4 #1, N4 #4, N4 #4-3, N4 #5, N4 #6, N4 #6-2, N4 #6-3, N4 #6-3-P, N4 #6-4, N4 #6-4-P and N4 #6-5. The nucleic acid and/or its encoding amino acid sequences of the light chain and heavy chain of each of these eighteen (18) anti-CD73 antibodies and/or variants thereof, are provided in the Sequence Listing below. The CDR sequences of each light chain (CDR-L1, CDR-L2, and CDR-L3) and each heavy chain (CDR-H1, CDR-H2, and CDR-H3) of each anti-CD73 antibody, and/or variant thereof, are provided in below Tables 1 and 2, respectively.

TABLE 1

Ant-CD73 Antibodies, Variants, and/or Mutants Light Chain CDR Sequences

| Anti-CD73 Designation | CDR-L1 | SEQ ID NO: | CDR-L2 | SEQ ID NO: | CDR-L3 | SEQ ID NO: |
|---|---|---|---|---|---|---|
| N1_LC | SGSSSNIGSNTVN | 1 | SNNQRPS | 11 | AAWDDSLNGRV | 17 |
| N2_LC | TCSGGRIANNYVQ | 2 | EDNLRPS | 12 | QSYDSNDGVA | 18 |
| N4_LC | TGTSSNIGAGYDIH | 3 | RFTRRPS | 13 | QSYDSGLRGWV | 19 |
| N1#2_VL | SGSSSNIGGNTVN | 4 | SNNQRPS | 11 | AAWDDSLNGRV | 17 |
| N1#9_VL | SGSSSNIGSNKVN | 5 | SNNQRPS | 11 | AAWDISLNGRV | 20 |
| N4#1_VL | TGTSSNIGAGYDIH | 3 | RFTRRPS | 13 | QSYDSGLRGWY | 21 |
| N4#4_VL | TGTSSNIGAGYDIH | 3 | RFTRRPS | 13 | QSYDSGLRGWA | 22 |
| N4#5_VL | TGTSSNIGAGYDIH | 3 | RFTRRPS | 13 | QSYDSGLRGLV | 23 |
| N4#6_VL | TGTSSNIGAGYDIH | 3 | RFTRRPS | 13 | QSYDSGQRGWV | 24 |
| N4#4-3_VL | TGTSSNIGQGYDIH | 6 | RFTRRPS | 13 | QSYDSGLRGWA | 22 |
| N4#6-2_VL | TGTSSNIGHGYDIH | 7 | RFVRRPS | 14 | QSYDSGQRGWV | 24 |
| N4#6-3_VL | TGTSSNIGLGYDIH | 8 | RFDRRPS | 15 | QSYDSGQRGWV | 24 |
| N4#6-4_VL | TGTSSNIGAGFDIH | 9 | RFSRRPS | 16 | QSYDSGQRGWV | 24 |
| N4#6-5_VL | TGTSSNIGTGYDIH | 10 | RFTRRPS | 13 | QSYDSGQRGWV | 24 |
| N1#2-P_LC | SGSSSNIGGNTVN | 4 | SNNQRPS | 11 | AAWDDSLNGRV | 17 |
| N1#9-PH_LC | SGSSSNIGSNKVN | 5 | SNNQRPS | 11 | AAWDISLNGRV | 20 |
| N4#6-3-P_LC | TGTSSNIGLGYDIH | 8 | RFDRRPS | 15 | QSYDSGQRGWV | 24 |
| N4#6-4-P_LC | TGTSSNIGAGFDIH | 9 | RFSRRPS | 16 | QSYDSGQRGWV | 24 |

TABLE 2

Ant-CD73 Antibodies, Variants, and/or Mutants Heavy Chain CDR Sequences

| Anti-CD73 Designation | CDR-H1 | SEQ ID NO: | CDR-H2 | SEQ ID NO: | CDR-H3 | SEQ ID NO: |
|---|---|---|---|---|---|---|
| N1_VH | DYAMH | 25 | GISWNSGSIGYADSVRG | 30 | DMGWELLKTYYYGMDV | 39 |
| N2_VH | GYYWS | 26 | EINHSGSTNYNPSLKS | 31 | GRYDFWSGYYAYFDY | 40 |
| N4_VH | SYAIS | 27 | GIIPIFGTANYAQKFQG | 32 | DGAVAAYDAFDI | 41 |
| N1#2_VH | DYAMH | 25 | GISWNSNSIGYADPVRG | 33 | DMGWELLKTSYYGMDV | 42 |
| N1#9_VH | DYAMH | 25 | GISWNSGSIGYADSVRG | 30 | DMGWSLLKTNYYGMDV | 43 |
| N4#1_VH | SYAIT | 28 | GIIPIFGTANYAQKFQG | 32 | DGAVAAYDAFDI | 41 |
| N4#4_VH | SYAIS | 27 | GIIPIFGTTNYAQKFQG | 34 | DGAVAAYDAFDI | 41 |
| N4#5_VH | SYAIA | 29 | GIIPIFGTVNYAQKFQG | 35 | DGAVAAYDAFSI | 44 |
| N4#6_VH | SYAIS | 27 | GIIPIFGTTNYAQKFQG | 34 | DGAVAAYDAFLI | 45 |
| N4#4-3_VH | SYAIS | 27 | GIIPIFGTVNYAQKFQG | 35 | DGAVAAYDAFDI | 41 |
| N4#6-2_VH | SYAIS | 27 | RIIPIFGTTNYAQKFQG | 36 | DGAVAAYDAFLI | 45 |

TABLE 2-continued

Ant-CD73 Antibodies, Variants, and/or Mutants Heavy Chain CDR Sequences

| Anti-CD73 Designation | CDR-H1 | SEQ ID NO: | CDR-H2 | SEQ ID NO: | CDR-H3 | SEQ ID NO: |
|---|---|---|---|---|---|---|
| N4#6-3_VH | SYAIS | 27 | GIIPIFGTANYAQKFQG | 32 | DGAVAAYDAFLI | 45 |
| N4#6-4_VH | SYAIS | 27 | MIIPIFGTANYAQKFQG | 37 | DGAVAAYDAFLI | 45 |
| N4#6-5_VH | SYAIS | 27 | RIIPIFGTTNYAQKFQG | 36 | DGAVAAYDAFLI | 45 |
| N1#2-P_VH | DYAMH | 25 | GISWNSNSIGYADSVRG | 38 | DMGWELLKTSYYGMDV | 42 |
| N1#9-PH_VH | DYAMH | 25 | GISWNSGSIGYADSVRG | 30 | DMGWSLLKTNYYGMDV | 43 |
| N4#6-3-P_VH | SYAIS | 27 | GIIPIFGTANYAQKFQG | 32 | DGAVAAYDAFLI | 45 |
| N4#6-4-P_VH | SYAIS | 27 | MIIPIFGTANYAQKFQG | 37 | DGAVAAYDAFLI | 45 |

In some embodiments, according to (or as applied to) any of the embodiments above, the anti-CD73 antibody of the present disclosure comprises one or more mutations at the N-glycosylation sites of its one or more CDRs in the variable domains. The resulting de-glycosylated antibody remains the equal function as the parent non-de-glycosylated antibody.

In some embodiments, according to (or as applied to) any of the embodiments above, the anti-CD73 antibody of the present disclosure is a full-length IgG antibody, wherein the light chain is composed of the above light chain variable region and human antibody light chain constant region, wherein the heavy chain is composed of the above heavy chain variable region and human antibody heavy chain constant region.

In some embodiments, according to (or as applied to) any of the embodiments above, the anti-CD73 antibody of the present disclosure is a full-length IgG antibody, wherein the light chain is composed of the above light chain variable region and human antibody light chain constant region, and the light chain constant region is as shown in SEQ ID NO. 115, wherein the heavy chain is composed of the above heavy chain variable region and human antibody heavy chain constant region, wherein the heavy chain constant region is as shown in 112, 113 or 114.

In some embodiments, according to (or as applied to) any of the embodiments above, the anti-CD73 antibody of the present disclosure is a full-length IgG antibody, wherein:

(antibody variant N1 #2-P) the light chain is as shown in SEQ ID NO. 93 and the heavy chain is as shown in SEQ ID NO. 116, or (antibody variant N1 #9-PH) the light chain is as shown in SEQ ID NO. 94 and the heavy chain is as shown in SEQ ID NO. 117, or (antibody variant N4 #6-3-P) the light chain is as shown in SEQ ID NO. 95 and the heavy chain is as shown in SEQ ID NO. 118, or (Antibody variant N4 #6-4-P) the light chain is as shown in SEQ ID NO. 96 and the heavy chain is as shown in SEQ ID NO. 119.

TABLE 3

The correspondence table of CDR, VH, VL, LC and HC sequence numbers of the antibodies

| CLM | clone | CDRL1 SEQ ID NO | CDRL2 SEQ ID NO | CDRL3 SEQ ID NO | CDRH1 SEQ ID NO | CDRH2 SEQ ID NO | CDRH3 SEQ ID NO | VL SEQ ID NO | VH SEQ ID NO | LC SEQ ID NO | HC SEQ ID NO |
|---|---|---|---|---|---|---|---|---|---|---|---|
| 1 | antibody N1 | 1 | 11 | 17 | 25 | 30 | 39 | | | | |
| 2 | antibody N1 | | | | | | | | 64 encoded 97 | 46 encoded 79 | |
| 3 | antibody N2 | 2 | 12 | 18 | 26 | 31 | 40 | | | | |
| 4 | antibody N2 | | | | | | | | 65 encoded 98 | 47 encoded 80 | |
| 5 | antibody N4 | 3 | 13 | 19 | 27 | 32 | 41 | | | | |
| 6 | antibody N4 | | | | | | | | 66 encoded 99 | 48 encoded 81 | |
| 7 | variant N1#2 | 4 | 11 | 17 | 25 | 33 | 42 | | | | |
| 8 | variant N1#2 | | | | | | | 49 encoded 82 | 67 encoded 100 | | |
| 9 | variant N1#9 | 5 | 11 | 20 | 25 | 30 | 43 | | | | |
| 10 | variant N1#9 | | | | | | | 50 encoded 83 | 68 encoded 101 | | |

TABLE 3-continued

The correspondence table of CDR, VH, VL, LC and HC sequence numbers of the antibodies

| CLM | | clone | CDRL1 SEQ ID NO | CDRL2 SEQ ID NO | CDRL3 SEQ ID NO | CDRH1 SEQ ID NO | CDRH2 SEQ ID NO | CDRH3 SEQ ID NO | VL SEQ ID NO | VH SEQ ID NO | LC SEQ ID NO | HC SEQ ID NO |
|---|---|---|---|---|---|---|---|---|---|---|---|---|
| 11 | variant | N4#1 | 3 | 13 | 21 | 28 | 32 | 41 | | | | |
| 12 | variant | N4#1 | | | | | | | 51 encoded 84 | 69 encoded 102 | | |
| 13 | variant | N4#4 | 3 | 13 | 22 | 27 | 34 | 41 | | | | |
| 14 | variant | N4#4 | | | | | | | 52 encoded 85 | 70 encoded 103 | | |
| 15 | variant | N4#5 | 3 | 13 | 23 | 29 | 35 | 44 | | | | |
| 16 | variant | N4#5 | | | | | | | 53 encoded 86 | 71 encoded 104 | | |
| 17 | variant | N4#6 | 3 | 13 | 24 | 27 | 34 | 45 | | | | |
| 18 | variant | N4#6 | | | | | | | 54 encoded 87 | 72 encoded 105 | | |
| 19 | variant | N4#4-3 | 6 | 13 | 22 | 27 | 35 | 41 | | | | |
| 20 | variant | N4#4-3 | | | | | | | 55 encoded 88 | 73 encoded 106 | | |
| 21 | variant | N4#6-2 | 7 | 14 | 24 | 27 | 36 | 45 | | | | |
| 22 | variant | N4#6-2 | | | | | | | 56 encoded 89 | 74 encoded 107 | | |
| 23 | variant | N4#6-3 | 8 | 15 | 24 | 27 | 32 | 45 | | | | |
| 24 | variant | N4#6-3 | | | | | | | 57 encoded 90 | 75 encoded 108 | | |
| 25 | variant | N4#6-4 | 9 | 16 | 24 | 27 | 37 | 45 | | | | |
| 26 | variant | N4#6-4 | | | | | | | 58 encoded 91 | 76 encoded 109 | | |
| 27 | variant | N4#6-5 | 10 | 13 | 24 | 27 | 36 | 45 | | | | |
| 28 | variant | N4#6-5 | | | | | | | 59 encoded 92 | 77 encoded 110 | | |
| 29 | variant | N1#2-P | 4 | 11 | 17 | 25 | 38 | 42 | | | | |
| 30 | variant | N1#2-P | | | | | | | | 78 encoded 111 | 60 encoded 93 | 116 |
| 31 | variant | N1#9-PH | 5 | 11 | 20 | 25 | 30 | 43 | | | | |
| 32 | variant | N1#9-PH | | | | | | | | 68 encoded 101 | 61 encoded 94 | 117 |
| 33 | variant | N4#6-3-P | 8 | 15 | 24 | 27 | 32 | 45 | | | | |
| 34 | variant | N4#6-3-P | | | | | | | | 75 encoded 108 | 62 encoded 95 | 118 |
| 35 | variant | N4#6-4-P | 9 | 16 | 24 | 27 | 37 | 45 | | | | |
| 36 | variant | N4#6-4-P | | | | | | | | 76 encoded 109 | 63 encoded 96 | 119 |

In some embodiments, according to (or as applied to) any of the embodiments above, the anti-CD73 antibody comprises an Fc sequence of a human IgG. In some embodiments, according to (or as applied to) any of the embodiments above, the antigen binding fragment is selected from the group consisting of a Fab, Fab', a F(ab')$_2$, a single-chain Fv (scFv), an Fv fragment, a diabody, and a linear antibody. In some embodiments, according to (or as applied to) any of the embodiments above, the antibody is a multispecific antibody.

In some embodiments, according to (or as applied to) any of the embodiments above, the anti-CD73 antibody, the variant or antigen binding fragment thereof, is conjugated to a therapeutic agent. In some embodiments, according to (or as applied to) any of the embodiments above, the anti-CD73 antibody, the variant or antigen binding fragment thereof, is conjugated to a label. In some embodiments, according to (or as applied to) any of the embodiments above, the label is selected from the group consisting of a radioisotope, a fluorescent dye, and an enzyme.

The present disclosure provides an isolated nucleic acid molecule that encodes the anti-CD73 antibody, the variant, the mutant, or antigen binding fragment thereof, according to (or as applied to) any of the embodiments above. Also provided is an expression vector encoding the nucleic acid molecule according to (or as applied to) any of the embodiments above. Cells comprising the expression vector according to (or as applied to) any of the embodiments above are also provided. The present disclosure also provides a method of producing an anti-CD73 antibody, the variant or the antigen binding fragment thereof, comprising culturing a cell according to (or as applied to) any of the embodiments above and recovering the antibody or antigen binding fragment thereof from the cell culture. In some embodiments, according to (or as applied to) any of the embodiments above, the cell is a mammalian cell. In some embodiments, according to (or as applied to) any of the embodiments above, the mammalian cell is a CHO cell. In some embodiments, according to (or as applied to) any of the embodiments above, the cell is a stable mammalian cell line. In some embodiments, according to (or as applied to) any of the embodiments above, the stable mammalian cell line is a CHO cell line.

In certain embodiment, provided is an isolated antibody that specifically binds human CD73 at the surface of a cell and that is capable of neutralizing the 5'-ectonucletidase activity of soluble or membrane-bound human CD73 proteins. The antibody can induce the intracellular internalization of CD73.

In certain embodiment, provided is an antibody that binds and is capable of inhibiting the enzymatic activity of soluble or membrane-bound human CD73 proteins, wherein said antibody is not internalized into CD73 expressing cells.

The present disclosure provides a composition comprising the anti-CD73 antibody, the variant, the mutant, or antigen binding fragment thereof, according to (or as applied to) any of the embodiments above and a pharmaceutically acceptable carrier.

The present disclosure provides a method of detecting a CD73 protein in sample from a patient by contacting the anti-CD73 antibody, the variant, the mutant, or antigen binding fragment thereof, according to (or as applied to) any of the embodiments above to the sample and detecting the anti-CD73 antibody bound to the CD73 protein. In some embodiments, according to (or as applied to) any of the embodiments above, the anti-CD73 antibody, the variant or antigen binding fragment thereof, is used in an immunohistochemistry assay (IHC) or in an ELISA assay.

Also provided is a method of treating cancer in a subject, comprising administering an effective amount of the composition according to (or as applied to) any of the embodiments above to the subject. Also provided is a composition comprising an anti-CD73 antibody, the variant, the mutant, or antigen binding fragment thereof, according to (or as applied to) any of the embodiments above for use in the treatment of cancer. Provided is the use of an anti-CD73 antibody, the variant, the mutant, or antigen binding fragment thereof, according to (or as applied to) any of the embodiments above in the manufacture of a medicament for treating cancer, such as a cancer associated with expression of CD73.

In some embodiments according to (or as applied to) any of the embodiments above, the cancer is selected from melanoma, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer and non-small cell lung cancer (NSCLC), esophageal cancer, nasopharyngeal carcinoma (NPC), biliary tract cancer, colorectal cancer, cervical cancer, thyroid cancer, and salivary cancer. In some embodiments, according to (or as applied to) any of the embodiments above, the subject is further administered a therapeutic agent selected from the group consisting of an antineoplastic agent, a chemotherapeutic agent, a growth inhibitory agent and a cytotoxic agent. In some embodiments, according to (or as applied to) any of the embodiments above, the subject is further administered a radiation therapy and/or a surgery.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings.

FIGS. 1A-1B. Amino acid sequence alignment of light chain (FIG. 1A) (FIG. 1A discloses SEQ ID NOS 79-81, respectively, in order of appearance) and heavy chain variable region (FIG. 1B) (FIG. 1B discloses SEQ ID NOS 97-99, respectively, in order of appearance) of anti-CD73 selected leads N1, N2 and N4 from naïve phage panning. Three selected antibody leads with binding and blocking activity of CD73 enzyme were identified by screening of human Fab naïve phage display library with human CD73-ECD/His. The selected variable sequences were then cloned into L234F, L235E, P331S mutant of human IgG1 Fc backbone to become full-length antibodies. Sequence alignment of the antibody leads was listed here and Kabat defined CDRs (Complementary Determining Regions) were underlined and marked in bold.

Figure 6A:
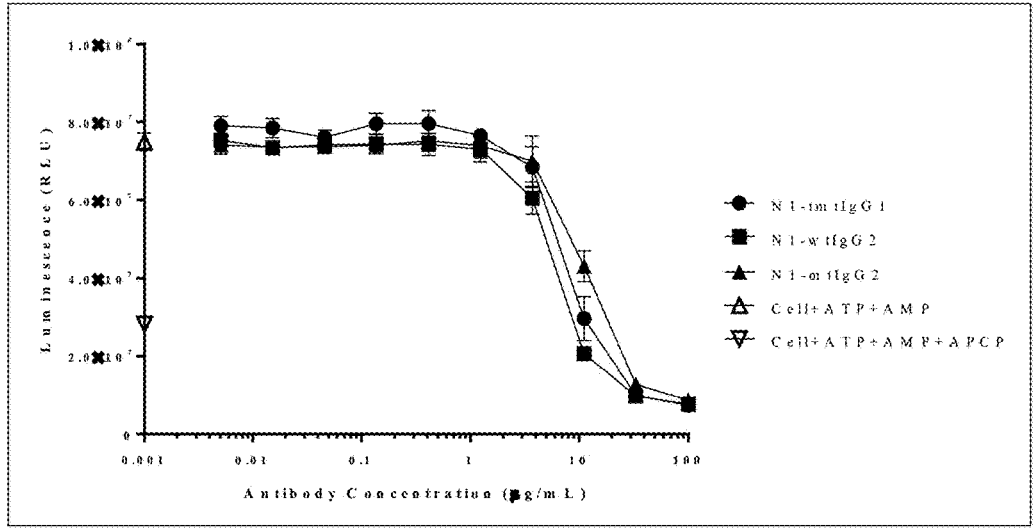
Figure 6B:
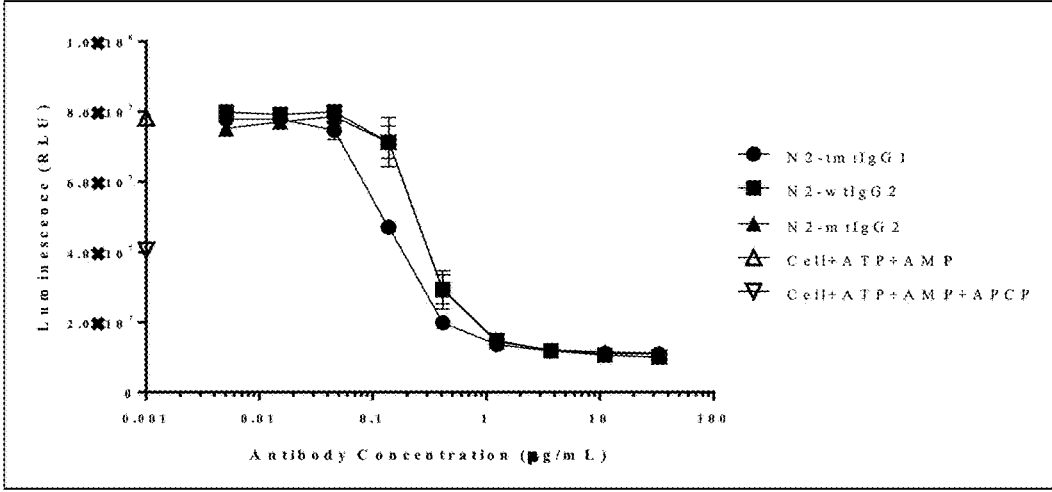
Figure 6C:
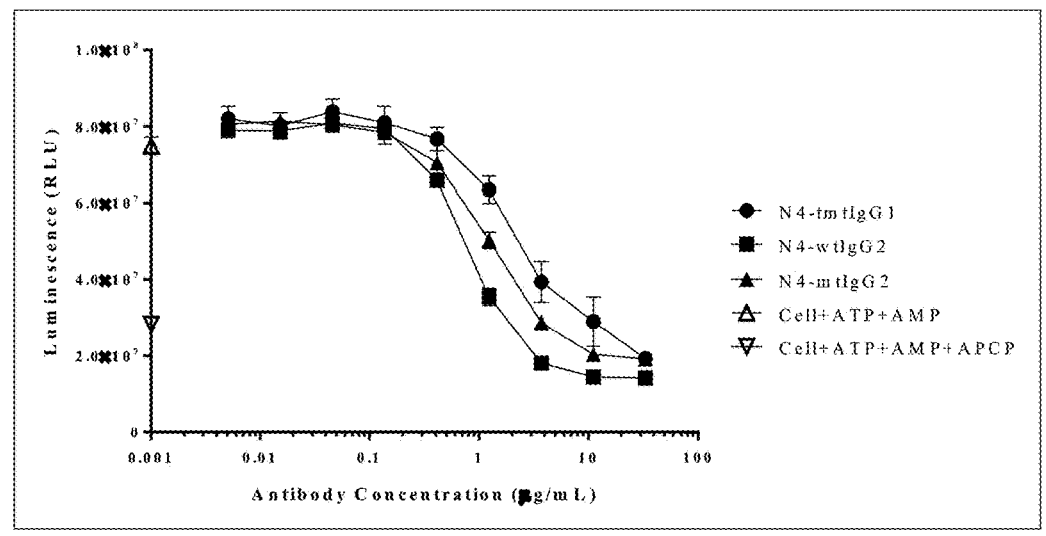

FIGS. 6A-6C. Effects of anti-CD73 leads with different IgG Fc regions on cellular CD73 enzyme activity. Anti-CD73 leads N1 (FIG. 6A), N2 (FIG. 6B), N4 (FIG. 6C) with different IgG isotypes were tested for their ability to inhibit the cellular CD73 enzyme activity. MDA-MB-231 cells were incubated with anti-CD73 antibodies. ATP, AMP and CellTiter-Glo® reagent were added and the luminescence was recorded. APCP was used as the positive control in the enzyme activity assay.

Figure 7A:
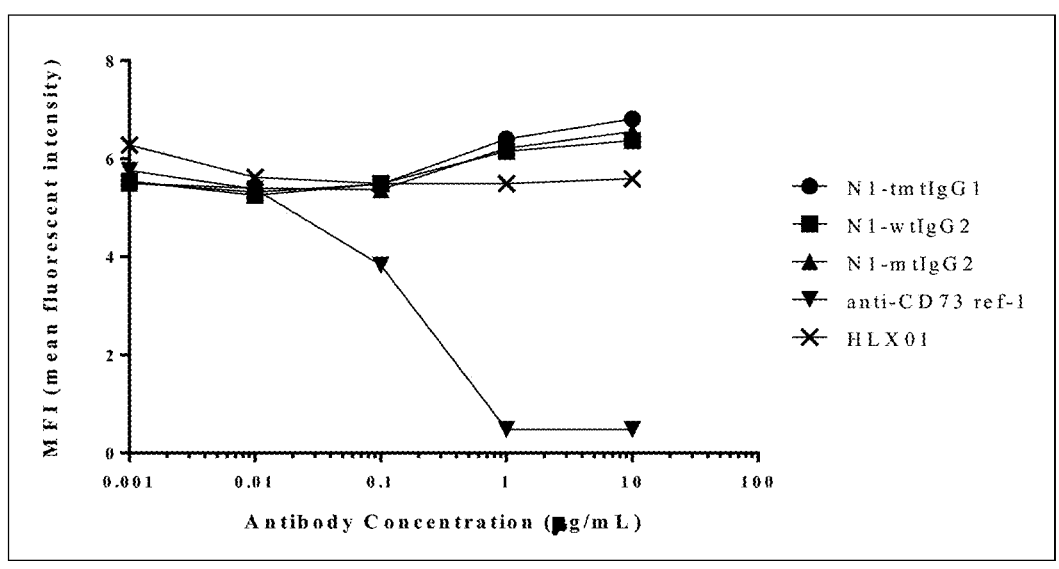
Figure 7B:
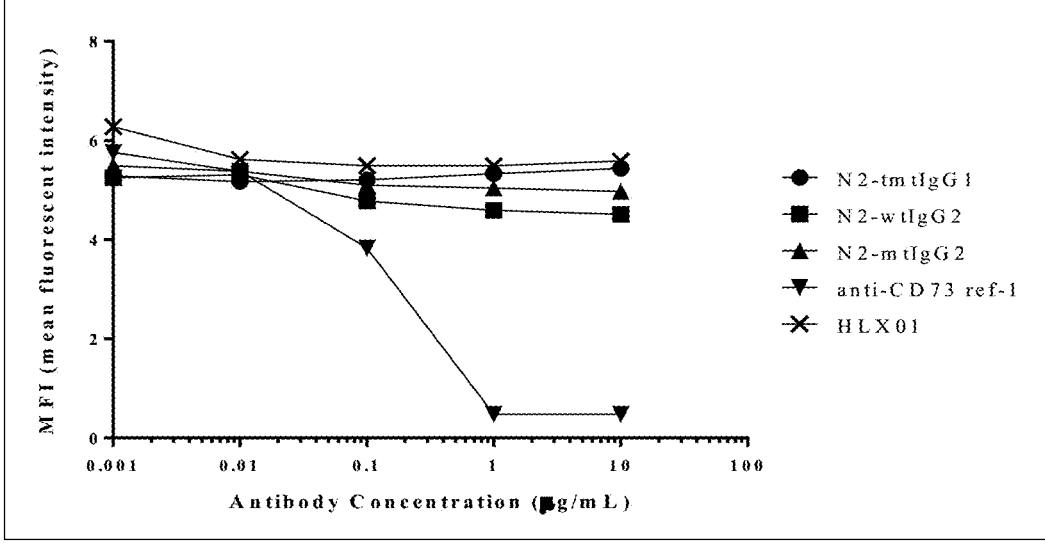
Figure 7C:
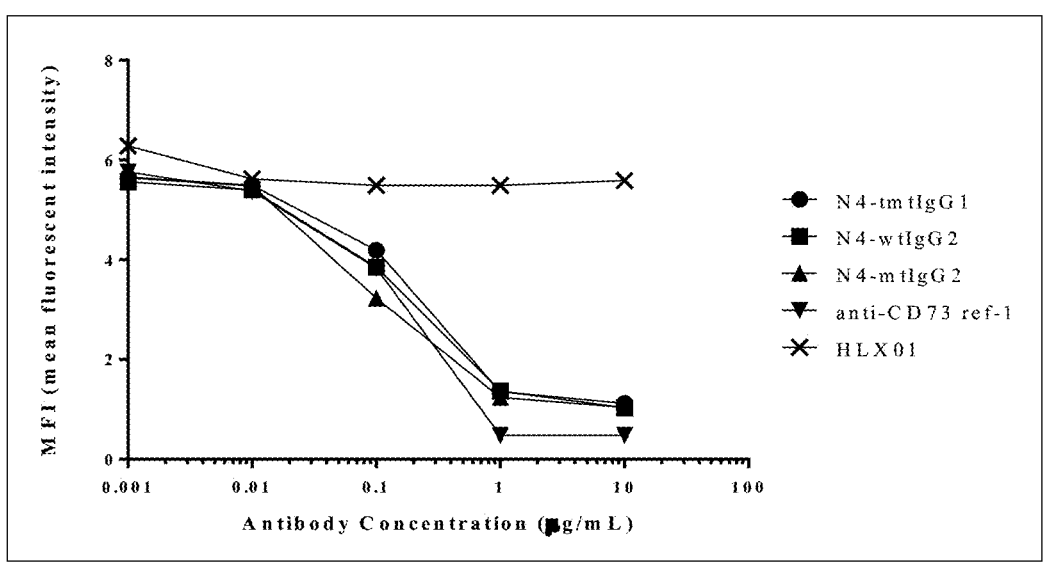

FIGS. 7A-7C. Antibody-mediated CD73 internalization of anti-CD73 antibodies with different IgG Fc regions. After incubating cells with different IgG isotypes of N1 (FIG. 7A), N2 (FIG. 7B), and N4 (FIG. 7C), the cell surface expression of CD73 was measured by flow cytometry. Anti-CD73 ref-1 antibody and HLX01 (anti-CD20) were used as the positive and negative control respectively.

Figure 8A:
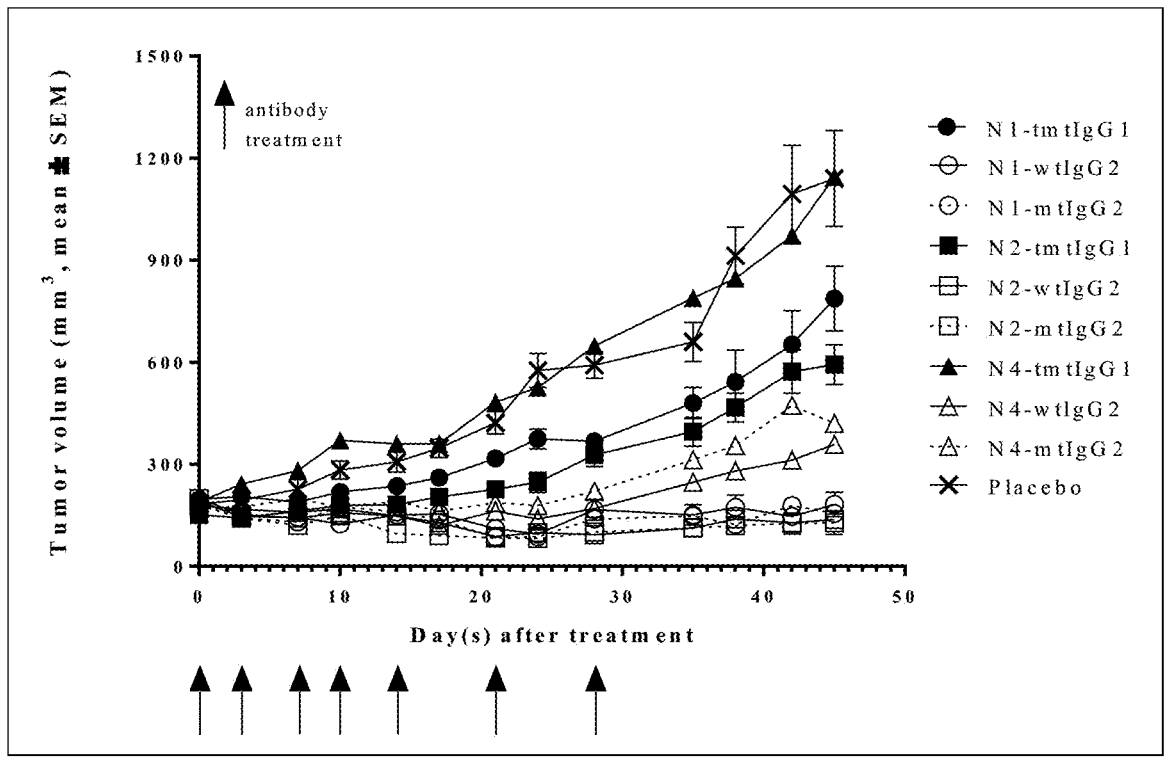
Figure 8B:
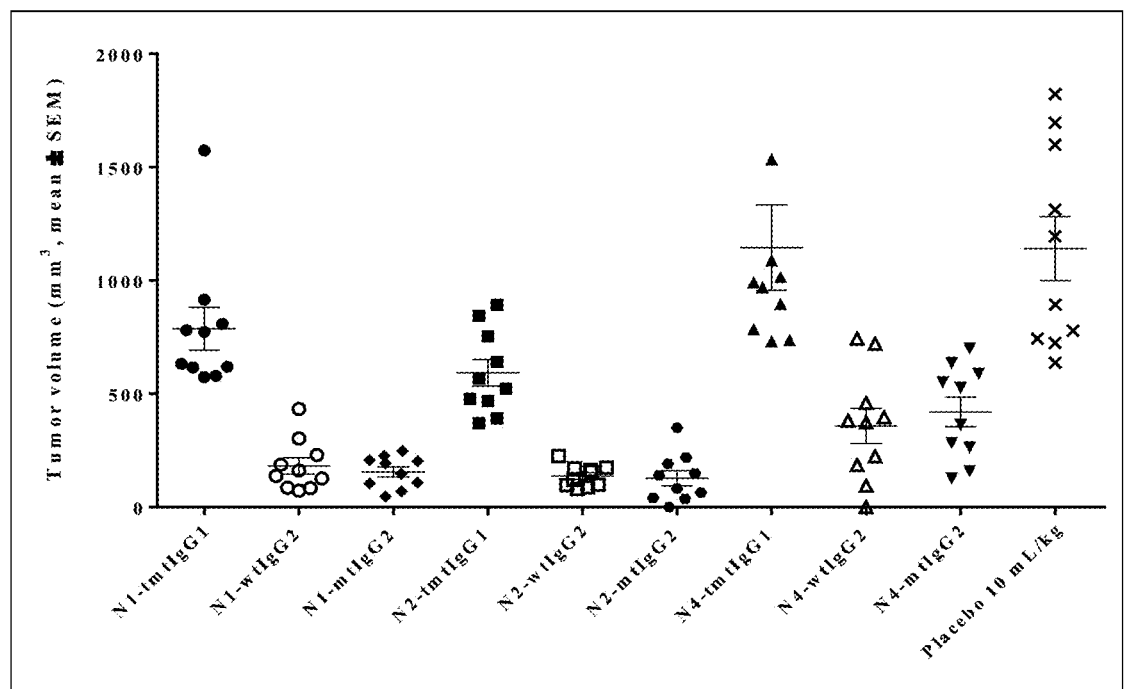

FIGS. 8A-8B. Tumor growth inhibition activity of anti-CD73 leads in MDA-MB-231 (human triple-negative breast cancer) xenograft mouse model. Mice (n=5 mice/group) were subcutaneously engrafted with MDA-MB-231 cells. The first dose of test article was administered 14 days after tumor inoculation when the engrafted tumor size reached 150-300 mm$^3$. Mice were intraperitoneally treated with 5 mg/kg antibodies at indicated time. Tumor growth curves were shown in FIG. 8A. The individual tumor volume at day 45 was presented in FIG. 8B. All data points are the means±SEM.

FIG. 9. Amino acid sequence alignment of light chain variable region of N1 and N4 variants derived from affinity maturation. N1 and N4 variants with better CD73 binding affinity and soluble CD73 enzyme blocking activity were identified from in vitro phage display-based affinity maturation experiments. Kabat defined CDRs (Complementary Determining Regions) were underlined and marked in bold. FIG. 9 discloses SEQ ID NOS 82-85, 88, 86-87 and 89-92, respectively, in order of appearance.

FIG. 10. Amino acid sequence alignment of heavy chain variable region of N1 and N4 variants derived from affinity maturation. N1 and N4 variants with better CD73 binding affinity and soluble CD73 enzyme blocking activity were identified from in vitro phage display-based affinity maturation experiments. Kabat defined CDRs (Complementary Determining Regions) were underlined and marked in bold. These selected variable sequences were then cloned into human IgG2 Fc backbone to become full-length antibodies. FIG. 10 discloses SEQ ID NOS 100-103, 106, 104-105 and 107-110, respectively, in order of appearance.

Figure 11A:
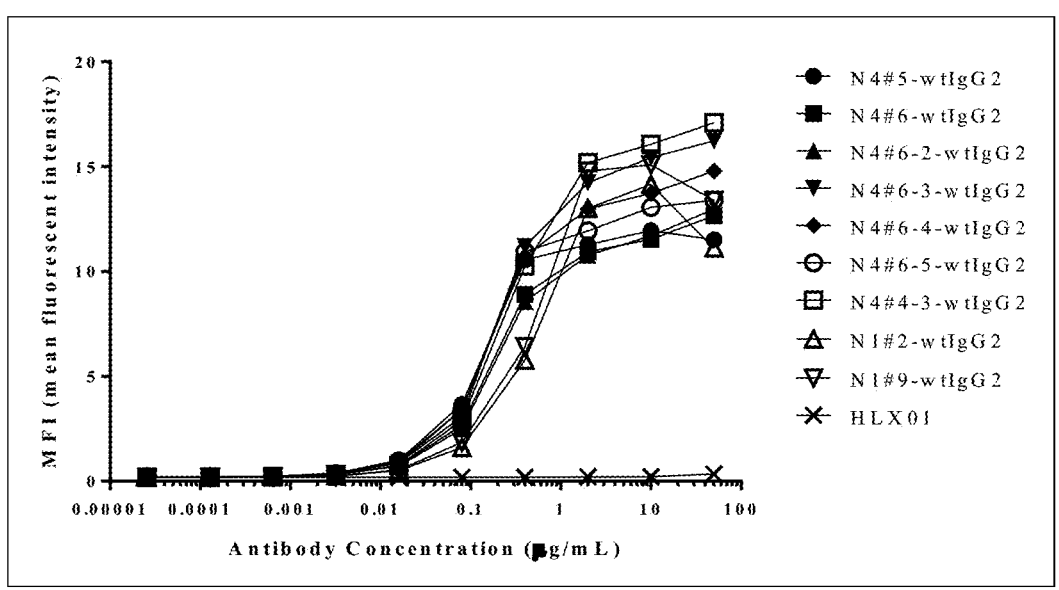
Figure 11B:
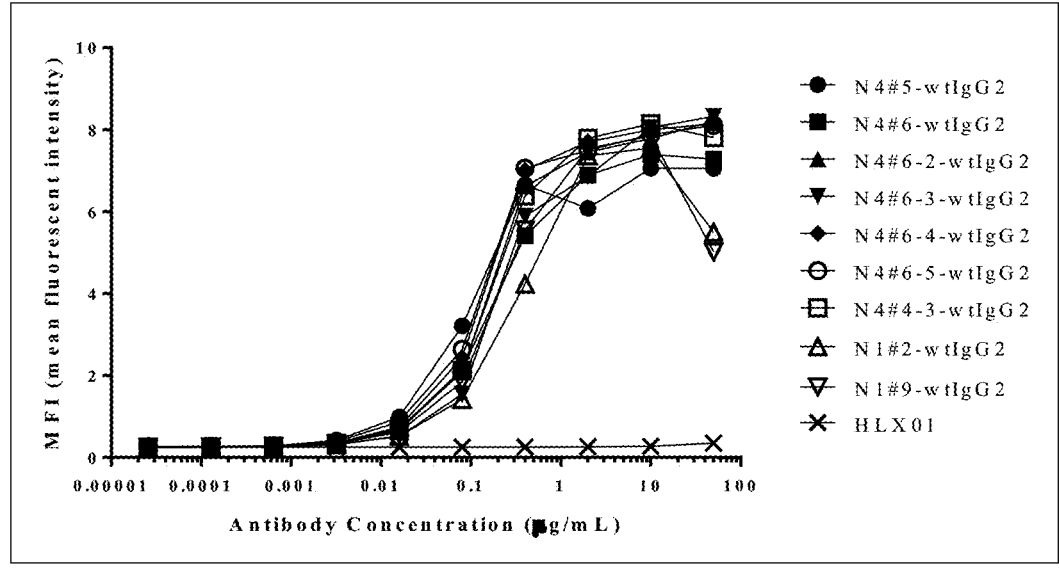

FIGS. 11A-11B. CD73 binding of N1 and N4 variants. Selected variants were tested the binding to CD73-expressing MDA-MB-231 (FIG. 11A) and NCI-H292 cells (FIG. 11B) by flow cytometry. HLX01 (anti-CD20) was used as the negative control.

Figure 12:
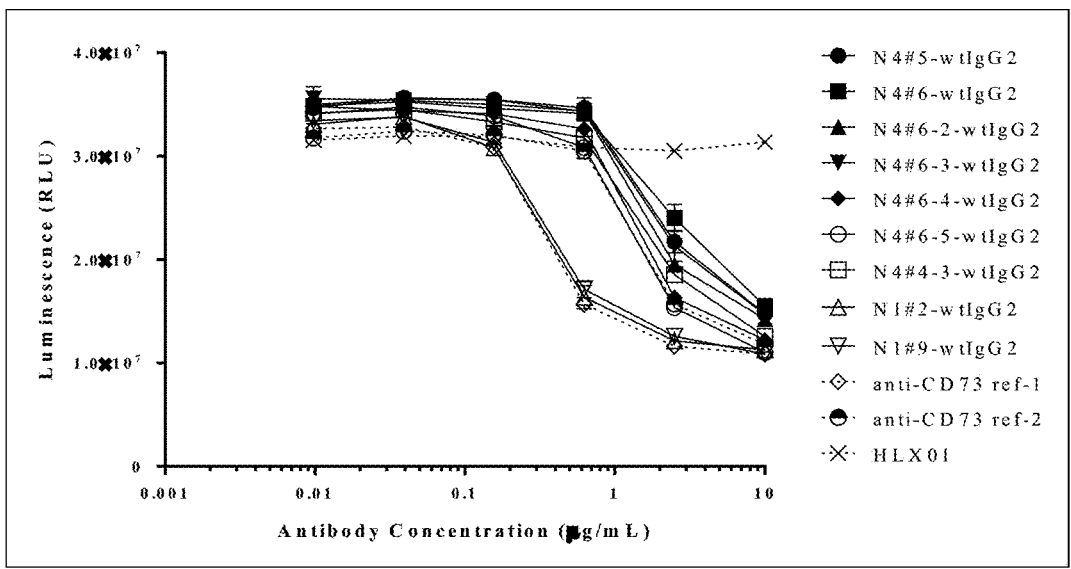

FIG. 12. Effects of N1 and N4 variants on immobilized CD73 enzyme activity. N1 and N4 variants were tested for their ability to inhibit the immobilized CD73 enzyme activity. After incubation of anti-CD73 antibodies and CD73 proteins, ATP, AMP and CellTiter-Glo® reagent were added and the luminescence was recorded. Anti-CD73 ref-1 antibody, anti-CD73 ref-2 antibody were used as the positive controls, while HLX01 (anti-CD20) was used as the negative control.

Figure 13:
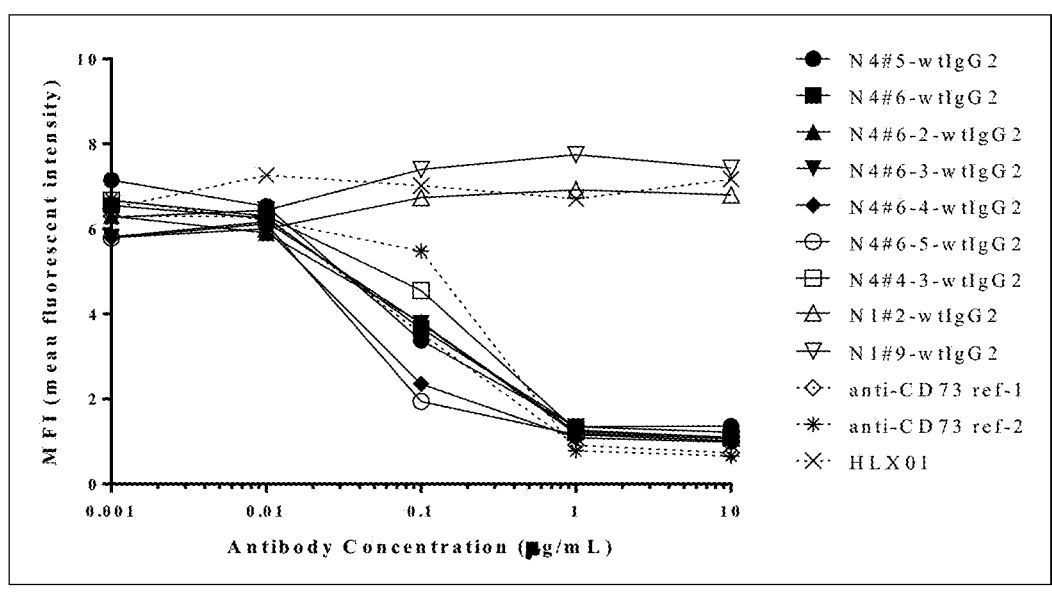

FIG. 13. Antibody-mediated CD73 internalization of N1 and N4 variants. The NCI-H292 cells were incubated with N1 and N4 variants, and the cell surface expression of CD73 was measured by flow cytometry. Anti-CD73 ref-1 antibody and anti-CD73 ref-2 antibody were used as the positive controls, while HLX01 (anti-CD20) was used as the negative control.

FIG. 14. Amino acid sequence alignment of light chain of N1 and N4 top variants. Kabat defined CDRs (Complementary Determining Regions) were underlined and marked in bold. FIG. 14 discloses SEQ ID NOS 93-96, respectively, in order of appearance.

FIG. 15. Amino acid sequence alignment of heavy chain variable region of N1 and N4 top variants. Kabat defined CDRs (Complementary Determining Regions) were underlined and marked in bold. These sequences were then cloned into human IgG2 Fc backbone to become full-length antibodies. FIG. 15 discloses SEQ ID NOS 111, 101 and 108-109, respectively, in order of appearance.

Figure 16A:
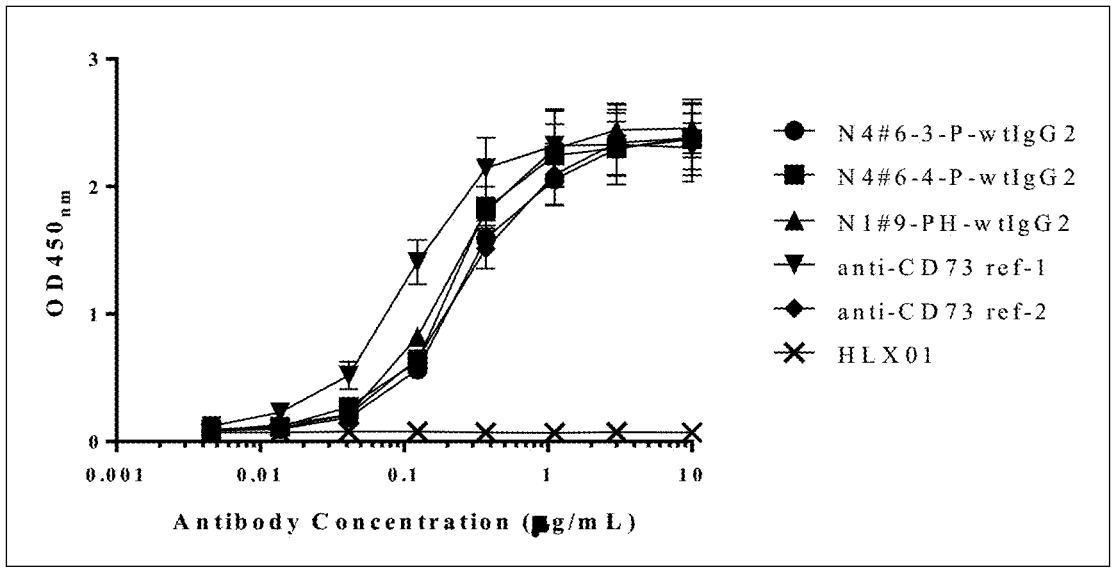
Figure 16B:
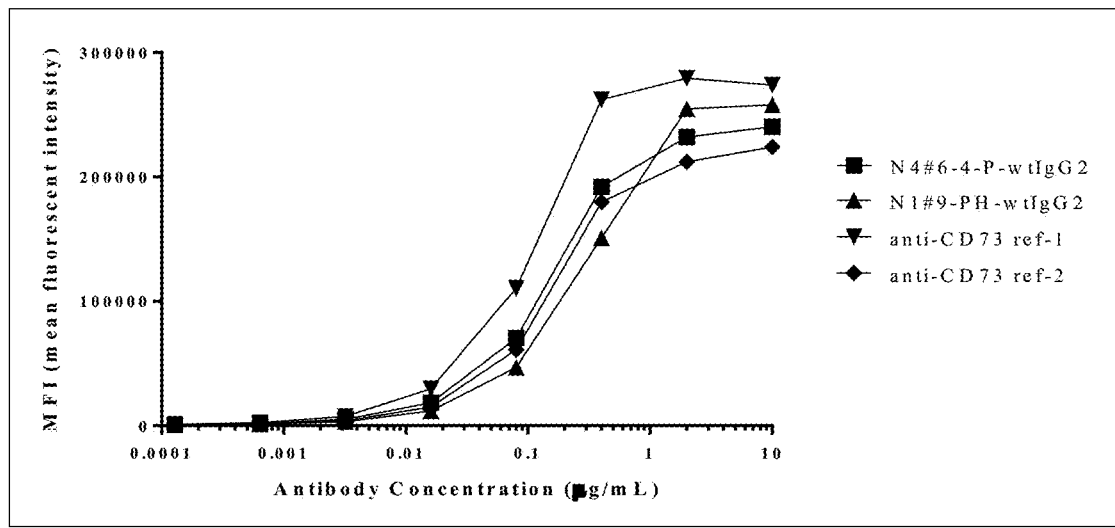
Figure 16C:
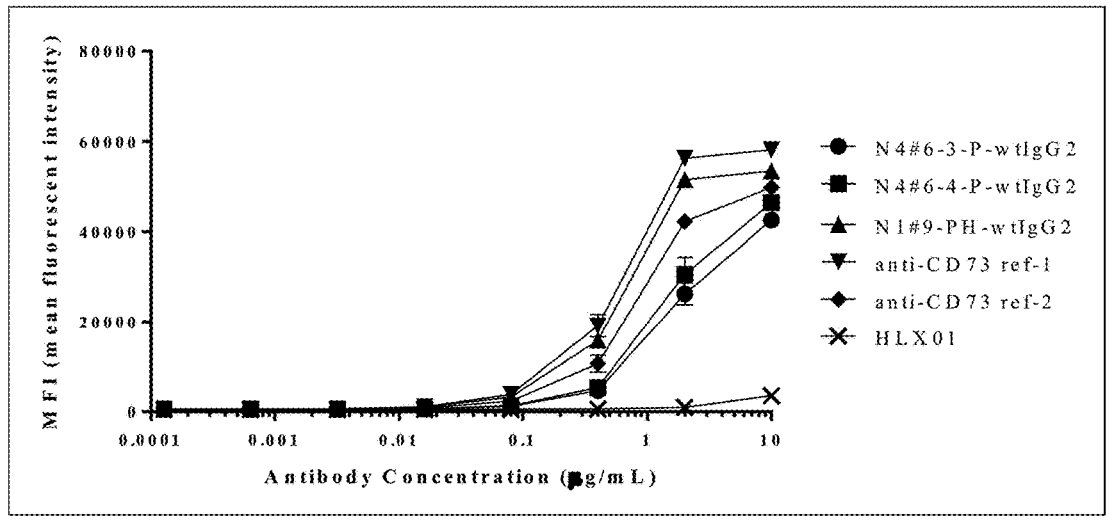

FIGS. 16A-16C. CD73 binding ability of N1 and N4 top variants. Anti-CD73 antibodies were tested the binding to recombinant human CD73 proteins by ELISA (FIG. 16A) and CD73-expressing human tumor cells, MDA-MB-231 (FIG. 16B) and NCI-H292 (FIG. 16C), by flow cytometry. Anti-CD73 ref-1 and anti-CD73 ref-2 antibodies were used as the positive controls, while HLX01 (anti-CD20) was used as the negative control.

Figure 17A:
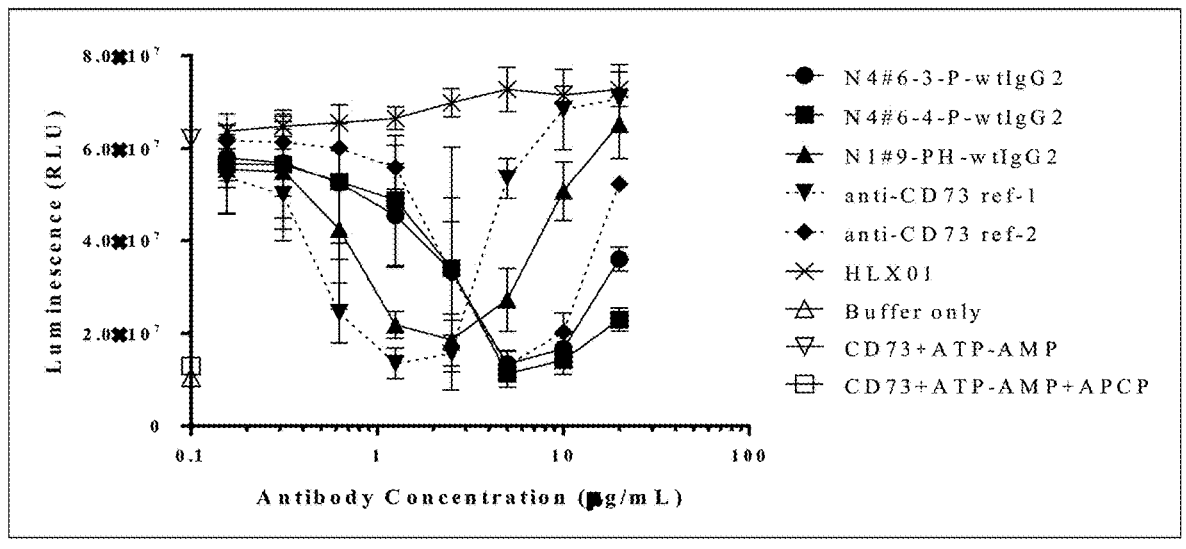
Figure 17B:
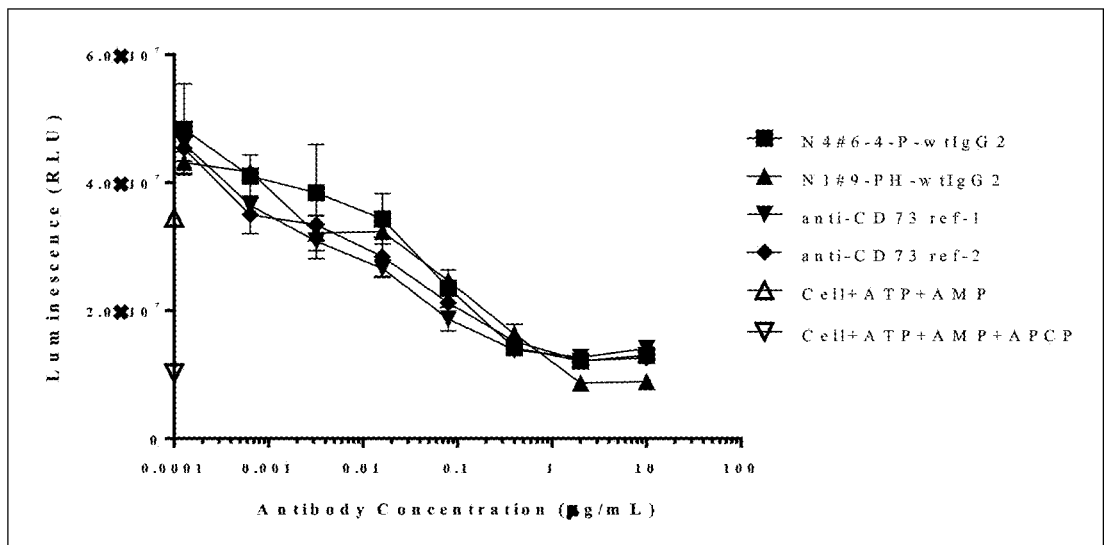
Figure 17C:
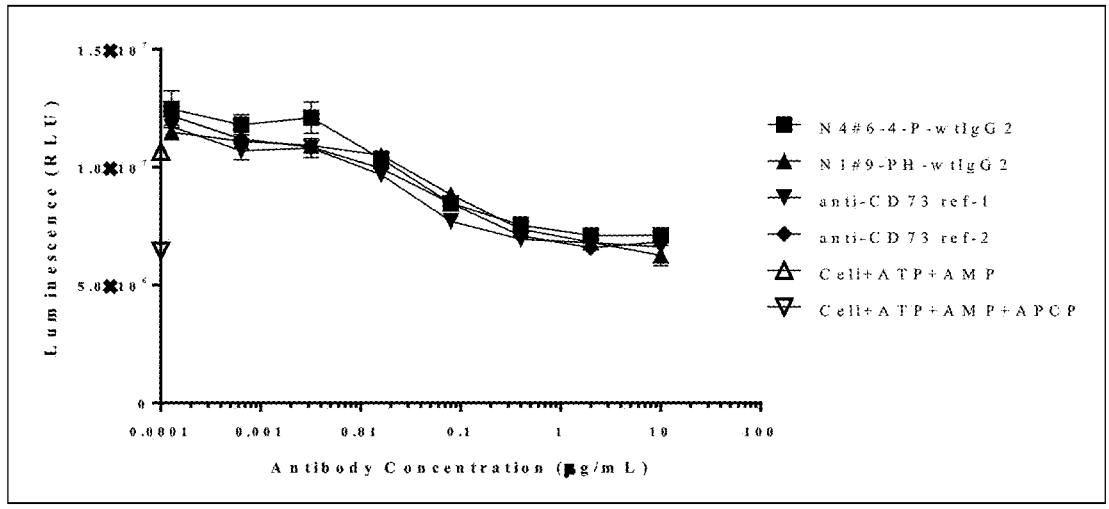

FIGS. 17A-17C. Effects of N1 and N4 top variants on soluble CD73 enzyme activity (FIG. 17A) and cell surface CD73 enzyme activity (FIG. 17B, FIG. 17C). Anti-CD73 antibodies were tested for their ability to inhibit the human recombinant CD73 protein and cell surface CD73 enzyme activity. Recombinant CD73 proteins (FIG. 17A), MDA-MB-231 (FIG. 17B) and NCI-H292 (FIG. 17C) cells were incubated with anti-CD73 antibodies. ATP, AMP and Cell-Titer-Glo® were added and the luminescence was recorded. Anti-CD73 ref-1 antibody, anti-CD73 ref-2 antibody, and APCP were used as the positive controls. HLX01 (anti-CD20) was used as the negative control.

Figure 18A:
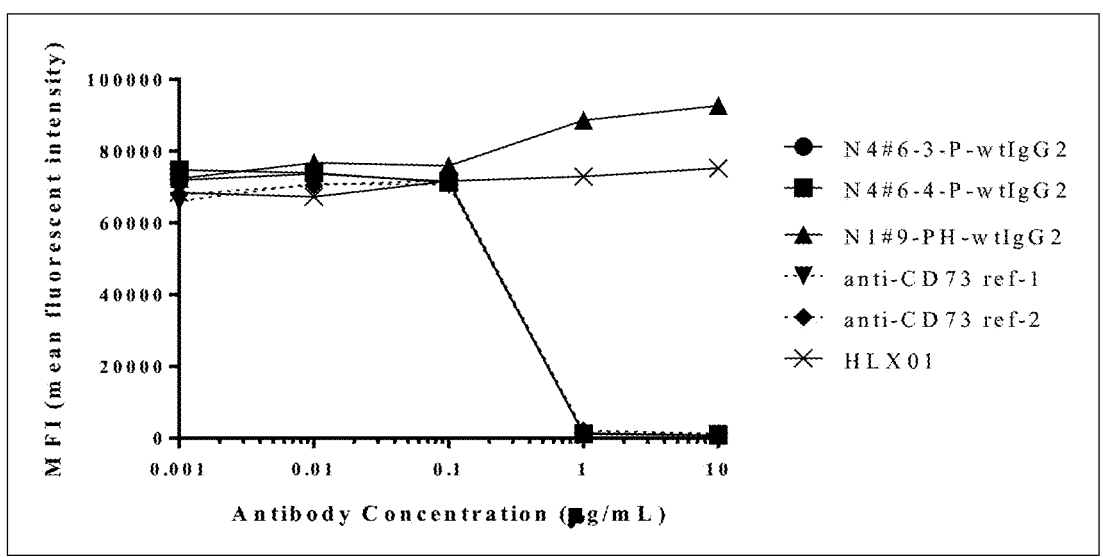
Figure 18B:
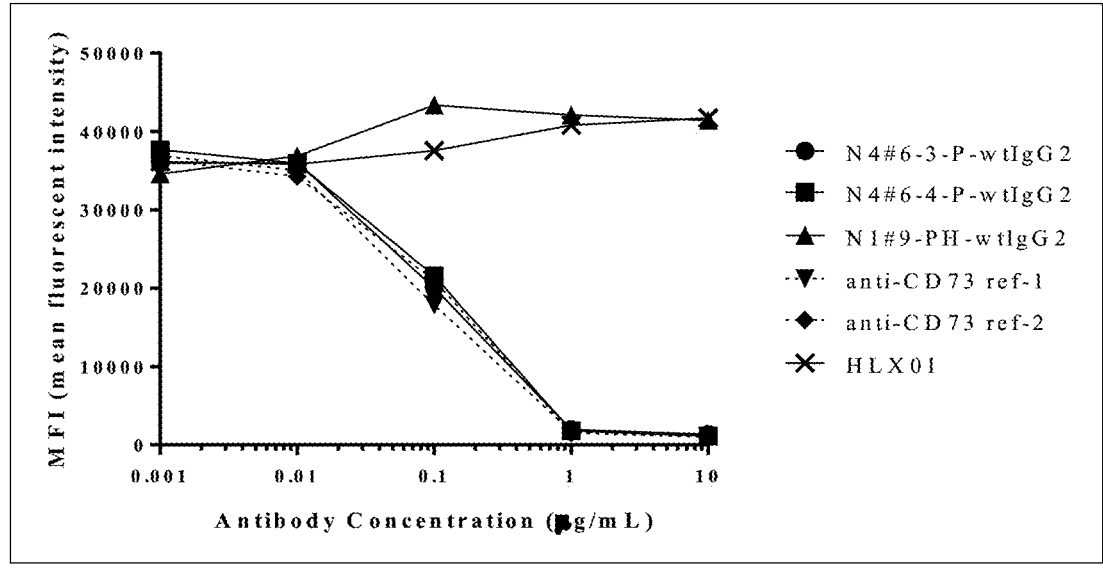

FIGS. 18A-18B. Antibody-mediated CD73 internalization of N1 and N4 top variants. MDA-MB-231 (FIG. 18A) and NCI-H292 (FIG. 18B) cells were incubated with anti-CD73 N1 and N4 variants. After the incubation, the cell surface expression of CD73 was measured by flow cytometry. Anti-CD73 ref-1 and anti-CD73 ref-2 antibodies were used as the positive controls, while HLX01 (anti-CD20) was used as the negative control.

Figure 19A:
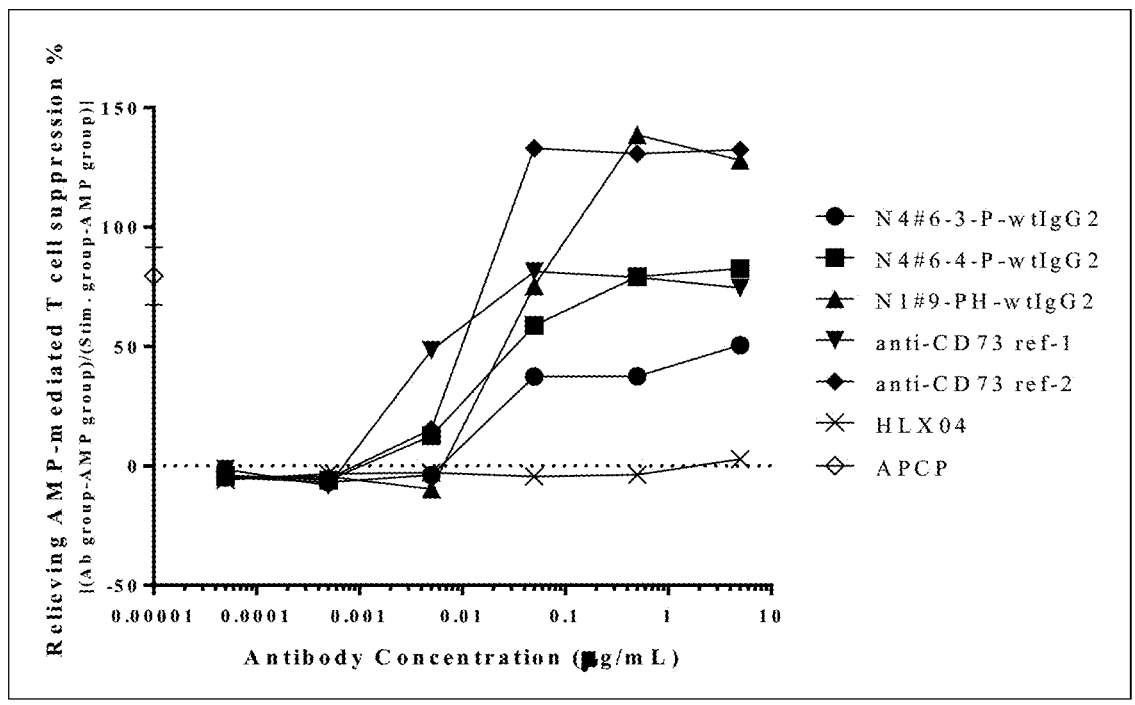
Figure 19B:
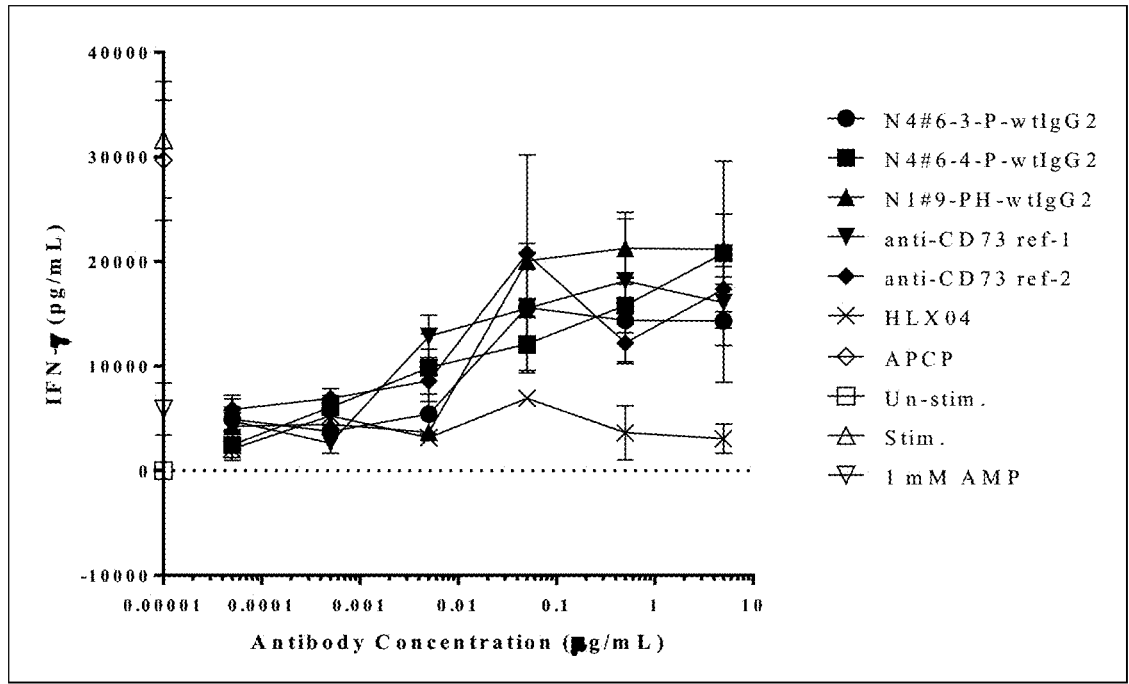

FIGS. 19A-19B. Reversing suppressive effects of AMP on T cell activity by N1 and N4 top variants. Isolated human T cells were cultured with CD3/CD28 beads, AMP and serially diluted antibodies for 4 days at 37° C. Proliferation of CD3 T cells was followed by CellTiter-Glo® assay (FIG. 19A), and the IFN-γ secretion was measured using Human IFN-γ ELISA MAX™ Deluxe kits (FIG. 19B). Anti-CD73 ref-1 and anti-CD73 ref-2 antibodies were used as the positive controls, while HLX04 (anti-VEGF) was used as the negative control.

Figure 20:
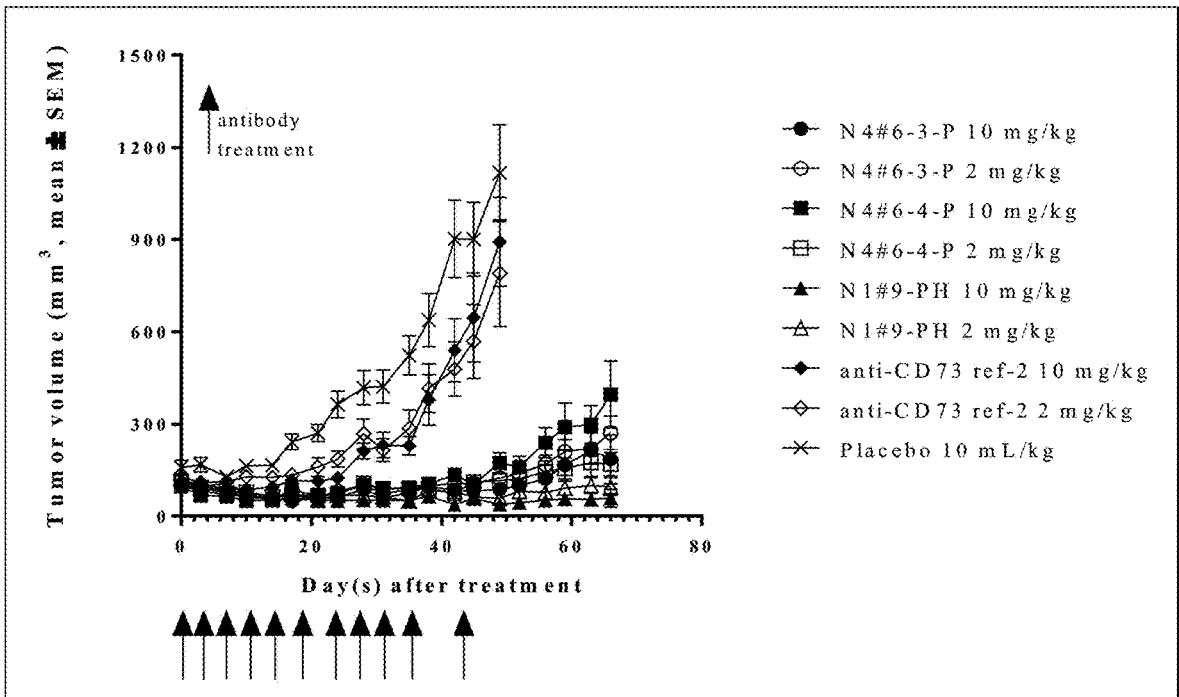

FIG. 20. Tumor growth inhibition activity of N1 and N4 top variants in MDA-MB-231 (human triple-negative breast cancer) xenograft mouse model. Mice (n=5 mice/group) were subcutaneously engrafted with MDA-MB-231 cells. The first dose of test article was administered 7 days after tumor inoculation when the engrafted tumor size reached about 100 mm$^3$. Mice were intraperitoneally treated with 10 mg/kg and 2 mg/kg of antibodies twice per week for 5-6 weeks. All data points are the means±SEM.

Figure 21:
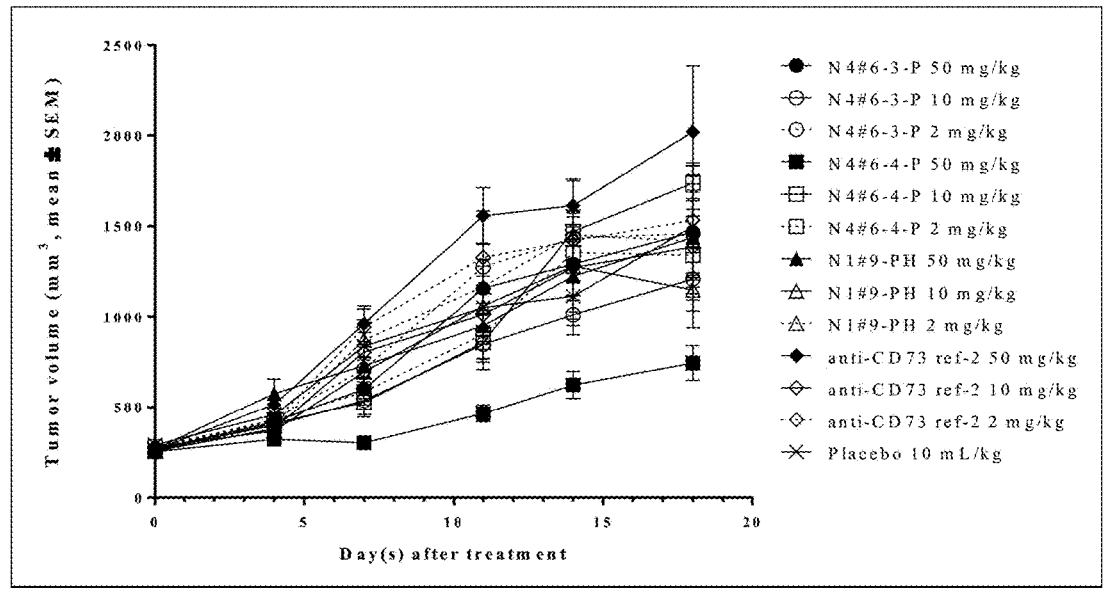

FIG. 21. Tumor growth inhibition activity of N1 and N4 top variants in NCI-H292 (human mucoepidermoid pulmonary carcinoma) xenograft mouse model. Mice (n=5 mice/ group) were subcutaneously engrafted with NCI-H292 cells. The first dose of test article was administered 3 days after tumor inoculation. Mice were intraperitoneally treated with 50, 10 and 2 mg/kg of antibodies twice per week for 3 weeks. All data points are the means±SEM.

Figure 22:
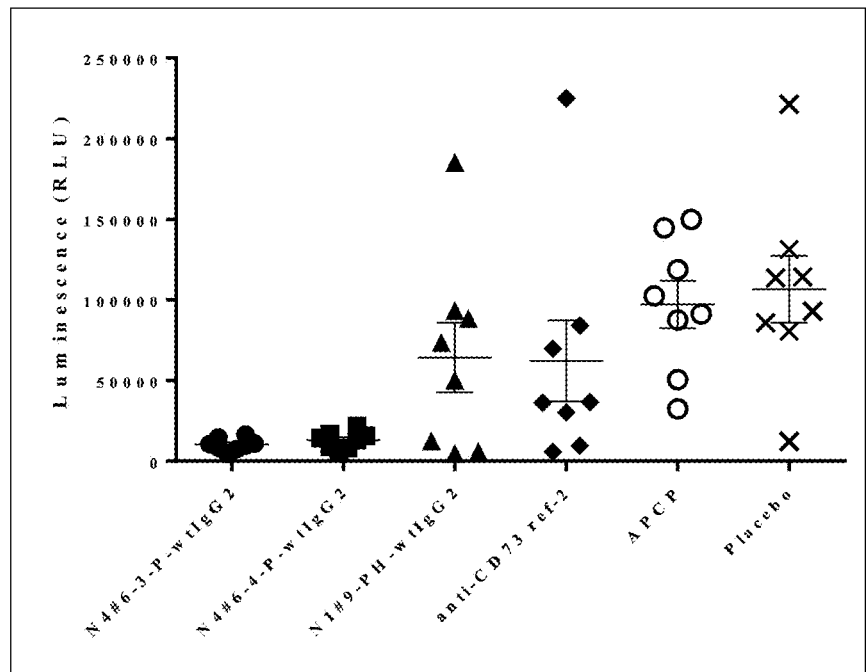

FIG. 22. Effects of N1 and N4 top variants on cellular CD73 enzyme activity in NCI-H292 xenograft tumors. N1 and N4 top variants were tested for their ability to inhibit the CD73 enzyme activity in NCI-H292 xenograft model. Mice (n=4 mice/group) were subcutaneously engrafted with NCI-H292 cells 4 days before the antibody treatment. Antibodies, APCP, and placebo were intraperitoneally injected at day 0. Tumors were resected at days 1, 3 and 7 after antibody administration. The CD73 enzyme activity in tumors were measured by CellTiter-Glo® assay.

Figure 23A:
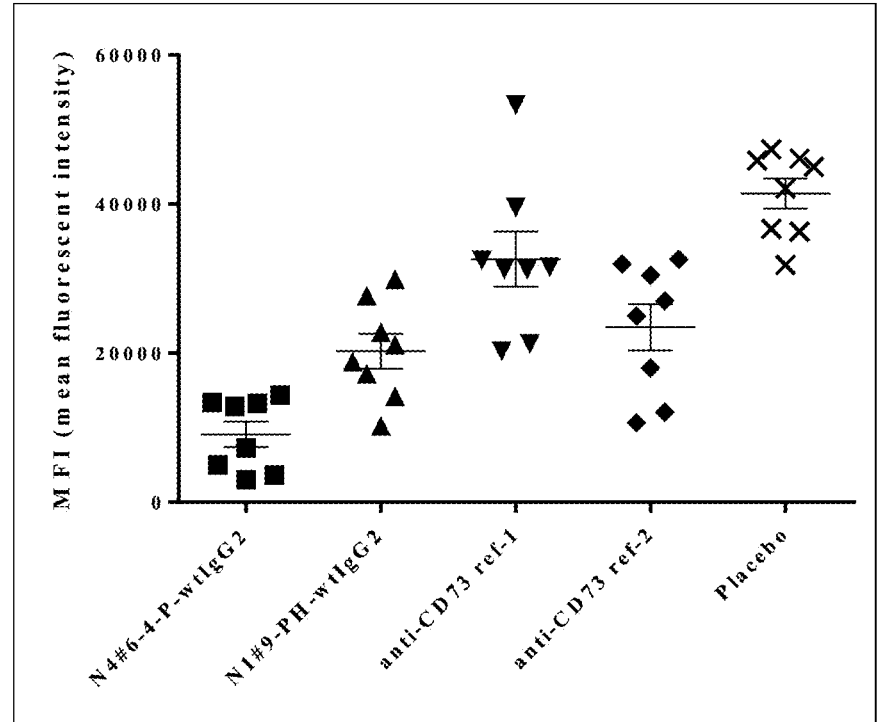
Figure 23B:
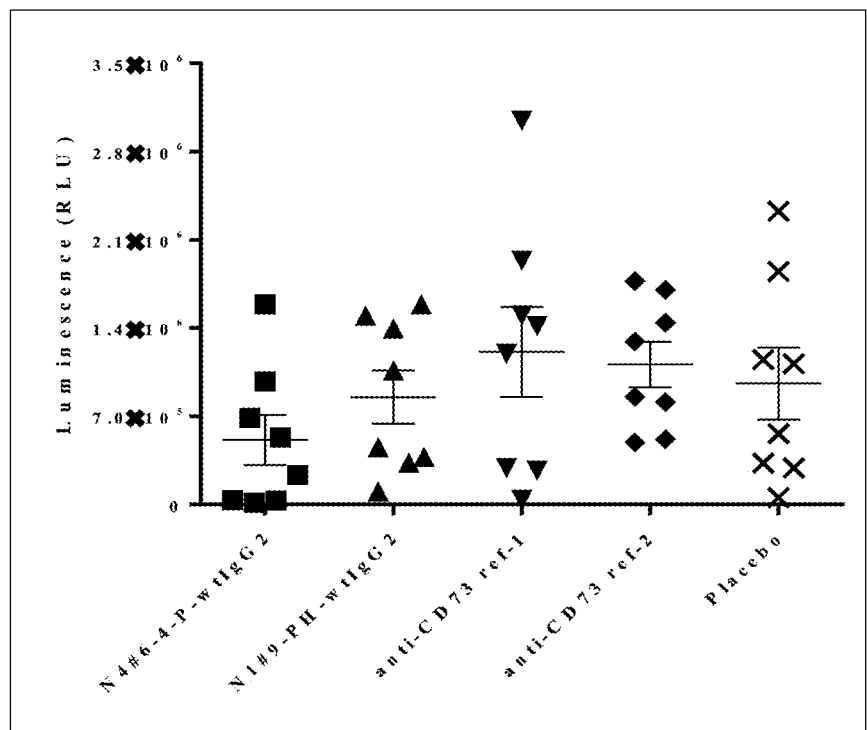

FIGS. 23A-23B. Effects of N1 and N4 top variants on CD73 expression and cellular CD73 enzyme activity in MDA-MB-231 xenograft tumors. Anti-CD73 antibodies were tested for their ability to downmodulate the surface CD73 expression and inhibit the CD73 enzyme activity in MDA-MB-231 xenograft model. Mice (n=4 mice/group) were subcutaneously engrafted with MDA-MB-231 cells 7 days before the antibody treatment. Antibodies and placebo were injected at day 0. Tumors were collected at day 1, 3 and 7 after antibody administration. The CD73 expression was measured by the mean fluorescent intensity (MFI) of staining (FIG. 23A) and the CD73 enzyme activity in tumors were measured by CellTiter-Glo® assay (FIG. 23B).

Figure 24A:
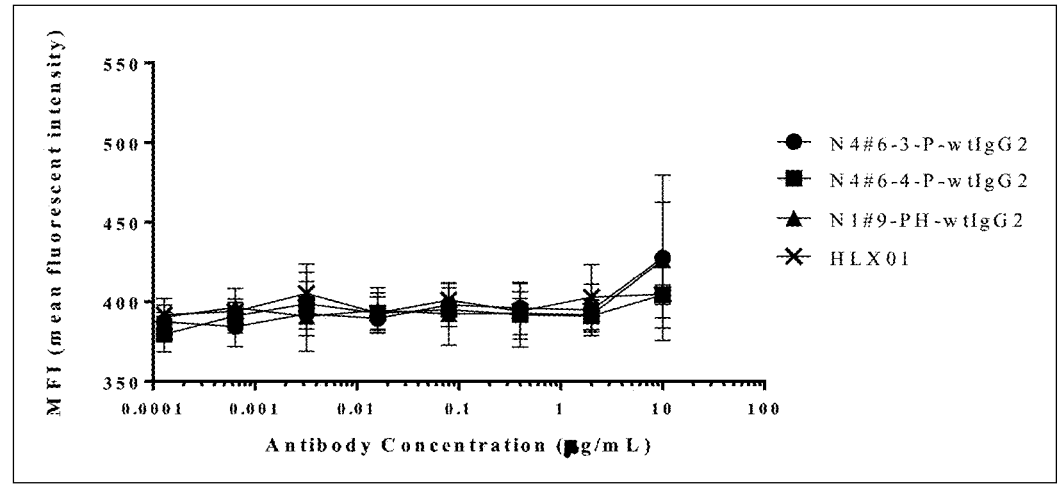
Figure 24B:
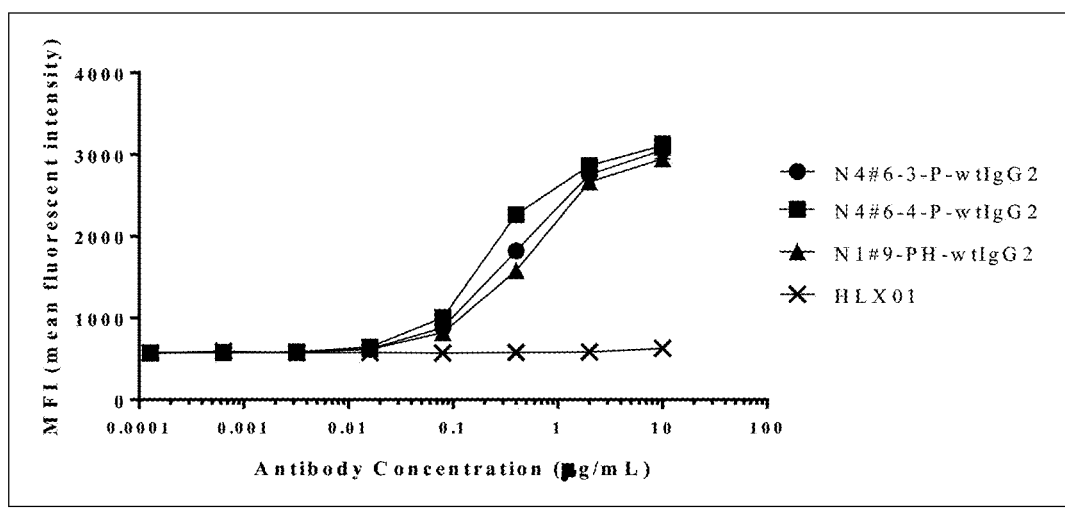

FIGS. 24A-24B. Cross-binding of N1 and N4 top variants to mouse and monkey CD73-expressing cells. Anti-CD73 antibodies were tested for the binding to CD73-expressing mouse mammary carcinoma 4T1 cells (FIG. 24A) and monkey kidney epithelial LLC-MK2 cells (FIG. 24B) by flow cytometry. HLX01 was used as the negative control.

Additional advantages of the present disclosure will be set forth in part in the description which follows, and in part will be obvious from the description, or can be learned by practice of the present disclosure. The advantages of the present disclosure will be realized and attained by means of the elements and combinations particularly pointed out in the appended claims. It is to be understood that both the foregoing general description and the following detailed description are exemplary and explanatory only and are not restrictive of the present disclosure, as claimed.

DETAILED DESCRIPTION

The present disclosure, in one aspect, relates to anti-CD73 antibodies, variants, mutants, and/or antigen binding fragments thereof, methods of making same, pharmaceutical compositions comprising same, and methods of treating a human subject using same. The present disclosure further provides that the anti-CD73 antibodies bind specifically to CD73 and can inhibit tumor growth via induce macrophage-mediated phagocytosis. The disclosed antibodies demonstrate improved efficacy and/or anti-tumor activities compared to conventional anti-CD73 monoclonal antibodies used to treat a clinical conditions such as a cancer or fibrosis. Also provided are immunoconjugates, nucleic acids encoding the novel anti-CD73 antibodies, their affinity variants or antigen binding fragments thereof, as described herein, and compositions (such as pharmaceutical compositions).

In certain embodiments, the present disclosure provides at least eighteen (18) anti-CD73 antibodies, variants, mutants, and/or antigen binding fragments thereof, namely, anti-CD73 antibodies, variants, and/or mutant, which are designated as in Tables 1 and 2. The nucleic acid and/or its encoding amino acid sequences of the light chain and heavy chain of each of these anti-CD73 antibodies, variants, and/or mutants thereof, are provided in the Disclosed Sequences-Sequence Listing section herein below. The CDR sequences of each light chain (CDR-L1, CDR-L2, and CDR-L3) and each heavy chain (CDR-H1, CDR-H2, and CDR-H3) of each anti-CD73 antibody, variant, and/or mutant thereof, are provided in Tables 1 and 2, respectively.

The present disclosure also provides methods of using novel anti-CD73 antibodies, the affinity variants and/or mutants, or antigen binding fragments thereof, to detect CD73 in a sample (such as an in vivo or ex vivo sample), and/or the compositions comprising such antibodies, the variants and/or mutants, or antigen binding fragments thereof, for use in treating a clinical condition or disease associated with CD73 expression, CD73 overexpression, and/or abnormal CD73 function, such as a cancer or fibrosis. In other embodiments, the disclosed anti-CD73 antibodies and their affinity variants and/or mutants or antigen binding fragments can be used in combination with other agents in treating disease associated with CD73 expression, CD73 overexpression, and/or abnormal CD73 function, such as a cancer or fibrosis. The present disclosure further provides the uses of such antibodies, the variants or antigen binding fragments thereof, in the manufacture of a medicament for the treatment of cancer.

The antibodies provided herein can also be used for detecting CD73 protein in patients or patient samples by administering the anti-CD73 antibodies, and/or their affinity variants/mutants or antigen binding fragments thereof, to patients and detecting the anti-CD73 antibody, and/or variants/mutants, or antigen binding fragments thereof, bound to the CD73 protein in a sample from the patient (e.g., in vivo or ex vivo) or by contacting the anti-CD73 antibodies, and/or variants/mutants or antigen binding fragments thereof, with samples from patients and detecting qualitatively or quantitatively the anti-CD73 antibody, and/or affinity variant/mutant or antigen binding fragment thereof, bound to the CD73 protein.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All references cited herein, including patent applications and publications, are hereby incorporated by reference in their entirety. The publications discussed herein are provided solely for their disclosure prior to the filing date of the present application. Nothing herein is to be construed as an admission that the present disclosure is not entitled to antedate such publication by virtue of prior present disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

It is understood that aspects and embodiments of the present disclosure described herein include "comprising," "consisting," and "consisting essentially of" aspects and embodiments.

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising", "comprises", "comprised of", "including", "includes", "included", "involving", "involves", "involved" and "such as" are used in their open, non-limiting sense and may be used interchangeably. Further, the term "comprising" is intended to include examples and aspects encompassed by the terms "consisting essentially of" and "consisting of". Similarly, the term "consisting essentially of" is intended to include examples encompassed by the term "consisting of".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about", it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', 'less than y', and 'less than z'. Likewise, the phrase 'about x, y, z, or greater' should be interpreted to include the specific ranges of 'about x', 'about y', and 'about z' as well as the ranges of 'greater than x', 'greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%, about 0.5% to about 2.4%, about 0.5% to about 3.2%, and about 0.5% to about 4.4%, and other possible sub-ranges) within the indicated range.

As used herein, the terms "about", "approximate", "at or about", and "substantially" mean that the amount or value in question can be the exact value or a value that provides equivalent results or effects as recited in the claims or taught herein. Reference to "about" a value or parameter herein refers to the usual error range for the respective value readily known to the skilled person in this technical field. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated±10% variation unless otherwise indicated or inferred. In general, an amount, size, formulation, parameter or other quantity or characteristic is "about", "approximate" or "at or about" whether or not expressly stated to be such. It is understood that where "about", "approximate" or "at or about" is used before a quantitative value, the parameter also keep cancer in remission or prolong a response to a specific
includes the specific quantitative value itself, unless specifi- therapy regardless of disease progression.
cally stated otherwise. That is, reference to "about" a value     The term "invasive cancer" refers to cancer that has
or parameter herein includes (and describes) aspects that are spread beyond the layer of tissue in which it started into the
directed to that value or parameter per se. For example, 5 normal surrounding tissues. Invasive cancers may or may
description referring to "about X" includes description of not be metastatic.
"X".                                                              The term "non-invasive cancer" refers to a very early
    As used herein, the terms "optional" or "optionally" cancer or a cancer that has not spread beyond the tissue of
means that the subsequently described event or circumstance origin.
can or cannot occur, and that the description includes 10     The term "progression-free survival" in oncology refers to
instances where said event or circumstance occurs and the length of time during and after treatment that a cancer
instances where it does not.                                  does not grow. Progression-free survival includes the
    As used herein, "CD73" and "CD-73" can be used inter- amount of time patients have experienced a complete
changeably, and refer to a cell surface enzyme encoded by 15 response or a partial response, as well as the amount of time
a gene in humans comprising 8 exons with a cytogenetic patients have experienced stable disease.
location of 3q13.12 and a molecular location of base pairs     The term "progressive disease" in oncology can refer to a
85,449,584-85,495,791 on chromosome 6 (Homo sapiens tumor growth of more than 20 percent since treatment
Annotation Release 109, GRCh38.p12). The CD73 protein began-either due to an increase in mass or a spread in the
is an enzyme (EC classification: 3.1.3.5) have 5'-nucleotitumor.
dase utilizing Zn 2 as a co-factor. The protein is capable of     A "disorder" is any clinical condition associated with
hydrolyzing extracellular nucleotides into membrane per- CD73 expression, CD73 overexpression, and/or abnormal
meable nucleosides and is involved in regulation of nucle- CD73 function in a subject (e.g., mammals such as humans),
obase, nucleoside, nucleotide and nucleic acid metabolism. such that the subject would benefit from treatment or pro-
It is associated with an intracellular location principally on 25 phylaxis using the disclosed anti-CD73 antibodies, variants,
the plasma membrane via a GPI-anchor. The human CD73 mutants, and/or fragments thereof, and/or pharmaceutical
protein has two described isoforms produced by alternative compositions provided herein. For example, mammals who
splicing. The canonical isoform (UniProtKB identifier suffer from or need prophylaxis against CD73 overexpres-
P21589) comprises 574 amino acids and has a molecular sion. This includes chronic and acute disorders or diseases
weight of about 63 kDa. CD73 has also been referred to as 30 including those pathological conditions which predispose
ecto-5'-nucleotidase and 5'-nucleotidase. Mutations in the the mammal to the disorder in question. Non-limiting
CD73 gene are associate with calcification of joints and examples of disorders to be treated herein include a dis-
arteries, i.e., hereditary arterial and articular multiple calci- closed cancer (such as head and neck cancer, throat cancer,
fication syndrome.                                            colorectal cancer, lung cancer, etc.) or fibrosis, including
    As used herein, "treatment" or "treating" is an approach 35 idiopathic pulmonary fibrosis.
for obtaining beneficial or desired results including clinical     "Tumor", as used herein, refers to all neoplastic cell
results. For purposes of this present disclosure, beneficial or growth and proliferation, whether malignant or benign, and
desired clinical results include, but are not limited to, one or all pre-cancerous and cancerous cells and tissues.
more of the following: alleviating one or more symptoms     The term "antibody" is used in the broadest sense and
resulting from the disease, diminishing the extent of the 40 specifically covers, for example, single monoclonal antibod-
disease, stabilizing the disease (e.g., preventing or delaying ies (including agonist, antagonist, and neutralizing antibod-
the worsening of the disease), preventing or delaying the ies), antibody compositions with polyepitopic specificity,
spread (e.g., metastasis) of the disease, preventing or delay- polyclonal antibodies, single chain anti-antibodies, and frag-
ing the recurrence of the disease, delay or slowing the ments of antibodies (see below) as long as they specifically
progression of the disease, ameliorating the disease state, 45 bind a native polypeptide and/or exhibit a biological activity
providing a remission (partial or total) of the disease, or immunological activity of this present disclosure. Accord-
decreasing the dose of one or more other medications ing to one embodiment, the antibody binds to an oligomeric
required to treat the disease, delaying the progression of the form of a target protein, e.g., a trimeric form. According to
disease, increasing or improving the quality of life, increas- another embodiment, the antibody specifically binds to a
ing weight gain, and/or prolonging survival. Also encom- protein, which binding can be inhibited by a monoclonal
passed by "treatment" is a reduction of pathological conse- antibody of this present disclosure (e.g., a deposited anti-
quence of cancer (such as, for example, tumor volume). The body of this present disclosure, etc.). The phrase "functional
methods provided herein contemplate any one or more of fragment or analog" of an antibody is a compound having a
these aspects of treatment.                                   qualitative biological activity in common with an antibody
    The terms "recurrence", "relapse" or "relapsed" refers to 55 to which it is being referred. For example, a functional
the return of a cancer or disease after clinical assessment of fragment or analog of an antibody of this invention can be
the disappearance of disease. A diagnosis of distant metas- one which can specifically bind to CD73. In one embodi-
tasis or local recurrence can be considered a relapse.        ment, the antibody can induce macrophage-mediated phago-
    The term "refractory" or "resistant" refers to a cancer or cytosis of CD73-expressing cancer cells.
disease that has not responded to treatment.              60     An "isolated antibody" is one which has been identified
    The term "adjuvant therapy" refers to treatment given and separated and/or recovered from a component of its
after the primary therapy, usually surgery. Adjuvant therapy natural environment. Contaminant components of its natural
for cancer or disease may include immune therapy, chemo- environment are materials which would interfere with diag-
therapy, radiation therapy, or hormone therapy.               nostic or therapeutic uses for the antibody, and can include
    The term "maintenance therapy" refers to scheduled 65 enzymes, hormones, and other proteinaceous or nonpro-
retreatment that is given to help maintain a previous treat- teinaceous solutes. In preferred embodiments, the antibody
ment's effects. Maintenance therapy is often given to help will be purified (1) to greater than 95% by weight of
                                                              antibody as determined by the Lowry method, and most preferably more than 99% by weight, (2) to a degree
sufficient to obtain at least 15 residues of N-terminal or
internal amino acid sequence by use of a spinning cup
sequenator, or (3) to homogeneity by SDS-PAGE under
reducing or nonreducing conditions using Coomassie blue
or, preferably, silver stain. Isolated antibody includes the
antibody in situ within recombinant cells since at least one
component of the antibody's natural environment will not be
present. Ordinarily, however, isolated antibody will be pre-
pared by at least one purification step.

The basic 4-chain antibody unit is a heterotetrameric
glycoprotein composed of two identical light (L) chains and
two identical heavy (H) chains (an IgM antibody consists of
5 of the basic heterotetramer unit along with an additional
polypeptide called J chain, and therefore contain 10 antigen
binding sites, while secreted IgA antibodies can polymerize
to form polyvalent assemblages comprising 2-5 of the basic
4-chain units along with J chain). In the case of IgGs, the
4-chain unit is generally about 150,000 daltons. Each light
(L) chain is linked to a heavy (H) chain by one covalent
disulfide bond, while the two H chains are linked to each
other by one or more disulfide bonds depending on the H
chain isotype. Each H and L chain also has regularly spaced
intrachain disulfide bridges. Each H chain has at the N-ter-
minus, a variable domain (VH) followed by three constant
domains ($C_H$) for each of α and γ chains and four $C_H$
domains for μ and ε isotypes. Each L chain has at the
N-terminus, a variable domain ($V_L$) followed by a constant
domain ($C_L$) at its other end. The $V_L$ is aligned with the $V_H$
and the $C_L$ is aligned with the first constant domain of the
heavy chain ($C_H$1). Particular amino acid residues are
believed to form an interface between the light chain and
heavy chain variable domains. The pairing of a $V_H$ and $V_L$
together forms a single antigen-binding site. For the struc-
ture and properties of the different classes of antibodies, see,
e.g., Basic and Clinical Immunology, 8th edition, Daniel P.
Stites et al., Appleton & Lange, Norwalk, CT, 1994, page 71
and Chapter 6.

The L chain from any vertebrate species can be assigned
to one of two clearly distinct types, called kappa and lambda,
based on the amino acid sequences of their constant
domains. Depending on the amino acid sequence of the
constant domain of their heavy chains ($C_H$), immunoglobu-
lins can be assigned to different classes or isotypes. There
are five classes of immunoglobulins: IgA, IgD, IgE, IgG,
and IgM, having heavy chains designated α, δ, γ, ε, and μ,
respectively. The γ and α classes are further divided into
subclasses on the basis of relatively minor differences in $C_H$
sequence and function, e.g., humans express the following
subclasses: IgG1, IgG2, IgG3, IgG4, IgA1, and IgA2.

The term "variable" refers to the fact that certain seg-
ments of the variable domains differ extensively in sequence
among antibodies. The V domain mediates antigen binding
and defines specificity of a particular antibody for its par-
ticular antigen. However, the variability is not evenly dis-
tributed across the 110-amino acid span of the variable
domains. Instead, the V regions consist of relatively invari-
ant stretches called framework regions (FRs) of 15-30 amino
acids separated by shorter regions of extreme variability
called "hypervariable regions" that are each 9-12 amino
acids long. The variable domains of native heavy and light
chains each comprise four FRs, largely adopting a beta-sheet
configuration, connected by three hypervariable regions,
which form loops connecting, and in some cases forming
part of, the beta-sheet structure. The hypervariable regions
in each chain are held together in close proximity by the FRs
and, with the hypervariable regions from the other chain, contribute to the formation of the antigen-binding site of
antibodies (see Sequences of Proteins of Immunological
Interest, 5th edition, Elvin A. Kabat et al., Public Health
Service, National Institutes of Health, Bethesda, MD, 1991).
The constant domains are not involved directly in binding an
antibody to an antigen, but exhibit various effector func-
tions, such as participation of the antibody in antibody
dependent cellular cytotoxicity (ADCC).

As used herein, the term "CDR" or "complementarity
determining region" is intended to mean the non-contiguous
antigen combining sites found within the variable region of
both heavy and light chain polypeptides. These particular
regions have been described by Kabat E A. et al., J. Biol.
Chem., 252(19): 6609-6616 (1977); Sequences of Proteins
of Immunological Interest, 5th edition, Elvin A. Kabat et al.,
Public Health Service, National Institutes of Health,
Bethesda, MD, 1991; by Chothia C. et al., J. Mol. Biol.,
196(4): 901-917 (1987); and MacCallum R M. et al., J. Mol.
Biol., 262(5): 732-745 (1996), where the definitions include
overlapping or subsets of amino acid residues when com-
pared against each other. Nevertheless, application of either
definition to refer to a CDR of an antibody or grafted
antibodies or variants thereof is intended to be within the
scope of the term as defined and used herein. The amino acid
residues which encompass the CDRs as defined by each of
the above cited references are set forth below in Table 4 as
a comparison.

TABLE 4

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

The term "monoclonal antibody" as used herein refers to
an antibody obtained from a population of substantially
homogeneous antibodies, i.e., the individual antibodies
comprising the population are identical except for possible
naturally occurring mutations that can be present in minor
amounts. Monoclonal antibodies are highly specific, being
directed against a single antigenic site. Furthermore, in
contrast to polyclonal antibody preparations which include
different antibodies directed against different determinants
(epitopes), each monoclonal antibody is directed against a
single determinant on the antigen. In addition to their
specificity, the monoclonal antibodies are advantageous in
that they can be synthesized uncontaminated by other anti-
bodies. The modifier "monoclonal" is not to be construed as
requiring production of the antibody by any particular
method. For example, the monoclonal antibodies useful in
the present disclosure can be prepared by the hybridoma
methodology first described by Kohler G. et al., Nature,
256(5517): 495-497 (1975), or can be made using recom-
binant DNA methods in bacterial, eukaryotic animal or plant
cells (see, e.g., U.S. Pat. No. 4,816,567). The "monoclonal
antibodies" can also be isolated from phage antibody librar-
ies using the techniques described in Clackson T. et al.,
Nature, 352(6336): 624-628 (1991), Marks J D. et al., J.
Mol. Biol., 222(3): 581-597 (1991), and the Examples
below, for example.

The monoclonal antibodies herein include "chimeric"
antibodies in which a portion of the heavy and/or light chain
is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this present disclosure (see U.S. Pat. No. 4,816,567; and Morrison S L. et al., *Proc. Natl. Acad. Sci. USA,* 81(21): 6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions. The constant domain (constant region) is preferably a human antibody constant region, more preferably a human IgG1, human IgG2, human IgG3 or human IgG4 antibody constant region. The particular sequence of an alternative heavy chain constant region is as shown in SEQ ID NO: 112, 113 or 114 and the particular sequence of an alternative light chain constant region is as shown in SEQ ID NO: 115.

"Antibody fragments" comprise a portion of an intact antibody, preferably the antigen binding or variable region of the intact antibody. Examples of antibody fragments include Fab, Fab', F(ab')₂, and Fv fragments; diabodies; linear antibodies (see U.S. Pat. No. 5,641,870, Example 2; Zapata G. et al., *Protein Eng.,* 8(10): 1057-1062 (1995)); single-chain antibody molecules; and multispecific antibodies formed from antibody fragments. The expression "linear antibodies" generally refers to the antibodies described in Zapata G. et al., *Protein Eng.,* 8(10): 1057-1062, 1995. Briefly, these antibodies comprise a pair of tandem Fd segments (VH-CH1-VH—CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')₂ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')₂ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

The term "Fc region-comprising polypeptide" refers to a polypeptide, such as an antibody or immunoadhesin (see definitions elsewhere herein), which comprises an Fc region. The C-terminal lysine (residue 447 according to the EU numbering system) of the Fc region may be removed, for example, during purification of the polypeptide or by recombinantly engineering the nucleic acid encoding the polypeptide. Accordingly, a composition comprising polypeptides, including antibodies, having an Fc region according to this present disclosure can comprise polypeptides populations with all K447 residues removed, polypeptide populations with no K447 residues removed or polypeptide populations having a mixture of polypeptides with and without the K447 residues.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in, for example, but not limited to, Sequences of Proteins of Immunological Interest, 5th edition, Elvin A. Kabat et al., Public Health Service, National Institutes of Health, Bethesda, MD, 1991).

"Fv" is the minimum antibody fragment which contains a complete antigen-recognition and -binding site. This fragment consists of a dimer of one heavy- and one light-chain variable region domain in tight, non-covalent association. From the folding of these two domains emanate six hyper-variable loops (3 loops each from the H and L chain) that contribute the amino acid residues for antigen binding and confer antigen binding specificity to the antibody.

However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of scFv, see A. Pluckthun, "Antibodies from *Escheri-*

*chia coli*" in The Pharmacology of Monoclonal Antibodies, vol. 113, Rosenburg and Moore eds., Springer-Verlag, New York, 1994, pp. 269-315; or Ahmad Z A. et al., *Clin. Dev. Immunol.*, 2012:980250 (2012).

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO93/11161; and Hollinger P. et al., *Proc. Natl. Acad. Sci. USA*, 90(14): 6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues.

Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region, typically that of a human immunoglobulin. For further details, see Jones P T. et al., *Nature,* 321(6069): 522-525 (1986); Riechmann L. et al., *Nature,* 332(6162): 323-329 (1988); and Presta L G, *Curr. Opin. Biotechnol.,* 3(4): 394-398 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California. The ALIGN-2 program should be compiled for use on a UNIX operating system, preferably digital UNIX V4.0D. All sequence comparison parameters are set by the ALIGN-2 program and do not vary.

The terms "Fc receptor" or "FcR" are used to describe a receptor that binds to the Fc region of an antibody. In one embodiment, an FcR of this present disclosure is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daëron M, *Annu. Rev. Immunol.,* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch J V. et al., *Annu. Rev. Immunol.,* 9:457-492 (1991); Capel P J. et al., *Immunomethods,* 4 (1): 25-34 (1994); and de Haas M. et al., *J. Lab. Clin. Med.,* 126(4): 330-341 (1995). Other FcRs, including those to be identified in the future, are encompassed by the term "FcR" herein. The term also includes the neonatal receptor, FcRn, which is responsible for the transfer of maternal IgGs to the fetus (Guyer R L. et al., *J. Immunol.,* 117(2): 587-593 (1976) and Kim J K. et al., Eur. *J. Immunol.,* 24(10): 2429-2434 (1994)).

The term "FcRn" refers to the neonatal Fc receptor (FcRn). FcRn is structurally similar to major histocompatibility complex (MHC) and consists of a α-chain noncovalently bound to β2-microglobulin. The multiple functions of the neonatal Fc receptor FcRn are reviewed in Ghetie V. et al., *Annu. Rev. Immunol.,* 18:739-766 (2000). FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton D R., *Mol. Immunol.,* 22(3): 161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. In previous reports, FcR binding was generally attributed to amino acid residues in the lower hinge region of an IgG Fc region.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain (Burton D R., *Mol. Immunol.*, 22(3): 161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, CA.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or IC50 value) than the parent polypeptide or a native sequence IgG Fc. According to some embodiments, the improvement in binding compared to a parent polypeptide is about 3-fold, preferably about 5-, 10-, 25-, 50-, 60-, 100-, 150-, 200-, up to 500-fold, or about 25% to 1000% improvement in binding. The polypeptide variant which "exhibits decreased binding" to an FcR, binds at least one FcR with lower affinity (e.g., higher apparent Kd or higher IC50 value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch J V. et al., *Annu. Rev. Immunol.*, 9:457-492 (1991). To assess ADCC activity of a molecule of interest, an in vitro ADCC assay, such as that described in U.S. Pat. No. 5,500,362 or 5,821,337 or in the Examples below may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes R. et al., *Proc. Natl. Acad. Sci. USA*, 95(2): 652-656 (1998).

The polypeptide comprising a variant Fc region which "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g. in an animal model etc. In one embodiment, the preferred variant is from about 5-fold to about 100-fold, e.g. from about 25- to about 50-fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro H. et al., *J. Immunol. Methods*, 202(2): 163-171 (1997), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference (see also, Idusogie E E. et al., *J. Immunol.*, 164(8): 4178-4184 (2000)).

An "effective amount" of an anti-CD73 antibody (or fragment thereof) or composition as disclosed herein is an amount sufficient to carry out a specifically stated purpose. An "effective amount" can be determined empirically and by known methods relating to the stated purpose. The term "therapeutically effective amount" refers to an amount of an anti-CD73 antibody (or the variant or antigen binding fragment thereof) or composition as disclosed herein, effective to "treat" a disease or disorder in a mammal (aka patient). In the case of cancer, the therapeutically effective amount of the anti-CD73 antibody (or the variant or antigen binding fragment thereof) or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-CD73 antibody (or the variant or antigen binding fragment thereof) or composition as disclosed herein can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

A "growth inhibitory amount" of an anti-CD73 antibody (or a variant or antigen binding fragment thereof) or composition as disclosed herein of this present disclosure is an amount capable of inhibiting the growth of a cell, especially tumor, e.g., cancer cell, either in vitro or in vivo. A "growth inhibitory amount" of a polypeptide, antibody, antagonist or composition of this present disclosure for purposes of inhibiting neoplastic cell growth can be determined empirically and by known methods or by examples provided herein.

A "cytotoxic amount" of an anti-CD73 antibody (or a variant or antigen binding fragment thereof) or composition of this present disclosure is an amount capable of causing the destruction of a cell, especially tumor, e.g., cancer cell, either in vitro or in vivo. A "cytotoxic amount" of an anti-CD73 antibody (or a variant or antigen binding fragment thereof) or composition of this present disclosure for purposes of inhibiting neoplastic cell growth can be determined empirically and by methods known in the art.

A "growth inhibitory amount" of an anti-CD73 antibody (or a variant or antigen binding fragment thereof) or composition of this present disclosure is an amount capable of inhibiting the growth of a cell, especially tumor, e.g., cancer cell, either in vitro or in vivo. A "growth inhibitory amount" of an anti-CD73 antibody (or a variant or antigen binding fragment thereof) or composition of this present disclosure for purposes of inhibiting neoplastic cell growth can be determined empirically and by known methods or by examples provided herein.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "detecting" is intended to include determining the presence or absence of a substance or quantifying the amount of a substance (such as CD73). The term thus refers to the use of the materials, compositions, and methods of the present disclosure for qualitative and quantitative determinations. In general, the particular technique used for detection is not critical for practice of the present disclosure.

For example, "detecting" according to the present disclosure may include: observing the presence or absence of CD73 gene product, mRNA molecules, or a CD73 polypeptide; a change in the levels of a CD73 polypeptide or amount bound to a target; a change in biological function/activity of a CD73 polypeptide. In some embodiments, "detecting" may include detecting wild type CD73 levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

Anti-CD73 Antibodies and Affinity Variants/Mutants

The present disclosure pertains to antibodies that bind CD73 receptor as disclosed herein. The disclosed anti-CD73 antibodies, and their affinity variants and/or mutants, or antigen binding fragments thereof, can be used in a variety of therapeutic and diagnostic methods. An anti-CD73 antibody is an antibody that binds to CD73 with sufficient affinity and specificity. In some embodiments, a disclosed anti-CD73 antibody (or the variant or mutant or antigen-binding fragment thereof) can be used as a therapeutic agent in targeting and interfering with diseases or conditions associated with the expression of CD73. In various aspects, a disclosed anti-CD73 antibody (or the variant/mutant or antigen binding fragment thereof) will show minimal binding to other proteins. In some instances, it is preferred that the disclosed anti-CD73 antibody (or the variant/mutant or antigen binding fragment thereof) be a human or recombinant humanized anti-CD73 monoclonal antibody.

Without wishing to be bound by a particular theory, it is believed that the disclosed anti-CD73 antibodies, and their affinity variants and/or mutants, or antigen binding fragments thereof can increase internalization of CD73 in cells expressing CD73, thus leading to a decrease in the amount of CD73 protein at the plasma membrane on cells to which the disclosed anti-CD73 antibodies, and their affinity variants and/or mutants, or antigen binding fragments thereof bind. Accordingly, a decrease in the amount of CD73 protein at the plasma membrane would be associated with a decrease in 5'-nucleotidase activity associated with CD73. In some aspects, it is believed, again without wishing to be bound by a particular theory, that a decrease in CD73-associated 5'-nucleotidase activity via increased internalization can decrease tumor cell proliferation via enhanced immunocell function at tumor sites due to decreased 5'-nucleotidase activity.

As disclosed herein, the disclosed anti-CD73 antibodies, and their affinity variants and/or mutants, or antigen binding fragments are believed to have a beneficial effect in other clinical conditions associated with CD73 expression, e.g., fibrosis, including idiopathic pulmonary fibrosis. Without wishing to be bound by a particular theory, it is believed that in other such clinical conditions, the disclosed anti-CD73 antibodies, and their affinity variants and/or mutants, or antigen binding fragments can have a positive clinical benefit for a patient with, e.g., fibrosis, including idiopathic pulmonary fibrosis, due to decreased CD73 protein (and commensurately, decreased 5'-nucleotidase activity) of appropriate cells expressing CD73.

According to certain embodiments, the anti-CD73 antibody comprises the CDRs, the variable heavy chain region, and/or the variable light chain region of any one of the antibodies disclosed herein.

The present disclosure provides anti-CD73 antibodies, their affinity variants/mutants, and/or antigen binding fragments thereof. In certain embodiments, a particular anti-CD73 antibody, its affinity variant(s)/mutant(s), and/or antigen binding fragment(s) thereof, of the present disclosure, comprise a light chain (LC) variable domain sequence which comprises specific CDR-L1, CDR-L2 and CDR-L3 sequences as set forth in Table 1 above, and a heavy chain (HC) variable domain sequence which comprises specific CDR-H1, CDR-H2 and CDR-H3 sequences as set forth in Table 2 above. The nucleic acid and its amino acid sequence of each light chain and heavy chain of each particular anti-CD73 antibody, its affinity variant(s)/mutant(s), and/or antigen binding fragment(s) thereof, of the present disclosure, are also provided in the Sequence Listing below. The present disclosure provides that the heavy and light chain variable domains and CDRs noted herein are combined in all possible pair-wise combinations to generate a number of anti-CD73 antibodies, and their affinity variant(s)/mutant(s), and/or antigen binding fragment(s) thereof.

In certain embodiments, the amino acid substitution(s) are conservative amino acid substitution(s). In certain embodiments, the amino acid substitutions do not substantially reduce the ability of the antibody to bind antigen. For example, conservative alterations may be made (e.g., conservative substitutions as provided herein) that do not substantially reduce binding affinity of the disclosed antibodies to the target CD73. The binding affinity of anti-CD73 antibody variants can be assessed using methods described in the Examples below.

Conservative substitutions are shown in Table 5 under the heading of "conservative substitutions." More substantial changes are provided in Table 5 under the heading of "exemplary substitutions," and as further described below in reference to amino acid side chain classes. Amino acid substitutions may be introduced into an antibody of interest and the products screened for a desired activity, e.g., retained/improved CD73 binding, decreased immunogenicity, or improved ADCC or CDC.

TABLE 5

CONSERVATIVE SUBSTITUTIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Non-conservative substitutions will entail exchanging a member of one of these classes for another class. An exemplary substitutional variant is an affinity matured antibody, which may be conveniently generated, e.g., using phage display based affinity maturation techniques such as those described herein. Briefly, one or more CDR residues are mutated and the variant antibodies displayed on phage and screened for a particular biological activity (e.g. binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom H R, *Methods Mol. Biol.,* 178:1-37 (2002); Antibody Phage Display, Philippa O'Brien, R. A., Humana Press, Totowa, NJ, 2001.

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling.

In certain embodiments, the anti-CD73 antibody, the variant or mutant, or antigen binding fragment thereof, may lack an N-glycosylation motif in the heavy chain or light chain variable region which can cause differences within a batch of antibodies resulting in altered function, immunogenicity, or stability. Methods of analyzing antibody glycosylation include, but are not limited to, e.g., chromatography (such as cation exchange chromatography (CEX) or liquid chromatography), mass spectrometry (such as electrospray ionization mass spectrometry), and capillary electrophoresis-sodium dodecyl sulfate. Such methods are described in, e.g., Jung S T. et al., *Curr. Opin. Biotechnol.,* 22(6): 858-67 (2011); Cummings R D, Etzler M E. Antibodies and Lectins in Glycan Analysis. In: Varki A, Cummings R D, Esko J D, et al., editors. Essentials of Glycobiology. 2nd edition. Cold Spring Harbor (NY): Cold Spring Harbor Laboratory Press; 2009. Chapter 45; Mulloy B, Hart G W, Stanley P. Structural Analysis of Glycans. In: Varki A, Cummings R D, Esko J D, et al., editors. Essentials of Glycobiology. 2nd edition. Cold Spring Harbor (NY): Cold Spring Harbor Laboratory Press; 2009. Chapter 47; Leymarie N. et al., *Anal. Chem.,* 84(7): 3040-3048 (2012); Fernandez D D., *European Biopharmaceutical Review,* pp 106-110 (2005); and Raju T S, *Methods Mol. Biol.,* 988:169-180 (2013).

In certain embodiments, a mutant of a particular anti-CD73 antibody comprises one or more mutations at the N-glycosylation sites in one or more CDR regions, e.g., the sequon N—X—S/T. The anti-CD73 antibody mutant with one or more mutant at the N-glycosylation sites eliminates the N-glycosylation site but remains the equal function.

In certain embodiments, the anti-CD73 antibodies, the variants and/or mutants, or antigen binding fragments thereof, have a stronger binding affinity for CD73 than they have for a homologue of that CD73. Normally, an anti-CD73 antibody, and/or the variant or antigen binding fragment thereof, "binds specifically" to CD73 (i.e., has a binding affinity (Kd) value of no more than about $1\times10^{-7}$ M, preferably no more than about $1\times10^{-8}$ and most preferably no more than about $1\times10^{-9}$ M) but has a binding affinity for non-CD73 which is at least about 50-fold, or at least about 500-fold, or at least about 1000-fold weaker than its binding affinity for CD73. The anti-CD73 antibody that binds specifically to CD73 can be of any of the various types of antibodies as defined above, but preferably is a humanized or human antibody.

In some embodiments, the extent of binding of the anti-CD73 antibody to a non-target protein is less than about 10% of the binding of the antibody to CD73 as determined by methods known in the art, such as ELISA, fluorescence activated cell sorting (FACS) analysis, or radioimmunoprecipitation (RIA). Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., such as an anti-CD73 antibody and/or an affinity variant described herein). In some embodiments, the anti-CD73 antibody and/or the affinity variant exhibits similar antibody-dependent cell-mediated cytotoxicity (ADCC) effector function as the reference anti-CD73 monoclonal antibodies, as demonstrated by, e.g., assays described in the Examples.

For example, in certain embodiments, ADCC effector function activity of an anti-CD73 antibody and/or its affinity variant or mutant described herein is at least about 80%, at least about 85%, at least about 90%, at least about 91%, at least about 92%, at least about 93%, at least about 94%, at least about 95%, at least about 96%, at least about 97%, at least about 98%, at least about 99%, at least about 100%, or more than 100% (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or about 130%) of the ADCC effector function activity of the reference anti-CD73 antibody including any range between these values.

In certain embodiments, the anti-CD73 antibody, and/or its affinity variant or mutant thereof, exhibits similar binding affinity for CD73 as the reference anti-CD73 antibody. In certain embodiments, binding to CD73 is demonstrated by ELISA, as described in the Examples. For example, the binding affinity of the anti-CD73, and/or its affinity variant or mutant thereof, for CD73 is about 1%, about 5%, about 10%, about 15%, about 20%, about 30%, about 40%, about 50%, about 60%, about 70%, about 80%, about 90%, about 95%, about 96%, about 97%, about 98%, about 99%, about 100%, or more than 100% higher (e.g., about 105%, about 106%, about 107%, about 108%, about 109%, about 110%, about 111%, about 112%, about 113%, about 114%, about 115%, about 116%, about 117%, about 118%, about 119%, about 120%, about 121%, about 122%, about 123%, about 124%, about 125%, or more than about 125%) than the binding affinity of the reference anti-CD73 antibody for CD73.

In certain embodiments, the anti-CD73 antibody, and/or its affinity variant or mutant thereof, binds a human CD73 with a Kd between about 0.1 pM to 200 pM (0.2 nM), e.g., about 0.1 pM, about 0.25 pM, about 0.5 pM, about 0.75 pM, about 1 pM, about 5 pM, about 10 pM, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, about 150 pM, about 160 pM, about 170 pM, about 180 pM, about 190 pM, or more than about 190 pM, including any range between these values. In certain embodiments, the binding affinity of the anti-CD73 antibody, and/or its affinity variant or mutant thereof, to CD73 is about 1%, about 5%, about 10%, about 15%, about 20%, about 30%, about 40%, about 50%, about 60%, about 70%, about 80%, about 90%, about 95%, about 96%, about 97%, about 98%, about 99%, about 100%, or more than about 100% higher (e.g., about 105%, about 110%, about 120%, or about 130%) than the binding affinity of the reference anti-CD73 antibody to CD73. In certain embodiments, the binding affinity of the anti-CD73, and/or its variant or mutant thereof, to CD73 is about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.25-fold, about 2.5-fold, about 2.75-fold, about 3-fold, about 3.25-fold, about 3.5-fold, about 3.75-fold, about 4-fold, about 4.25-fold, about 4.5-fold, about 4.75-fold, or more than about 4.75-fold higher than the binding affinity of the reference anti-CD73 antibody to CD73, including any range in between these values.

In certain embodiments, the anti-CD73 antibody, and/or its variant or mutant thereof, provided herein have prolonged in vivo half-lives as compared to the reference anti-CD73 antibody. In certain embodiments, the in vivo half-life of an anti-CD73 antibody, and/or its variant or mutant thereof, described herein is no shorter than the in vivo half-life of the reference anti-CD73 antibody.

In certain embodiments, the anti-CD73 antibody, and/or its variant or mutant thereof, provided herein exhibit pharmacokinetic properties that are similar to those of the reference anti-CD73 antibodies. In certain embodiments, the anti-CD73 antibody, and/or its variant or mutant thereof provided herein exhibit an AUC (area under curve) that is about 50%, about 55%, about 60%, about 65%, about 70%, about 75%, about 80%, about 85%, about 90%, about 95%, or greater than 95% (such as about 96%, about 97%, about 98%, about 99%, or more than about 99%) of the serum concentration-time profiles of the reference anti-CD73 antibody, including any range between these values.

In certain embodiments, the anti-CD73 antibody, and/or its variant or mutant thereof, of the present disclosure comprises an Fc sequence of a human IgG, e.g., human IgG1 or human IgG4. In certain embodiments, the Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function. For example, WO00/42072 and Shields et al. *J Biol. Chem.* 9(2): 6591-6604 (2001) describes antibody variants with improved or diminished binding to FcRs. The contents of those publications are specifically incorporated herein by reference. The anti-CD73 antibody, and/or its variant or mutant thereof, of the present disclosure can be in the form of a Fab, Fab', a F(ab')$_2$, single-chain Fv (scFv), an Fv fragment; a diabody and a linear antibody. Also, the anti-CD73 antibody, and/or its variant or mutant thereof, of the present disclosure can be a multispecific antibody, and/or variant or mutant thereof that binds to CD73, but also binds to one or more other targets and inhibits their function(s). The anti-CD73 antibody, and/or its variant or mutant thereof, of the present disclosure can be conjugated to a therapeutic agent (e.g., cytotoxic agent, a radioisotope and a chemotherapeutic agent) or a label for detecting CD73 in patient samples or in

| vivo by imaging (e.g., radioisotope, fluorescent dye and enzyme). Other modifications include the conjugation of toxins to anti-CD73 antibodies, and/or variants or mutants thereof, are also provided herein.

Nucleic acid molecules encoding the anti-CD73 antibodies, and/or their variants and/or mutants thereof, and the expression vectors comprising nucleic acid molecules encoding the CDRs and/or the heavy chain variable domain and/or a light chain variable domain are also described herein, and cells comprising the nucleic acid molecules are also contemplated. The anti-CD73 antibody, and/or its variant or mutant thereof, of the present disclosure can be used in the therapies described herein and to detect CD73 protein in patient samples (e.g., via FACS, immunohistochemistry (IHC), ELISA assays) or in patients.

Monoclonal Antibodies

Monoclonal antibodies can be prepared, e.g., using hybridoma methods, such as those described by Kohler G. et al., *Nature,* 174(5): 2453-2455 (2005) or can be made by recombinant DNA methods (U.S. Pat. No. 4,816,567) or can be produced by the methods described herein in the Examples below. In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro.

The immunizing agent will typically include a polypeptide or a fusion protein of the protein of interest or a composition comprising the protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Monoclonal Antibodies: principles and practice, James W. Goding, New York: Academic Press, 1986, pp. 59-103). Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies (Kozbor D. et al., *J. Immunol.,* 133(6): 3001-3005 (1984); Monoclonal Antibody Production Techniques and Applications, Brodeur et al., Marcel Dekker, Inc.: New York, 1987, pp. 51-63).

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson P J. et al., *Anal. Biochem.,* 107(1): 220-239 (1980).

After the desired hybridoma cells are identified, the clones can be sub cloned by limiting dilution procedures and grown by standard methods (Monoclonal Antibodies: principles and practice, James W. Goding, New York: Academic Press, 1986, pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods known in the art and/or later developed. DNA encoding the monoclonal antibodies provided herein can be readily isolated and sequenced using conventional procedures (e.g., by using oligonucleotide probes that are capable of binding specifically to genes encoding the heavy and light chains of murine antibodies). The hybridoma cells provided herein serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (e.g., Morrison et al., supra) or by covalently joining to the immunoglobulin coding sequence all or part of the coding sequence for a nonimmunoglobulin polypeptide. Such a non-immunoglobulin polypeptide can be substituted for the constant domains of an antibody provided herein, or can be substituted for the variable domains of one antigen-combining site of an antibody provided herein to create a chimeric bivalent antibody.

In certain embodiments, an anti-CD73 antibody and/or its variant or mutant thereof provided by the present disclosure is expressed by a stable mammalian cell line. In certain embodiments, an anti-CD73 antibody and/or its variant or mutant thereof provided by the present disclosure is expressed from a stable mammalian cell line at a titer of about 2.0 grams/liter, about 2.5 grams/liter, about 3.0 grams/liter, about 3.5 grams/liter, about 4.0 grams/liter, about 4.5 grams/liter, about 5.0 grams/liter, about 5.5 grams/liter, about 6.0 grams/liter, about 6.5 grams/liter, about 7.0 grams/liter, or more than about 7.0 grams/liter, including any range in between these values. In certain embodiments, the stable mammalian cell line from which an anti-CD73 antibody and/or its variant or mutant thereof provided by the present disclosure is expressed is a CHO cell line.

In certain embodiments, the antibodies are monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using, but not limited to, techniques known in the art.

Human and Humanized Antibodies

The anti-CD73 antibody, and/or its variant or mutant thereof, of the present disclosure are human antibodies. They can be humanized antibodies, as well. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin (e.g., Jones P T. et al., *Nature,* 321(6069): 522-525 (1986); Riechmann L. et al., *Nature,* 332(6162): 323-327 (1988); Presta L G, *Curr. Opin. Biotechnol.,* 3(4): 394-398 (1992)).

Generally, a humanized antibody has one or more amino acid residues introduced into it from a source that is non-human. These non-human amino acid residues are often referred to as "import" residues, which are typically taken from an "import" variable domain. According to one embodiment, humanization can be essentially performed following the method of Winter and co-workers (Jones P T. et al., *Nature,* 321(6069): 522-525 (1986); Riechmann L. et al., *Nature,* 332(6162): 323-327 (1988); Verhoeyen M. et al., *Science,* 239(4847): 1534-1536 (1988)), by substituting rodent CDRs or CDR sequences for the corresponding sequences of a human antibody. Accordingly, such "humanized" antibodies are antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production.

Transfer of the human germ-line immunoglobulin gene array into such germ-line mutant mice will result in the production of human antibodies upon antigen challenge, see e.g., Jakobovits A. et al., *Proc. Natl. Acad. Sci. USA,* 90(6): 2551-2555 (1993); Jakobovits A. et al., *Nature,* 362(6417): 255-258 (1993); Bruggemann M. et al., *Year Immunol.,* 7:33-40 (1993); U.S. Pat. Nos. 5,545,806, 5,569,825, 5,591, 669; 5,545,807; and WO97/17852.

Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is known in the art, for example, see Marks J D. et al., *Biotechnology,* 10(7): 779-783 (1992); Lonberg N. et al., *Nature,* 368(6474): 856-859 (1994); Morrison S L., *Nature,* 368(6474): 812-813 (1994); Fishwild D M. et al., *Nat. Biotechnol.,* 14(7): 845-851 (1996); Neuberger M., *Nat. Biotechnol.,* 14(7): 826 (1996); Lonberg N. et al., *Int. Rev. Immunol.,* 13(1): 65-93 (1995).

Alternatively, phage display technology (McCafferty J. et al., *Nature,* 348(6301): 552-554, 1990) can be used to produce human antibodies and antibody fragments in vitro, from immunoglobulin variable (V) domain gene repertoires from unimmunized donors. According to one embodiment of this technique, antibody V domain sequences are cloned in frame into either a major or minor coat protein gene of a filamentous bacteriophage, such as M13 or fd, and displayed as functional antibody fragments on the surface of the phage particle. Phage display can be performed in a variety of formats, e.g., as described below in the Examples section or as reviewed in, e.g., Johnson K S. et al., *Curr. Opin. Struct. Biol.,* 3(4): 564-571 (1993). Several sources of V-gene segments can be used for phage display. Clackson T. et al., *Nature,* 352(6336): 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks J D. et al., *J. Mol. Biol.,* 222(3): 581-597 (1991), or Griffith A D. et al., *EMBO J.* 12(2): 725-734 (1993). See, also, U.S. Pat. Nos. 5,565,332 and 5,573,905.

As discussed above, human antibodies may also be generated by in vitro activated B cells using the methods known in the art.

Human antibodies can also be produced using various techniques known in the art, including phage display libraries. Hoogenboom H R. et al., *J. Mol. Biol.,* 227(2): 381-388 (1991); Marks J D. et al., *J. Mol. Biol.,* 222(3): 581-597 (1991). The techniques of Cole et al. and Boerner et al. are also available for the preparation of human monoclonal antibodies (Monoclonal Antibodies and Cancer Therapy, Cole et al., Alan Liss, Inc., 1985, pp. 77 and Boerner P. et al., *J. Immunol.,* 147(1): 86-95 (1991)).

Multispecific Antibodies

Multispecific antibodies are monoclonal, preferably human or humanized, antibodies that have binding specificities for two or more different antigens (e.g., bispecific antibodies have binding specificities for at least two antigens). For example, one of the binding specificities can be for the a5~1 protein, the other one can be for any other antigen. According to one preferred embodiment, the other antigen is a cell-surface protein or receptor or receptor subunit. For example, the cell-surface protein can be a natural killer (NK) cell receptor. Thus, according to one embodiment, a bispecific antibody of this present disclosure can bind both CD73 and, e.g., a second cell surface receptor.

Suitable methods for making bispecific antibodies are well known in the art. For example, the recombinant production of bispecific antibodies is based on the co-expression of two immunoglobulin heavy-chain/light-chain pairs, where the two heavy chains have different specificities (Milstein C et al., *Nature,* 305(5934): 537-540 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in the art, e.g., in WO93/08829 and in Traunecker A. et al., *EMBO J.,* 10(12): 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh M R. et al., *Methods Enzymol.,* 121:210-228 (1986).

Various techniques for making and isolating bispecific antibody fragments directly from recombinant cell culture have also been described. For example, bispecific antibodies have been produced using leucine zippers (Kostelny S A. et al., *J. Immunol.,* 148(5): 1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger P. et al., *Proc. Natl. Acad. Sci. USA,* 90(14): 6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber M. et al., *J. Immunol.,* 152(11): 5368-5374 (1994).

Antibodies with more than two valencies are contemplated. For example, trispecific antibodies can be prepared (Tutt A. et al., *J. Immunol.,* 147(1) 60-69 (1991)).
Heteroconjugate Antibodies Heteroconjugate antibodies are composed of two covalently joined antibodies. Such antibodies have, for example, been proposed to target immune-system cells to unwanted cells, and for treatment of HIV infection. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercapto-butyrimidate and those known in the art.
Effector Function Engineering It can be desirable to modify the antibody provided herein with respect to effector function, so as to enhance, e.g., the effectiveness of the antibody in treating cancer. For example, cysteine residue(s) can be introduced into the Fc region, thereby allowing inter-chain disulfide bond formation in this region. The homodimeric antibody thus generated can have improved internalization capability and/or increased complement-mediated cell killing and antibody-dependent cellular cytotoxicity (ADCC). See, Caron P C. et al., *J. Exp. Med.,* 176(4): 1191-1195 (1992) and Shopes B., *J. Immunol.,* 148(9): 2918-2922 (1992). Homodimeric antibodies with enhanced anti-tumor activity can also be prepared using heterobifunctional cross-linkers known in the art. Alternatively, an antibody can be engineered that has dual Fc regions and can thereby have enhanced complement lysis and ADCC capabilities. See, e.g., Stevenson G T. et al., *Anticancer Drug Des.,* 3(4): 219-230 (1989).

Mutations or alterations in the Fc region sequences can be made to improve FcR binding (e.g., FcγR, FcRn). According to one embodiment, an antibody of this invention has at least one altered effector function selected from the group consisting of ADCC, CDC, and improved FcRn binding compared to a native IgG or a parent antibody. Examples of several useful specific mutations are described in, e.g., Shields R L. et al., *J. Biol. Chem.,* 276(6): 6591-6604 (2001); Presta, L G. et al., *Biochem. Soc. Trans.* 30(4): 487-490 (2002); and WO00/42072.

According to one embodiment, the Fc receptor mutation is a substitution at least one position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439 of the Fc region, wherein the numbering of the residues in the Fc region is according to the EU numbering system. In some embodiments, the Fc receptor mutation is a D265A substitution. In some embodiments, the Fc receptor mutation is a N297 A substitution. Additional suitable mutations are known in the art, e.g., as set forth in U.S. Pat. No. 7,332,581.
Immunoconjugates The present disclosure also pertains to immunoconjugates comprising an antibody, or variant or mutant thereof, conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$B, $^{131}$I, $^{131}$In, $^{90}$Y, and $^{186}$Re. Exemplary chemotherapeutic agents useful in the generation of such immunoconjugates include those described elsewhere herein.

In certain embodiments, an anti-CD73 antibody, and/or its variant or mutant thereof, of the present disclosure is conjugated to maytansine, a maytansinoid, or calicheamicin. In certain embodiments, an anti-CD73 antibody, and/or its variant or mutant thereof, of the present disclosure is conjugated to the maytansinoid DM1.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bisdiazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta E S. et al., *Science,* 238(4830): 1098-1104 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In certain embodiments, an anti-CD73 antibody, and/or its variant or mutant thereof, of the present disclosure can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Covalent Modifications

Covalent modifications of the anti-CD73 antibodies, variants, mutants, and fragments thereof are included within the scope of this present disclosure. One type of covalent modification includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide to a water-insoluble support matrix or surface for use in the method for purifying antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)-dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the $\alpha$-amino groups of lysine, arginine, and histidine side chains (Proteins: Structure and Molecular Properties, Thomas E. Creighton, W. H. Freeman & Co., San Francisco, 1983, pp. 79-86), acetylation of the N-terminal amine, and amidation of any C-terminal carboxyl group.

Another type of covalent modification of the polypeptide comprises linking the polypeptide to one of a variety of nonproteinaceous polymers, e.g., polyethylene glycol (PEG), polypropylene glycol, or polyoxyalkylenes, in the manner known in the art, e.g., set forth in U.S. Pat. Nos. 4,640,835; 4,496,689; 4,301,144; 4,670,417; 4,791,192 or 4,179,337.

Chimeric Molecules

The anti-CD73 antibody, and/or its variant or mutant thereof, of the present disclosure can also be modified if advantageous in a way to form a chimeric molecule comprising the polypeptide fused to another, heterologous polypeptide or amino acid sequence (e.g., immunoadhesins or peptibodies).

In one embodiment, such a chimeric molecule comprises a fusion of the polypeptide with a protein transduction domain which targets the polypeptide for delivery to various tissues and more particularly across the brain blood barrier, using, for example, the protein transduction domain of human immunodeficiency virus TAT protein (Schwarze S R. et al., *Science,* 285(5433): 1569-1572 (1999)).

In certain embodiments, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-gly) tags; the flu HA tag polypeptide and its antibody 12CA5 (Field J. et al., *Mol. Cell. Biol.,* 8(5): 2159-2165 (1988)); the c-myc tag and the 8F9, 3C7, 6E10, G4, B7 and 9E10 antibodies thereto (Evan G I. et al., *Mol. Cell. Biol.,* 5(12): 3610-3616 (1985)); and the Herpes Simplex virus glycoprotein D (gD) tag and its antibody (Paborsky L R. et al., *Protein Eng.,* 3(6): 547-553 (1990)). Other tag polypeptides include the Flag-peptide (Hopp T P. et al., *Bio/Technology,* 6:1204-1210 (1988)); the KT3 epitope peptide (Martin G A. et al., *Science,* 255(5041): 192-194 (1992)); an $\alpha$-tubulin epitope peptide (Skinner M P. et al., *J. Biol. Chem.,* 266(9): 15163-15166 (1991)); and the T7 gene 10 protein peptide tag (Lutz-Freyermuth C. et al., *Proc. Natl. Acad. Sci. USA,* 87(16): 6393-6397 (1990)).

In an alternative embodiment, the chimeric molecule can comprise a fusion of the polypeptide with an immunoglobulin or a particular region of an immunoglobulin. For a bivalent form of the chimeric molecule (e.g., an "immunoadhesin"), such a fusion could be to the Fc region of an IgG molecule. Ig fusions of this present disclosure include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. The production of immunoglobulin fusions are known in the art, see e.g., U.S. Pat. No. 5,428,130.

Immunoliposomes

The anti-CD73 antibody, and/or its variant or mutant thereof, of the present disclosure can also be formulated as immunoliposomes. Liposomes containing the antibody are prepared by methods known in the art, such as described in Epstein D A. et al., *Proc. Natl. Acad. Sci. USA,* 82(11): 3688-3692 (1985); Hwang K J. et al., *Proc. Natl. Acad. Sci. USA,* 77(7): 4030-4034 (1980); and U.S. Pat. Nos. 4,485, 045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin F J. et al., *J. Biol. Chem.*, 257(1): 286-288 (1982) via a disulfide-interchange reaction. An antineoplastic agent, a growth inhibitory agent, or a chemotherapeutic agent (such as doxorubicin) is optionally also contained within the liposome. See, Gabizon A. et al., *J. Natl. Cancer Inst.*, 81(19): 1484-1488 (1989).

Treatment Using Anti-CD73 Antibodies, Variant or Mutant Thereof

The disclosed anti-CD73 antibodies, variants, mutants, and/or fragments thereof, and/or pharmaceutical compositions provided herein, can be administered to subjects (e.g., mammals such as humans) to treat a disease, disorder, or clinical condition associated with CD73 expression, CD73 overexpression, or abnormal CD73 function. For example, a cancer associated with expression of CD73 can be, but is not limited to, such as lymphoma, kidney cancer, lung cancer, colon cancer, hepatoma, stomach cancer, primary effusion lymphoma, osteosarcoma, and non-Hodgkin lymphoma. A further example of disease, disorder, or clinical condition associated with CD73 expression can be fibrosis, including idiopathic pulmonary fibrosis. In certain embodiments, the present disclosure provides anti-CD73 antibodies and/or variants/mutants described herein (or fragments thereof) for use in the manufacture of a medicament for the treatment of a cancer or fibrosis in a subject. In certain embodiments, the subject to be treated is a mammal (e.g., human, non-human primate, rat, mouse, cow, horse, pig, sheep, goat, dog, cat, etc.). In certain embodiments, the subject is a human. In certain embodiments, the subject is a clinical patient, a clinical trial volunteer, an experimental animal, etc. In certain embodiments, the subject is suspected of having or at risk for having a cancer or fibrosis.

In some embodiments, the disclosed anti-CD73 antibodies, variants, mutants, and/or fragments thereof, and/or pharmaceutical compositions provided herein, can be administered to subjects (e.g., mammals such as humans) to treat a cancer recurrence or relapse for a cancer associated with CD73 expression.

In some embodiments, the disclosed anti-CD73 antibodies, variants, mutants, and/or fragments thereof, and/or pharmaceutical compositions provided herein, can be administered to subjects (e.g., mammals such as humans) to treat a refractory or resistant cancer associated with CD73 expression.

In some embodiments, the disclosed anti-CD73 antibodies, variants, mutants, and/or fragments thereof, and/or pharmaceutical compositions provided herein, can be administered to subjects (e.g., mammals such as humans) to provide adjuvant therapy for a cancer associated with CD73 expression.

In some embodiments, the disclosed anti-CD73 antibodies, variants, mutants, and/or fragments thereof, and/or pharmaceutical compositions provided herein, can be administered to subjects (e.g., mammals such as humans) to provide maintenance therapy for a cancer associated with CD73 expression.

In some embodiments, the disclosed anti-CD73 antibodies, variants, mutants, and/or fragments thereof, and/or pharmaceutical compositions provided herein, can be administered to subjects (e.g., mammals such as humans) to treat an invasive cancer associated with CD73 expression.

In some embodiments, the disclosed anti-CD73 antibodies, variants, mutants, and/or fragments thereof, and/or pharmaceutical compositions provided herein, can be administered to subjects (e.g., mammals such as humans) to treat a non-invasive cancer associated with CD73 expression.

In some embodiments, the disclosed anti-CD73 antibodies, variants, mutants, and/or fragments thereof, and/or pharmaceutical compositions provided herein, can be administered to subjects (e.g., mammals such as humans) to increase the progression-free survival to a subject diagnosed with a cancer associated with CD73 expression.

In some embodiments, the cancer associated with CD73 expression that can be treated using the disclosed anti-CD73 antibodies, variants, mutants, and/or fragments thereof can be multi-drug resistant (MDR) or drug-sensitive. Examples of cancer include but are not limited to, carcinoma, lymphoma, blastoma, sarcoma, hematological cancer, and leukemia. In some embodiments, the cancers associated with CD73 expression, that can be treated using the disclosed anti-CD73 antibodies, variants, mutants, and/or fragments thereof, include, but are not limited, a colorectal cancer, ovarian cancer, gastric cancer, gallbladder cancer, leukemia, chronic lymphoblastic leukemia (CLL), acute lymphoblastic leukemia (ALL), prostate cancer, melanoma, breast cancer, triple negative breast cancer (TNBC), bladder cancer, non-small cell lung cancer (NSCLC), pancreatic cancer, glioma cancer, head and neck cancer, thyroid cancer, B-cell acute lymphoblastic leukemia, medulloblastoma, atypical teratoid/rhabdoid cancer, and oral cavity squamous cell cancer. In further embodiments, the cancers associated with CD73 expression, that can be treated using the disclosed anti-CD73 antibodies, variants, mutants, and/or fragments thereof, include, but are not limited, a cancer of the blood (or hematopoietic tissue), bladder, brain, breast (e.g., triple-negative breast cancer, TNBC), central and peripheral nervous system, cervix, colon, head and neck, kidney, liver, lung, including small cell lung cancer, esophagus, gall bladder, gastrointestinal tract, genitourinary tract, hematopoietic tumors of lymphoid lineage lymphatic system, hematopoietic tumors of myeloid lineage, ovary, pancreas, rectum, stomach, prostate, skin, including squamous cell carcinoma, and thyroid.

In some embodiments, the cancer associated with CD73 expression that can be treated using the disclosed anti-CD73 antibodies, variants, mutants, and/or fragments thereof can be a hematological cancer. In a still further aspect, the hematological cancer is selected from a leukemia, myeloma, or lymphoma, including, but not limited to, acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, classical Hodgkin's lymphoma (cHL), Non-Hodgkin lymphoma primary mediastinal B-Cell lymphoma (NHL PMBCL), Non-Hodgkin lymphoma, multiple myeloma, solitary myeloma, localized myeloma, extramedullary myeloma, small lymphocytic lymphoma, B-cell non-Hodgkin lymphoma, and large B-cell lymphoma. Exemplary hematopoietic tumors of lymphoid lineage include, but are not limited to, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma. Hematopoietic tumors of myeloid lineage include, but are not limited to, acute and chronic myelogenous leukemias, myelodysplastic syndrome and promyelocytic leukemia; tumors of mesenchymal origin, including fibrosarcoma and rhabdomyosarcoma.

In other embodiments, the cancer associated with CD73 expression that can be treated using the disclosed anti-CD73 antibodies, variants, mutants, and/or fragments thereof can be a cancer of the brain or central nervous system. Tumors of the central and peripheral nervous system include, but are not limited to, astrocytoma, neuroblastoma, glioma and schwannomas. Further exemplary cancers of the brain or center nervous system include glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopericytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytoma, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

Other exemplary tumors associated with CD73 expression that can be treated using the disclosed anti-CD73 antibodies, variants, mutants, and/or fragments thereof include, but are not limited to, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, osteosarcoma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, melanoma, teratocarcinoma, xenoderoma pigmentosum, keratoacanthoma, thyroid follicular cancer and Kaposi's sarcoma.

Many diagnostic methods for cancer (such as melanoma, NSCLC, head and neck cancer, urothelial cancer, breast cancer (e.g., triple-negative breast cancer, TNBC), gastric cancer, classical Hodgkin's lymphoma (cHL), Non-Hodgkin lymphoma primary mediastinal B-Cell lymphoma (NHL PMBCL), mesothelioma, ovarian cancer, lung cancer (e.g., small-cell lung cancer), esophageal cancer, nasopharyngeal carcinoma (NPC), biliary tract cancer, colorectal cancer, cervical cancer, thyroid cancer) or any other disease exhibiting abnormal CD73 function and the clinical delineation of those diseases are known in the art. Such methods include, but are not limited to, e.g., immunohistochemistry, PCR, fluorescent in situ hybridization (FISH). Additional details regarding diagnostic methods for abnormal CD activity or expression are described in the art.

The disclosed anti-CD73 antibody and/or variant or mutant (or fragment thereof) and/or pharmaceutical compositions provided herein can be administered by any suitable route including, e.g., intravenous, intramuscular, or subcutaneous. In some embodiments, the disclosed anti-CD73 antibody and/or variant or mutant (or fragment thereof) and/or pharmaceutical compositions provided herein can be administered by parenteral administration. By "parenteral" is meant intravenous, subcutaneous and intramuscular administration.

In some embodiments, the disclosed anti-CD73 antibody and/or variant or mutant (or fragment thereof) and/or pharmaceutical compositions provided herein can be administered in combination with at least one agent, such as a second, third, or fourth agent. The at least one agent can be any suitable agent known to treat a cancer or fibrosis, including idiopathic pulmonary fibrosis.

In various embodiments, the disclosed anti-CD73 antibody and/or variant or mutant (or fragment thereof) and/or pharmaceutical compositions provided herein can be administered in combination with at least one agent used in cancer treatment. In a specific embodiment, the disclosed anti-CD73 antibody and/or variant or mutant (or fragment thereof) and/or pharmaceutical compositions provided herein can be administered in combination with at least one agent used in cancer treatment such as oxaliplatin, leucovorin, fluorouracil (5-FU), gemcitabine, paclitaxel (including protein-bound paclitaxel such as, but not limited to, nanoparticle albumin-bound paclitaxel, which is sometimes referred to as "nab-paclitaxel") or combinations thereof.

Further examples of the least one agent used in cancer treatment include, but are not limited to, chemotherapeutic agents, immunotherapeutics, cancer vaccines, anti-angiogenic agents, cytokines, hormone therapies, gene therapies, biological therapies, and radiotherapies. For example, the at least one agent known to treat a cancer can be a known cytostatic or cytotoxic or anticancer agent such as an antineoplastic agent, a growth inhibitory agent, a cytotoxic agent, or a chemotherapeutic agent, such as docetaxel, gefitinib, FOLFIRI (irinotecan, 5-fluorouracil, and leucovorin), irinotecan, cisplatin, carboplatin, paclitaxel, bevacizumab (anti-VEGF antibody), FOLFOX-4, infusional fluorouracil, leucovorin, and oxaliplatin, afatinib, gemcitabine, capecitabine, pemetrexed, tivantinib, everolimus, CpG-ODN, rapamycin, lenalidomide, vemurafenib, endostatin, lapatinib, PX-866, Imprime PGG, and irlotinibm.

In some embodiments, the anti-CD73 antibodies and/or variants/mutants (or fragments thereof) are conjugated to the additional agent. For examples, the at least one agent include uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatin®), iressa (gefinitib, Zd1839), XELODA® (capecitabine), Tarceva® (erlotinib), azacitidine (5-Azacytidine; 5-AzaC), temozolomide (Temodar®), gemcitabine (e.g., GEMZAR® (gemcitabine HCl)), and vasostatin.

In various embodiments, the disclosed anti-CD73 antibody and/or variant or mutant (or fragment thereof) and/or pharmaceutical compositions provided herein can be administered in combination with at least one agent such as an alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-Il (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TML); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosf amide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaIl and calicheamicin omegaII (see, e.g., Nicolaou K C. et al., *Angew. Chem. Int. Ed. Engl.,* 33:183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethane; vindesine (ELDISEME®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

In various embodiments, the disclosed anti-CD73 antibody and/or variant or mutant (or fragment thereof) and/or pharmaceutical compositions provided herein can be administered in combination with at least one agent that is an angiogenesis inhibitor, such as, but not limited to, Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; combretastatin A-4; endostatin (collagen XVIII fragment); fibronectin fragment; gro-beta; halofuginone; heparinases; heparin hexasaccharide fragment; HMV833; human chorionic gonadotropin (hCG); IM-862; interferon alpha/beta/gamma; interferon inducible protein (IP-10); interleukin-12; Kringle 5 (plasminogen fragment); marimastat; metalloproteinase inhibitors (TIMPs); 2-methoxyestradiol; MMI 270 (CGS 27023A); MoAb IMC-1C11; neovastat; NM-3; panzem; PI-88; placenta ribonuclease inhibitor; plasminogen activator inhibitor; platelet factor-4 (PF4); prinomastat; prolactin 16 kD fragment; proliferin-related protein (PRP); PTK 787/ZK 222594; retinoids; solimastat; squalamine; SS 3304; SU 5416; SU6668; SU11248; tetrahydrocortisol-S; tetrathiomolybdate; thalidomide; thrombospondin-1 (TSP-1); TNP-470; transforming growth factor-beta (TGF-b); vasculostatin; vasostatin (calreticulin fragment); ZD6126; ZD 6474; farnesyl transferase inhibitors (FTI); and bisphosphonates.

In various embodiments, the disclosed anti-CD73 antibody and/or variant or mutant (or fragment thereof) and/or pharmaceutical compositions provided herein can be administered in combination with at least one agent selected from DNA interactive agents, such as cisplatin or doxorubicin;

topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and antimetabolites, such as methotrexate, other tyrosine kinase inhibitors such as Iressa and OSI-774; angiogenesis inhibitors; BTK inhibitors, SYK inhibitors, ITK inhibitors, PI3-kinase inhibitors, FLT3 inhibitors, EGF inhibitors; PAK inhibitors, VEGF inhibitors; CDK inhibitors; SRC inhibitors; c-Kit inhibitors; Her½ inhibitors and monoclonal antibodies directed against growth factor receptors such as erbitux (EGF) and herceptin (Her2) and other protein kinase modulators as well. These agents can be used in combination with differentiation agents such as ATRA, EZH2 inhibitors, DNMT inhibitors, corticosteroids, IDH1 inhibitors, IDH2 inhibitors, and Vitamin C.

In various embodiments, the disclosed anti-CD73 antibody and/or variant or mutant (or fragment thereof) and/or pharmaceutical compositions provided herein can be administered in combination with small molecules that enhance DNA damage killing in cancer cells including PARP inhibitors, MDM2 inhibitors, NAMPT inhibitors, and HSP90 inhibitors.

In various embodiments, the disclosed anti-CD73 antibody and/or variant or mutant (or fragment thereof) and/or pharmaceutical compositions provided herein can be administered in combination with one or more immunotherapeutic agents, including antagonists, antibodies and immunomodulators, which include, but are not limited to, HERCEPTINS, RITUXANS, OVAREX™, PANOREX®, BEC2, IMC-C225, VITAMIN, CAMPATH® I/H, Smart MI95, LYM-PHOCIDE™, Smart I D10, and ONCOLYM™, rituximab, gemtuzumab, or trastuzumab. In other instances, the immunotherapeutic agent can be an antibody targeting PD-1, PD-L1, PD-L2, CTLA4, LAG3, TIGIT, TIM3, CEACAM-1, Galectin-1, galectin-9, BLTA, CD69, CD113, GPR56, 2B4, CD48, PD1H, LAIR1, TIM-1, TIM-4, VISTA, GARP, CD73, CD39, A2AR, B7-1, B7-2, 4-1BBL, CD137, CD28, CD28H, GITR, GITRL, ICOS, ICOS-L, OX40, OX40L, CD70, CD27, CD40, DR3 or combinations of antibodies to such targets. In some instances, the immunotherapeutic agent can be an antagonist targeting PD-1, PD-L1, PD-L2, CTLA4, LAG3, TIGIT, TIM3, CEACAM-1, Galectin-1, galectin-9, BLTA, CD69, CD113, GPR56, 2B4, CD48, PD1H, LAIR1, TIM-1, TIM-4, VISTA, GARP, CD73, CD39, A2AR, or combinations thereof; an agonist targeting B7-1, B7-2, 4-1BBL, CD137, CD28, CD28H, GITR, GITRL, ICOS, ICOS-L, OX40, OX40L, CD70, CD27, CD40, DR3, or combinations thereof; or combinations of the foregoing antagonists and agonists.

In various embodiments, the disclosed anti-CD73 antibody and/or variant or mutant (or fragment thereof) and/or pharmaceutical compositions provided herein can be administered in combination with antibodies that target cell surface molecules on immune or cancer cells including but not limited to EGFR, HER2, CD38, mesothelin, CD33, CD37, CD19, CD20, CD3, CD123, CD70, BAFFR, CD4, CD8, CD56, CD38, or combinations of such antibodies. In some specific embodiments, the disclosed anti-CD73 antibody and/or variant or mutant (or fragment thereof) and/or pharmaceutical compositions provided herein can be administered in combination with antibodies that target cell surface molecules on immune or cancer cells including but not limited to EGFR, HER2, or combinations of such antibodies.

In various embodiments, the disclosed anti-CD73 antibody and/or variant or mutant (or fragment thereof) and/or pharmaceutical compositions provided herein can be administered in combination with at least one chemotherapeutic agent, such as an alkylating agents, antimetabolites, platinating agents, taxoid, anti-hormonal agent, topoisomerase inhibitors, tubulin agents, signaling inhibitors (e.g., kinase inhibitors), and other chemotherapeutic agents. A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou K C. et al., *Angew. Chem. Int. Ed. Engl.*, 33:183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyano-morpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone;

elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN®); bisphosphonates such as clodronate (for example, BONEFOSO® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Herein, chemotherapeutic agents include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4 (5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

Herein, a "taxoid" is a chemotherapeutic agent that functions to inhibit microtubule depolymerization. Examples include paclitaxel (TAXOL®), albumin-engineered nanoparticle formulation of paclitaxel (ABRAXANE™), and docetaxel (TAXOTERE®). The preferred taxoid is paclitaxel.

As used herein, the term "EGFR inhibitor" refers to compounds that bind to or otherwise interact directly with EGFR and prevent or reduce its signaling activity, and is alternatively referred to as an "EGFR antagonist". Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto G. et al., *Eur. J. Cancer,* 32A(4): 636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns T G. et al., *J. Biol. Chem.,* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654, 307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl) amino]-7-[3-(4-morpholinyl) propoxy]-6-quinazolinyl]-, dihydrochloride, Pfizer Inc.); ZD1839, gefitinib (IRESSA J) 4-(3'-Chloro-4'-fluoroanilino)-7-methoxy-6-(3-morpholino propoxy) quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl) amino]-1H-pyrrolo[2,3-d]pyrimidin-6-yl]-phenol); (R)-6-(4-hydroxyphenyl)-4-[(1-phenylethyl)amino]-7H-pyrrolo [2,3-d]pyrimidine); CL-387785 (N-[4-[(3-bromophenyl) amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3fluorophenyl) methoxy]phe-nyl]6 [5 [[2methylsulfonyl)ethyl]amino]methyl]-2-furanyl]-4-quinazolinamine; Glaxo-SmithKline).

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVAC J) available from Glaxo; MAPK extracellular regulated kinase I inhibitor CI-1040 (available from Pharmacia); quinazolines, such as PD 153035,4-(3-chloroanilino) quinazoline; pyridopyrimi-dines; pyrimidopyrimidines; pyrrolopyrimidines, such as CGP 59326, CGP 60261 and CGP 62706; pyrazolopyrimi-dines, 4-(phenylamino)-7H-pyrrolo[2,3-d]pyrimidines; cur-cumin (diferuloylmethane, 4,5-bis(4-fluoroanilino) phthal-imide); tyrphostines containing nitrothiophene moieties; PD-0183805 (Warner-Lambert); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanamid); WO98/43960 (American Cyana-mid); WO97/38983 (Warner Lambert); WO99/06378 (War-ner Lambert); WO99/06396 (Warner Lambert); WO96/30347 (Pfizer, Inc); WO96/33978 (Zeneca); WO96/3397 (Zeneca); and WO96/33980 (Zeneca).

In various embodiments, the disclosed anti-CD73 anti-body and/or variant or mutant (or fragment thereof) and/or pharmaceutical compositions provided herein can be admin-istered in combination with actinomycin D, capecitabine, carboplatin, cisplatin, colchicine, daunorubicin, docetaxel, doxorubicin, epirubicin, etoposide, 5-fluorouracil, gemcit-abine, melphalan, methotrexate, mitomycin C, mitoxan-trone, paclitaxel, thalidomide, topotecan, vinblastine, and vincristine.

In various embodiments, a disclosed anti-CD73 antibod-ies and/or variants or mutants (or fragments thereof) and/or pharmaceutical compositions provided herein can be admin-istered in combination with one or more additional therapies or clinical interventions, such as radiation therapy, surgery, chemotherapy, and/or targeted therapy. In certain embodi-ments, the disclosed anti-CD73 antibody and/or variant (or fragment thereof) and/or pharmaceutical compositions pro-vided herein are administered in combination with radiation therapy with a disclosed cancer.

In some embodiments, a disclosed anti-CD73 antibody and/or variant or mutant (or fragment thereof) and/or phar-maceutical composition provided herein can be adminis-tered in connection with surgery, e.g., surgery can be per-formed prior to the administering of a disclosed anti-CD73 antibodies, surgery can be performed after administering of a disclosed anti-CD73 antibodies, and/or surgery can be performed at or about the same time as administering of a disclosed anti-CD73 antibodies.

Depending on the indication to be treated and factors relevant to the dosing that a physician of skill in the field would be familiar with, the anti-CD73 antibodies, variants, mutants, or fragments thereof, provided herein will be administered at an effective dosage, e.g., a dosage that is efficacious for the treatment of that indication while mini-mizing toxicity and side effects. It is generally preferred that a maximum dose of the pharmacological agents of the present disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons. In some instances, the effective dosage may be such that the desired response is inhibiting the progression of the disease or condition, e.g., progression of a cancer. This may involve only slowing the progression of the disease tempo-rarily, although more preferably, it involves halting the progression of the disease permanently. This can be moni-tored by routine diagnostic methods known to one of ordi-nary skill in the art for any particular disease. The desired response to treatment of the disease or condition also can be delaying the onset or even preventing the onset of the disease or condition.

Toxicity and therapeutic efficacy of the disclosed anti-CD73 antibodies and/or variants or mutants (or fragments thereof) and/or pharmaceutical compositions provided herein can be determined by standard pharmaceutical pro-cedures in cell cultures or experimental animals, e. g., for determining the $LD_{50}$ (the dose lethal to 50% of the popu-lation) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices can be desirable. While the dis-closed anti-CD73 antibodies and/or variants or mutants (or fragments thereof) and/or pharmaceutical compositions pro-vided herein that exhibit toxic side effects can be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of the disclosed anti-CD73 antibod-ies and/or variants or mutants (or fragments thereof) and/or pharmaceutical compositions provided herein lies preferably within a range of circulating concentrations that include the $ED_{50}$ with little or no toxicity. Dosages can vary within this range depending upon the dosage form employed and the route of administration utilized. For any of the disclosed anti-CD73 antibodies and/or variants or mutants (or fragments thereof) and/or pharmaceutical compositions provided herein, the therapeutically effective dose can be estimated initially from cell culture assays. A dose can be formulated in animal models to achieve a circulating plasma concentration range that includes the $IC_{50}$ as determined in cell culture experiments. Such information can be used to more accurately determine useful doses in humans. Levels in plasma can be measured, for example, by high performance liquid chromatography.

The anti-cancer activity of the disclosed anti-CD73 antibodies and/or variants or mutants (or fragments thereof) and/or pharmaceutical compositions provided herein can be determined by using various experimental animal models of such as the SCID mouse model or nude mice with human tumor grafts known in the art and described in Yamanaka K. et al., *Microbiol. Immunol.*, 45(7): 507-514 (2001).

The disclosed anti-CD73 antibodies and/or variants or mutants (or fragments thereof) and/or pharmaceutical compositions provided herein can be tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed.

A lower level of proliferation or survival of the contacted cells can indicate that the disclosed anti-CD73 antibodies and/or variants or mutants (or fragments thereof) and/or pharmaceutical compositions provided herein can be effective to treat a selected disorder in a subject. Alternatively, instead of culturing cells from a patient, protocols can be screened using cells of a tumor or malignant cell line. Many assays known in the art can be used to assess such survival and/or growth; for example, cell proliferation can be assayed by measuring 3H-thymidine incorporation, by direct cell count, by detecting changes in transcriptional activity of known genes such as proto-oncogenes or cell cycle markers; cell viability can be assessed by trypan blue staining, while differentiation can be assessed visually based on changes in morphology, etc.

The disclosed anti-CD73 antibodies and/or variants or mutants (or fragments thereof) and/or pharmaceutical compositions provided herein for use in therapy can be tested in suitable animal model systems prior to testing in humans, including but not limited to in rats, mice, chicken, cows, monkeys, rabbits, etc. The principle animal models for cancer known in the art and widely used include mice, such as described in Hann B. et al., *Curr. Opin. Cell Biol.*, 13(6): 778-784 (2001), which is incorporated herein by reference in its entirety.

Further, any assays known to those skilled in the art can be used to evaluate the prophylactic and/or therapeutic utility of the disclosed anti-CD73 antibodies and/or variants or mutants (or fragments thereof) and/or pharmaceutical compositions provided herein for treatment, prophylaxis, management or amelioration of one or more symptoms associated with a disease or disorder as described hereinabove.

Suitable daily doses for the treatment or prevention of a disorder described herein can be readily determined by those skilled in the art. For the treatment of a disclosed cancer a typical dose can be, for example, in the rage of 0.001 to 1000 µg; however, doses below or above this exemplary range are within the scope of the present disclosure. The daily dose can be about 0.1 µg/kg to about 100 mg/kg of total body weight (e.g., about 5 µg/kg, about 10 µg/kg, about 100 µg/kg, about 500 µg/kg, about 1 mg/kg, about 50 mg/kg, or a range defined by any two of the foregoing values), preferably from about 0.3 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 1 mg/kg of total body weight (e.g., about 3 µg/kg, about 15 µg/kg, about 75 µg/kg, about 300 µg/kg, about 900 µg/kg, or a range defined by any two of the foregoing values), and even more preferably from about 0.5 to 10 mg/kg body weight per day (e.g., about 2 mg/kg, about 4 mg/kg, about 7 mg/kg, about 9 mg/kg, or a range defined by any two of the foregoing values, including any range between the foregoing values). As noted above, therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the present disclosure. The desired dosage can be delivered by a single bolus administration of the composition, by multiple bolus administrations of the composition, or by continuous infusion administration of the composition.

A pharmaceutical composition comprising the anti-CD73 antibody, variant, mutant, or a fragment thereof can be administered one, two, three, or four times daily. The compositions can also be administered less frequently than daily, for example, six times a week, five times a week, four times a week, three times a week, twice a week, once a week, once every two weeks, once every three weeks, once per month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection.

The antibody and/or variant or mutant (or a fragment thereof) may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The antibody (or a fragment thereof) may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgically implanted in various locations.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation 100-(T/C×100), where T is the mean relative tumor volume of the treated tumor, and C is the mean relative tumor volume of a non-treated tumor. In certain embodiments, the % TGI is about 10%, about 20%, about 30%, about 40%, about 50%, about 60%, about 70%, about 80%, about 90%, about 91%, about 92%, about 93%, about 94%, about 95%, or more than 95%. In certain embodiments the % TGI of an anti-CD73 and/or its variant or mutant is the same as or greater than the % TGI of the reference anti-CD73 antibody, such as about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 2.6-fold, about 2.7-fold, including any range in between these values, or more than about 2.7-fold greater than the % TGI of the reference anti-CD73 antibody.

Pharmaceutical Compositions

The disclosed anti-CD73 antibody and/or variant or mutant (or fragment thereof) of the present disclosure can be prepared as a pharmaceutical composition comprising suitable carriers or excipients so that they are suitable for administration. Suitable pharmaceutical compositions of the antibodies are obtained by mixing an antibody (or fragment thereof) having the desired degree of purity with optional pharmaceutically acceptable carriers, excipients or stabilizers (Remington's Pharmaceutical Sciences, 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations are described in WO98/56418, expressly incorporated herein by reference. Lyophilized pharmaceutical compositions adapted for subcutaneous administration are described in WO97/04801. Such lyophilized pharmaceutical compositions may be reconstituted with a suitable diluent to a high protein concentration and the reconstituted formulation may be administered subcutaneously to the mammal to be treated herein.

In some embodiments, a disclosed pharmaceutical composition is suitable for parenteral or intravenous administration. In some instances, the disclosed pharmaceutical composition suitable for parenteral administration can be an aqueous and non-aqueous formulation that is isotonic with the blood of the intended subject; and aqueous and non-aqueous sterile suspensions may include suspending systems designed to target the compound to blood components of one or more organs. The formulations may be presented in unit-dose or multi-dose sealed containers, for example, ampoules or vials. Extemporaneous injection solutions and suspensions may be prepared from sterile powders, granules and tablets of the kind previously described. Parenteral and intravenous formulation may include minerals and other materials to make them compatible with the type of injection or delivery system chosen.

Commonly used pharmaceutically acceptable carriers for parenteral administration includes, water, a suitable oil, saline, aqueous dextrose (glucose), or related sugar solutions and glycols such as propylene glycol or polyethylene glycols. Solutions for parenteral administration preferably contain a water soluble salt of the active ingredient, suitable stabilizing agents and, if necessary, buffer substances, antioxidizing agents, such as sodium bisulfite, sodium sulfite, or ascorbic acid, either alone or combined, are suitable stabilizing agents. Citric acid salts and sodium EDTA may also be used as carriers. In addition, parenteral solutions may contain preservatives, such as benzalkonium chloride, methyl- or propyl-paraben, or chlorobutanol. Suitable pharmaceutical carriers are described in Remington, cited above.

Injectable formulations can be prepared in conventional forms, either as liquid solutions or suspensions; as solid forms suitable for solubilization or suspension in liquid prior to injection; or as emulsions. Preferably, sterile injectable suspensions are formulated according to techniques known in the art using suitable pharmaceutically acceptable carriers and other optional components, as described above.

Parenteral administration may be carried out in any number of ways, but it is preferred that a syringe, catheter, or similar device, be used to effect parenteral administration of the formulations described herein. The formulation may be injected systemically such that the active agent travels substantially throughout the entire bloodstream.

Also, the formulation may also be injected locally to a target site, e.g., injected to a specific portion of the body for treatment of a cancer or fibrosis is desired. An advantage of local administration via injection is that it limits or avoids exposure of the entire body to the active agent(s) (e.g., inhibitors and/or other therapeutic agents). It must be noted that in the present context, the term local administration includes regional administration, e.g., administration of a formulation directed to a portion of the body through delivery to a blood vessel serving that body zone. Local delivery may be direct, e.g., intratumoral. Local delivery may also be nearly direct, i.e., intralesional or intraperitoneal, that is, to an area that is sufficiently close to a tumor or site of infection so that the inhibitor exhibits the desired pharmacological activity. Thus, when local delivery is desired, the pharmaceutical formulations are preferably delivered intralesionally, intratumorally, or intraperitoneally.

In certain embodiments, the pharmaceutical compositions are in unit dosage form. In such form, the composition is divided into unit doses containing appropriate quantities of the active component. The unit dosage form can be a packaged preparation, the package containing discrete quantities of the preparations, for example, lyophilized powders in vials or ampoules.

The pharmaceutical composition herein may also contain more than one active compound as necessary for the particular indication being treated, preferably those with complementary activities that do not adversely affect each other. For example, it may be desirable to further provide an antineoplastic agent, a growth inhibitory agent, a cytotoxic agent, or a chemotherapeutic agent. Such molecules are suitably present in combination in amounts that are effective for the purpose intended. The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages. The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. Ed. (1980).

Sustained-release preparations may be prepared. Suitable examples of sustained release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Lipofectins or liposomes can be used to deliver the polypeptides and antibodies (or fragments thereof) or compositions of this present disclosure into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco W A. et al., *Proc. Natl. Acad. Sci. USA*, 90(16): 7889-7893 (1993).

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. Such techniques are disclosed in Remington's PHARMACEUTICAL SCIENCES, supra.

Sustained-release preparations can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In certain embodiments, the formulation comprises an anti-CD73 antibody and/or its variant or mutant described herein at a concentration of greater than about 0.5 mg/mL, greater than about 1 mg/mL, greater than about 2 mg/mL, greater than about 3 mg/mL, greater than about 4 mg/mL, greater than about 5 mg/mL, greater than about 6 mg/mL, greater than about 7 mg/mL, greater than about 8 mg/mL, greater than about 9 mg/mL, greater than about 10 mg/mL, greater than about 11 mg/mL, greater than about 12 mg/mL, greater than about 13 mg/mL, greater than about 14 mg/mL, greater than about 15 mg/mL, greater than about 16 mg/mL, greater than about 17 mg/mL, greater than about 18 mg/mL, greater than about 19 mg/mL, greater than about 20 mg/mL, greater than about 21 mg/mL, greater than about 22 mg/mL, greater than about 23 mg/mL, greater than about 24 mg/mL, greater than about 25 mg/mL, greater than about 26 mg/mL, greater than about 27 mg/mL, greater than about 28 mg/mL, greater than about 29 mg/mL, or greater than about 30 mg/mL, including any range in between these values.

The formulation comprising a disclosed antibody should have a pH (in the final formulation) that is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution. For example, in certain embodiments, a disclosed pharmaceutical formulation at a pH in the range of 4.0 to 7.0 can comprise: 1 to 200 mg/mL of an antibody according to the present disclosure and 1 to 100 mM of a buffer, and optionally one or more of the following: (a) 0.001 to 1% of a surfactant, (b) 10 to 500 mM of a stabiliser, (c) 10 to 500 mM of a stabiliser and 5 to 500 mM of a tonicity agent, and/or (d) 5 to 500 mM of a tonicity agent. Suitable buffers include, but are not limited to, citrate, glycine, phosphate, acetate, succinate, and bicarbonate. For example, a formulation at approximately pH 6 can comprise 1 to 50 mg/mL of antibody, 20 mM L-histadine HCl, 240 mM trehalose and 0.02% polysorbate 20. Alternatively a formulation at approximately pH 5.5 may comprise 1 to 50 mg/mL of antibody, 20 mM citrate buffer, 240 mM sucrose, 20 mM arginine, and 0.02% polysorbate 20.

In certain embodiments, the anti-CD73 antibody and/or variant or mutant thereof is formulated (e.g., at a concentration greater than about 0.5 mg/mL, greater than about 1 mg/mL, greater than about 5 mg/mL, greater than about 10 mg/mL, greater than about 15 mg/mL, greater than about 20 mg/mL, or greater than about 25 mg/mL, including any range in between these values) in a buffer comprising a citrate, NaCl, acetate, succinate, glycine, polysorbate 80 (Tween 80), or any combination of the foregoing. In certain embodiments, the anti-CD73 antibody and/or variant thereof is formulated (e.g., at a concentration greater than about 0.5 mg/mL, greater than about 1 mg/mL, greater than about 5 mg/mL, greater than about 10 mg/mL, greater than about 15 mg/mL, greater than about 20 mg/mL, or greater than about 25 mg/mL, including any range in between these values) in a buffer comprising about 100 mM to about 150 mM glycine. In certain embodiments, the anti-CD73 antibody and/or variant thereof is formulated in a buffer comprising about 50 mM to about 100 mM NaCl. In certain embodiments, the anti-CD73 antibody and/or variant or mutant thereof is formulated (e.g., at a concentration greater than about 0.5 mg/mL, greater than about 1 mg/mL, greater than about 5 mg/mL, greater than about 10 mg/mL, greater than about 15 mg/mL, greater than about 20 mg/mL, or greater than about 25 mg/mL, including any range in between these values) in a buffer comprising about 10 mM to about 50 mM acetate. In certain embodiments, the anti-CD73 antibody and/or variant thereof is formulated in a buffer comprising about 10 mM to about 50 mM succinate. In certain embodiments, the anti-CD73 antibody and/or variant or mutant thereof is formulated (e.g., at a concentration greater than about 0.5 mg/mL, greater than about 1 mg/mL, greater than about 5 mg/mL, greater than about 10 mg/mL, greater than about 15 mg/mL, greater than about 20 mg/mL, or greater than about 25 mg/mL, including any range in between these values) in a buffer comprising about 0.005% to about 0.02% polysorbate 80. In certain embodiments, the anti-CD73 antibody and/or variant or mutant thereof is formulated in a suitable buffer to provide a buffered pH of between about 5.1 and 5.6. For example, the anti-CD73 antibody and/or variant or mutant thereof can be formulated in a buffer comprising 10 mM citrate, 100 mM NaCl, 100 mM glycine, and 0.01% polysorbate 80, wherein the formulation is at pH=5.5.

In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an anti-CD73 antibody and/or variant or mutant thereof described herein (e.g., at a concentration greater than about 0.5 mg/mL, greater than about 1 mg/mL, greater than about 5 mg/mL, greater than about 10 mg/mL, greater than about 15 mg/mL, greater than about 20 mg/mL, or greater than about 25 mg/mL, including any range in between these values) is stable at room temperature (such as at about 20-25° C. for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values. In certain embodiments, a formulation (such as a formulation comprising buffer comprising 10 mM citrate, 100 mM NaCl, 100 mM glycine, and 0.01% polysorbate 80, wherein the formulation is at pH=5.5) comprising an anti-CD73 antibody and/or variant or mutant thereof described herein (e.g., at a concentration greater than about 0.5 mg/mL, greater than about 1 mg/mL, greater than about 5 mg/mL, greater than about 10 mg/mL, greater than about 15 mg/mL, greater than about 20 mg/mL, or greater than about 25 mg/mL, including any range in between these values) is stable under accelerated conditions (such as storage at about 37° C.) for about 0.5 weeks, 1.0 weeks, 1.5 weeks, 2.0 weeks, 2.5 weeks, 3.5 weeks, 4.0 weeks, 4.5 weeks, or 5.0 weeks, including any range in between these values.

Size exclusion chromatography (SEC) is a well-known and widely used method used in protein stability studies to detect potential fragmentation and aggregation, corresponding to physical and chemical instabilities. In certain embodiments, a formulation comprising 5 mg/mL, 10 mg/mL, 15 mg/mL, 20 mg/mL, or 25 mg/mL of an anti-CD73 antibody and/or variant or mutant thereof described herein shows less than about a 1.6%, 1.4%, 1.2%, 1.0%, 0.8%, 0.6%, 0.4%, 0.2%, or 0.1% increase in high molecular weight species (HMWS) after 1 week at 37° C., relative to the initial % high molecular weight species, as measured using SEC, including any range in between these values. In certain embodiments, a formulation comprising 5 mg/mL, 10 mg/mL, 15 mg/mL, 20 mg/mL, or 25 mg/mL of an anti-CD73 antibody described herein shows less than about a 2.0%, 1.8% 1.6%, 1.4%, 1.2%, 1.0%, 0.8%, 0.6%, 0.4%, 0.2%, or 0.1% increase in high molecular weight species after 2 weeks at 37° C., relative to the initial % high molecular weight species, as measured using SEC, including any range in between these values. In certain embodiments, a formulation comprising 5 mg/mL, 10 mg/mL, 15 mg/mL, 20 mg/mL, or 25 mg/mL of an anti-CD73 antibody and/or variant or mutant thereof described herein shows less than about a 3.3%, 3.2%, 3.1%, 3.0%, 2.9%, 2.8%, 2.7%, 2.6%, 2.5%, 2.4%, 2.2%, 2.0%, 1.8% 1.6%, 1.4%, 1.2%, 1.0%, 0.8%, 0.6%, 0.4%, 0.2%, or 0.1% increase in high molecular weight species after 4 weeks at 37° C., relative to the initial % high molecular weight species, as measured using SEC, including any range in between these values.

In certain embodiments, a formulation comprising 5 mg/mL, 10 mg/mL, 15 mg/mL, 20 mg/mL, or 25 mg/mL of an anti-CD73 antibody and/or variant or mutant thereof described herein shows less than about a 1.6%, 1.4%, 1.2%, 1.0%, 0.8%, 0.6%, 0.4%, 0.2%, or 0.1% increase in low molecular weight species (LMWS) after 1 week at 37° C., relative to the initial % low molecular weight species, as measured using SEC, including any range in between these values. In certain embodiments, a formulation comprising 5 mg/mL, 10 mg/mL, 15 mg/mL, 20 mg/mL, or 25 mg/mL of an anti-CD73 antibody and/or variant or mutant thereof described herein shows less than about a 2.0%, 1.8% 1.6%, 1.4%, 1.2%, 1.0%, 0.8%, %, 0.4%, 0.2%, or 0.1% increase in low molecular weight species after 2 weeks at 37° C., relative to the initial % low molecular weight species, as measured using SEC, including any range in between these values. In certain embodiments, a formulation comprising 5 mg/mL, 10 mg/mL, 15 mg/mL, 20 mg/mL, or 25 mg/mL of an anti-CD73 antibody and/or variant or mutant thereof described herein shows less than about a 2.4%, 2.2%, 2.0%, 1.8% 1.6%, 1.4%, 1.2%, 1.0%, 0.8%, 0.6%, 0.4%, 0.2%, or 0.1% increase in low molecular weight species after 4 weeks at 37° C., relative to the initial % low molecular weight species, as measured using SEC, including any range in between these values.

In certain embodiments, a formulation comprising 5 mg/mL, 10 mg/mL, 15 mg/mL, 20 mg/mL, or 25 mg/mL of an anti-CD73 antibody and/or variant or mutant thereof described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 1 week at 37° C., relative to the initial % monomer, as measured using SEC, including any range in between these values. In certain embodiments, a formulation comprising 5 mg/mL, 10 mg/mL, 15 mg/mL, 20 mg/mL, or 25 mg/mL of an anti-CD73 antibody and/or variant or mutant thereof described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values. In certain embodiments, a formulation comprising 5 mg/mL, 10 mg/mL, 15 mg/mL, 20 mg/mL, or 25 mg/mL of an anti-CD73 antibody and/or variant or mutant thereof described herein shows no more than about a 0.2%, 0.4%, 0.6%, 0.8%, 0.9%, 1.0%, 1.1%, 1.2%, 1.3%, 1.4%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, or 3.5% decrease in monomer after 2 weeks at 37° C., relative to the initial % monomer, as measured using SEC, including any range in between these values.

Cation exchange chromatography (CEX) is a well-known and widely used tool to detect protein degradation events such as deamidation or oxidation (Moorhouse K G. et al., J. Pharm. Biomed. Anal., 16(4): 593-603, 1997). Degradation products are typically referred to as acidic or basic species. Acidic species are the variants that elute earlier than the main peak from CEX, while basic species are the variants that elute later than the main peak from CEX. In certain embodiments, the acidic peak fraction of a formulation comprising 5 mg/mL, 10 mg/mL, 15 mg/mL, 20 mg/mL, or 25 mg/mL of an anti-CD73 antibody and/or variant or mutant thereof described herein is no more than about 7%, 8%, 9%, 10%, 11%, 12%, 13%, 14%, or 15% of total protein after 1 week at 37° C., as measured using CEX, including any range in between these values. In certain embodiments, the acidic peak fraction of a formulation comprising 5 mg/mL, 10 mg/mL, 15 mg/mL, 20 mg/mL, or 25 mg/mL of an anti-CD73 antibody and/or variant or mutant thereof described herein is no more than about 8%, 9%, 10%, 11%, 12%, 13%, 14%, 15%, 16%, 17%, or 18% of total protein after 2 weeks at 37° C., as measured using CEX, including any range in between these values. In certain embodiments, the acidic peak fraction of a formulation comprising 5 mg/mL, 10 mg/mL, 15 mg/mL, 20 mg/mL, or 25 mg/mL of an anti-CD73 antibody and/or variant or mutant (or frag-ment) thereof described herein is no more than about 8%, 9%, 10%, 11%, 12%, 13%, 14%, 15%, 16%, 17%, 18%, 19%, 20%, 21%, 22%, 23%, 24%, 25%, 26%, or 27% of total protein after 2 weeks at 37° C., as measured using CEX, including any range in between these values.

In certain embodiments, the basic peak fraction of a formulation comprising 5 mg/mL, 10 mg/mL, 15 mg/mL, 20 mg/mL, or 25 mg/mL of an anti-CD73 antibody and/or variant or mutant (or fragment) thereof described herein is no more than about 39%, 40%, 41%, 42%, 43%, 44%, 45%, or 46% of total protein after 1 week at 37° C., as measured using CEX, including any range in between these values. In certain embodiments, the basic peak fraction of a formula-tion comprising 5 mg/mL, 10 mg/mL, 15 mg/mL, 20 mg/mL, or 25 mg/mL of an anti-CD73 antibody and/or variant or mutant (or fragment) thereof described herein is no more than about 39%, 40%, 41%, 42%, 43%, 44%, 45%, or 46% of total protein after 2 weeks at 37° C., as measured using CEX, including any range in between these values. In certain embodiments, the basic peak fraction of a formula-tion comprising 5 mg/mL, 10 mg/mL, 15 mg/mL, 20 mg/mL, or 25 mg/mL of an anti-CD73 antibody and/or variant or mutant (or fragment) thereof described herein is no more than about 39%, 40%, 41%, 42%, 43%, 44%, 45%, or 46% of total protein after 4 weeks at 37° C., as measured using CEX, including any range in between these values.

In certain embodiments, the main peak fraction of a formulation comprising 5 mg/mL, 10 mg/mL, 15 mg/mL, 20 mg/mL, or 25 mg/mL of an anti-CD73 antibody and/or variant or mutant (or fragment) thereof described herein is no less than about 32%, 33%, 34%, 35%, 36%, 37%, 38%, 39%, 40%, 41%, 42%, 43%, 44%, 45%, or 46% of total protein after 1 week at 37° C., as measured using CEX, including any range in between these values. In certain embodiments, the basic peak fraction of a formulation comprising 5 mg/mL, 10 mg/mL, 15 mg/mL, 20 mg/mL, or 25 mg/mL of an anti-CD73 antibody and/or variant or mutant (or fragment) thereof described herein is no less than about 32%, 33%, 34%, 35%, 36%, 37%, 38%, 39%, 40%, 41%, 42%, 43%, 44%, 45%, or 46% of total protein after 2 weeks at 37° C., as measured using CEX, including any range in between these values. In certain embodiments, the basic peak fraction of a formulation comprising 5 mg/mL, 10 mg/mL, 15 mg/mL, 20 mg/mL, or 25 mg/mL of an anti-CD73 antibody and/or variant or mutant (or fragment) thereof described herein is no less than about 32%, 33%, 34%, 35%, 36%, 37%, 38%, 39%, 40%, 41%, 42%, 43%, 44%, 45%, or 46% of total protein after 4 weeks at 37° C., as measured using CEX, including any range in between these values.

The formulations to be used for in vivo administration must be sterile. This is readily accomplished by, e.g., filtra-tion through sterile filtration membranes.

Methods of Diagnosis and Imaging Using Anti-CD73 Anti-bodies and Variants/Mutants Thereof Labeled anti-CD73 antibodies, variants, mutants, frag-ments thereof, and derivatives and analogs thereof, which specifically bind to a CD73 can be used for diagnostic purposes to detect, diagnose, or monitor diseases and/or disorders associated with the expression, aberrant expres-sion and/or activity of CD73. For example, The disclosed anti-CD73 antibody and/or variant or mutant (or fragment thereof) provided herein can be used in in situ, in vivo, ex vivo, and in vitro diagnostic assays or imaging assays. Methods for detecting expression of a CD73, comprising (a) assaying the expression of the polypeptide in cells (e.g., tissue) or body fluid of an individual using one or more antibodies of this present disclosure and (b) comparing the level of gene expression with a standard gene expression level, whereby an increase or decrease in the assayed gene expression level compared to the standard expression level is indicative of aberrant expression.

Additional embodiments provided herein include meth-ods of diagnosing a disease or disorder associated with expression or aberrant expression of CD73 in an animal (e.g., a mammal such as a human). The methods comprise detecting CD73 molecules in the mammal. In certain embodiments, diagnosis comprises: (a) administering an effective amount of a labeled anti-CD73 antibody and/or variant or mutant (or fragment) thereof to a mammal (b) waiting for a time interval following the administering for permitting the labeled anti-CD73 antibody and/or variant or mutant (or fragment) thereof to preferentially concentrate at sites in the subject where the CD73 is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of CD73. Background level can be determined by various methods including, comparing the amount of labeled molecule detected to a standard value previously determined for a particular system.

Anti-CD73 antibodies and/or variants or mutants (or fragments) thereof provided herein can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115\,m}$In, $^{113m}$In, $^{112}$In, $^{111}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), samarium ($^{153}$Sm), lutetium ($^{177}$Lu), gadolinium ($^{159}$Gd), promethium ($^{149}$Pm), lanthanum ($^{140}$La), ytterbium ($^{175}$Yb), holmium ($^{166}$Ho), yttrium ($^{90}$Y), scandium ($^{47}$Sc), rhenium ($^{186}$Re, $^{188}$Re), praseodymium ($^{142}$Pr), rhodium ($^{105}$Rh), ruthenium ($^{97}$Ru); luminol; and fluorescent labels, such as fluorescein and rhodamine, and biotin.

Techniques known in the art may be applied to labeled antibodies (or fragments thereof) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274, 119; 4,994,560; and 5,808,003).

Alternatively, or additionally, one can measure levels of a CD73-encoding nucleic acid or mRNA in the cell, e.g., via fluorescent in situ hybridization using a nucleic acid based probe corresponding to a CD73-encoding nucleic acid or the complement thereof; (FISH; see WO98/454 79 published October 1998), Southern blotting, Northern blotting, or polymerase chain reaction (PCR) techniques, such as real time quantitative PCR (RT-PCR). One can also study CD73 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401, 638 issued Mar. 28, 1995; and Sias et al., *J. Immunol. Methods* 132:73-80 (1990)). Aside from the above assays, various in vivo and ex vivo assays are available to the skilled practitioner. For example, one can expose cells within the body of the mammal to an antibody which is optionally labeled with a detectable label, e.g., a radioactive isotope, and binding of the antibody to the cells can be evaluated, e.g., by external scanning for radioactivity or by analyzing a sample (e.g., a biopsy or other biological sample) taken from a mammal previously exposed to the antibody.

Articles of Manufacture and Kits

In various embodiment, the present disclosure relates to a kit comprising a disclosed anti-CD73 antibody, variant, mutant, and/or fragment thereof, and/or pharmaceutical compositions provided herein, and one or more of: (a) at least one agent known to treat a cancer; or (b) instructions for treating a cancer.

In a further embodiment, the disclosed anti-CD73 antibody, variant, mutant, and/or fragment thereof, and/or pharmaceutical compositions provided herein, and the at least one agent known to treat a cancer are co-formulated.

In a still further embodiment, the disclosed anti-CD73 antibody, variant, mutant, and/or fragment thereof, and/or pharmaceutical compositions provided herein, and the at least one agent known to treat a cancer are co-packaged.

In a further embodiment, the at least one agent known to treat a cancer is a hormone therapy agent. In a still further embodiment, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further embodiment, the at least one agent known to treat a cancer is a chemotherapeutic agent. In a still further embodiment, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent.

In a further embodiment, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further embodiment, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further embodiment, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further embodiment, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further embodiment, the mTor inhibitor agent is selected from one or more of the group consisting of everolimus, siroliumus, and temsirolimus, or a pharmaceutically acceptable salt, hydrate, solvate, or polymorph thereof.

In a further embodiment, the kit further comprises instructions to provide the disclosed anti-CD73 antibody, variant, mutant, and/or fragment thereof, and/or pharmaceutical compositions provided herein in connection with surgery. In a still further embodiment, the kit further comprises instructions to provide the disclosed anti-CD73 antibody, variant, mutant, and/or fragment thereof, and/or pharmaceutical compositions provided herein in connection with surgery, wherein the instructions provide that surgery is performed prior to the administering of at least one compound. In a yet further embodiment, the kit further comprises instructions to provide the disclosed anti-CD73 antibody, variant, mutant, and/or fragment thereof, and/or pharmaceutical compositions provided herein in connection with surgery, wherein the instructions provide that surgery is performed after the administering of the disclosed anti-CD73 antibody, variant, mutant, and/or fragment thereof, and/or pharmaceutical compositions provided herein. In an even further embodiment, the kit further comprises instructions to provide the disclosed anti-CD73 antibody, variant, mutant, and/or fragment thereof, and/or pharmaceutical compositions provided herein in connection with surgery, wherein the instructions provide that surgery is performed after the administering of the disclosed anti-CD73 antibody, variant, mutant, and/or fragment thereof, and/or pharmaceutical compositions provided herein, and wherein the instructions provide that the administering of the disclosed anti-CD73 antibody, variant, mutant, and/or fragment thereof, and/or pharmaceutical compositions provided herein is to effect presurgical debulking of a tumor. In a still further embodiment, the kit further comprises instructions to provide the compound in connection with surgery, wherein the instructions provide that surgery is performed after the administering of the disclosed anti-CD73 antibody, variant, mutant, and/or fragment thereof, and/or pharmaceutical compositions provided herein, and wherein the instructions provide that surgery is performed at about the same time as the administering of the disclosed anti-CD73 antibody, variant, mutant, and/or fragment thereof, and/or pharmaceutical compositions provided herein.

In a further embodiment, the kit further comprises instructions to provide the disclosed anti-CD73 antibody, variant, mutant, and/or fragment thereof, and/or pharmaceutical compositions in connection with radiotherapy. In a still further embodiment, the kit further comprises instructions to provide the disclosed anti-CD73 antibody, variant, mutant, and/or fragment thereof, and/or pharmaceutical compositions in connection with radiotherapy, wherein the instructions provide that radiotherapy is performed prior to the administering of the disclosed anti-CD73 antibody, variant, mutant, and/or fragment thereof, and/or pharmaceutical compositions. In a yet further embodiment, the kit further comprises instructions to provide the disclosed anti-CD73 antibody, variant, mutant, and/or fragment thereof, and/or pharmaceutical compositions in connection with radiotherapy, wherein the instructions provide that radiotherapy is performed after the step of the administering of the disclosed anti-CD73 antibody, variant, mutant, and/or fragment thereof, and/or pharmaceutical compositions. In an even further embodiment, the kit further comprises instructions to provide the disclosed anti-CD73 antibody, variant, mutant, and/or fragment thereof, and/or pharmaceutical compositions in connection with radiotherapy, wherein the instructions provide that radiotherapy is performed at about the same time as the step of the administering of the disclosed anti-CD73 antibody, variant, mutant, and/or fragment thereof, and/or pharmaceutical compositions.

In a further embodiment, the kit further comprises a plurality of dosage forms, the plurality comprising one or more doses; wherein each dose comprises a therapeutically effective amount of the disclosed anti-CD73 antibody, variant, mutant, and/or fragment thereof, and/or pharmaceutical compositions and the at least one agent. In a still further embodiment, the kit further comprises a plurality of dosage forms, the plurality comprising one or more doses; wherein each dose comprises a therapeutically effective amount of the disclosed anti-CD73 antibody, variant, mutant, and/or fragment thereof, and/or pharmaceutical compositions and the at least one agent, and wherein each dose of the disclosed anti-CD73 antibody, variant, mutant, and/or fragment thereof, and/or pharmaceutical compositions and the at least one agent known to treat a cancer are co-formulated. In a yet further embodiment, the kit further comprises a plurality of dosage forms, the plurality comprising one or more doses; wherein each dose comprises a therapeutically effective amount of the disclosed anti-CD73 antibody, variant, mutant, and/or fragment thereof, and/or pharmaceutical compositions and the at least one agent, and wherein each dose of the disclosed anti-CD73 antibody, variant, mutant, and/or fragment thereof, and/or pharmaceutical compositions and the at least one agent known to treat a cancer are co-packaged.

In a further embodiment, the kit further comprises a plurality of dosage forms, the plurality comprising one or more doses; wherein each dose comprises a therapeutically effective amount of the disclosed anti-CD73 antibody, variant, mutant, and/or fragment thereof, and/or pharmaceutical compositions is formulated for intravenous administration and the at least one agent is formulated for oral administration and/or intravenous administration. In a still further embodiment, the kit further comprises a plurality of dosage forms, the plurality comprising one or more doses; wherein each dose comprises a therapeutically effective amount of the disclosed anti-CD73 antibody, variant, mutant, and/or fragment thereof, and/or pharmaceutical compositions is formulated for intravenous administration and the at least one agent is formulated for oral administration. In a yet further embodiment, the kit further comprises a plurality of dosage forms, the plurality comprising one or more doses; wherein each dose comprises a therapeutically effective amount of the disclosed anti-CD73 antibody, variant, mutant, and/or fragment thereof, and/or pharmaceutical compositions is formulated for intravenous administration and the at least one agent is formulated for intravenous administration.

The disclosed anti-CD73 antibody, variant, mutant, and/or fragment thereof, and/or pharmaceutical compositions can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further embodiments, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further embodiment, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present disclosure also features such kits further containing instructions for use.

In a further embodiment, the present disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration.

In various embodiments, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Kits are also provided that are useful for various purposes, e.g., for isolation or detection of CD73 in patients, optionally in combination with the articles of manufacture. For isolation and purification of CD73, the kit can contain an anti-CD73 antibody and/or variant or mutant (or fragment) thereof provided herein coupled to beads (e.g., SEPHAR-OSE™ beads). Kits can be provided which contain the antibodies (or fragments thereof) for detection and quantitation of CD73 in vitro, e.g. in an ELISA or a Western blot. As with the article of manufacture, the kit comprises a container and a label or package insert on or associated with the container. For example, the container holds a composition comprising at least one anti-CD73 antibody and/or variant or mutant (or fragment) thereof provided herein. Additional containers may be included that contain, e.g., diluents and buffers, control antibodies. The label or package insert may provide a description of the composition as well as instructions for the intended in vitro or diagnostic use.

Another embodiment provided herein is an article of manufacture containing materials useful for the treatment of a disclosed cancer. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating the condition and may have a sterile access port (for example the container may be an intravenous solution bag or a vial having a stopper pierceable by a hypodermic injection needle). At least one active agent in the composition is an anti-CD73 antibody and/or variant or mutant (or fragment) thereof provided herein. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating cancer (such as head and neck cancer, lung cancer, or colorectal cancer).

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Now having described the aspects of the present disclosure, in general, the following Examples describe some additional aspects of the present disclosure. While aspects of the present disclosure are described in connection with the following examples and the corresponding text and FIGS., there is no intent to limit aspects of the present disclosure to this description. On the contrary, the intent is to cover all alternatives, modifications, and equivalents included within the spirit and scope of the present disclosure.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

TABLE 6

| Sources of materials: unless otherwise specified below, all are common commercially available reagents | |
| --- | --- |
| Anti-CD73 ref-1 antibody | provided by Henlius Biotech Co., Ltd., Taiwan, China, batch No.:1609211007ACA, specification: 14.1 mg/mL, stored at −80° C.. |
| Anti-CD73 ref-2 antibody | provided by Henlius Biotech Co., Ltd., Taiwan, China, batch No.:1705250609AC, specification: 6.6 mg/mL, stored at −80° C.. |
| HLX01 (anti-CD20) | provided by Shanghai Henlius Biotech, Inc., batch No.: R20110402, specification: 10 mg/mL, stored at 4° C.. |

TABLE 6-continued

| Sources of materials: unless otherwise specified below, all are common commercially available reagents | |
| --- | --- |
| APCP | provided by Sigma-Aldrich, Cat. NO.: M3763-10MG, batch No.: SLBS7778, stored at room temperature |
| MDA-MB-231 (human breast cancer) cells | provided by Bioresource Collection and Research Center (BCRC), Taiwan, China |
| NCI-H292 (human mucoepidermoid lung cancer) | provided by ATCC |
| mouse breast cancer 4T1 cells | provided by ATCC |
| monkey kidney epithelial LLC-MK2 cells | provided by Bioresource Collection and Research Center (BCRC), Taiwan, China |

Example 1. Preparation of Anti-Cd73 Antibodies and Variants

Human Fab naïve phage display library was panned with human CD73-ECD/His. After four rounds of panning with biotinylated huCD73-ECD/His coupled to streptavidin-coated magnetic Dynabeads® M-280 (Thermo Fisher Scientific #11205D), fifty-two possible clones with CD73-binding and immobilized CD73 enzyme blocking activity were selected and four kinds of sequence were determined (N1 to N4). The selected variable sequences were then cloned into L234F, L235E, P331S mutant of human IgG1 Fc backbone to become full-length antibodies for in vitro functional analysis (CD73-binding, CD73 enzyme activity blocking, antibody-mediated CD73 internalization). N1, N2 and N4 leads were also cloned into human wild-type or C219S mutant IgG2 Fc backbone. According to the in vitro efficacy and in vivo efficacy test (MDA-MB-231 xenograft model), N1 and N4 were selected for following affinity maturation and wtIgG2 backbone was determined.

Antibodies lead N1 and lead N4 were used in in vitro phage display-based affinity maturation experiments to generate additional clones with improved CD73-binding and CD73 enzyme blocking activity performance. CDR-L1/CDR-L3/CDR-H3 (focusing on 3 CDRs) nucleic acid libraries of N1 lead were generated via PCR, cloned into a phage display vector, and transformed into E. coli TG1 cells to produce a library of phages. After three rounds of panning with biotinylated huCD73-ECD/His, fifteen kinds of Fab clones with different sequences were screened via binding assay and enzyme blocking assay, and two Fabs (N1 #2 and N1 #9) were found to have better efficacy. About affinity maturation of N4 lead, first, CDR-L3/CDR-H1/CDR-H3 nucleic acid libraries were generated to produce a library of phages. After three rounds of panning, six kinds of Fab clones (N4 #1 to N4 #6) with different sequences were screened via binding assay and enzyme blocking assay. Second, CDR-L1/CDR-L2/CDR-H2 nucleic acid libraries of N4 #1, N4 #4, N4 #5 and N4 #6 clones were generated to produce a library of phages. After three rounds of panning, N4 #4-3, N4 #6-2, N4 #6-3, N4 #6-4, N4 #6-5 clones were selected with better binding and enzyme blocking activity.

After affinity maturation, N1 #2, N1 #9, N4 #5, N4 #6, N4 #4-3, N4 #6-2, N4 #6-3, N4 #6-4, N4 #6-5 were cloned into human IgG2 Fc backbone to become full-length antibodies and subjected to in vitro efficacy test (including CD73 protein-binding ELISA, CD73-expressing tumor cell binding, immobilized and cellular CD73 enzyme blocking, antibody-mediated CD73 internalization) and in vivo efficacy test (NCI-H292 xenograft model), and N1 #2, N1 #9, N4 #6-3, N4 #6-4 clones were selected. According to the sequence alignment and the CMC stability, these four clones were modified to create N1 #2-P, N1 #9-PH, N4 #6-3-P, N4 #6-4-P. N1 #9-PH has better soluble CD73 enzyme blocking efficacy, and N4 #6-3-P, N4 #6-4-P could induce surface CD73 internalization. N1 #9-PH, N4 #6-3-P, N4 #6-4-P can relieve the AMP-mediated T cell suppression and have anti-tumor activity against MDA-MB-231 xenografts in vivo. In addition, N4 #6-4-P can induce CD73 downmodulation and block CD73 enzyme activity in xenograft tumors and has better anti-tumor activity than other anti-CD73 antibodies in NCI-H292 xenograft model.

The amino acid sequence alignment of light chain and heavy chain variable region of anti-CD73 selected leads N1, N2 and N4 from naïve phage panning are presented in FIG. 1A and FIG. 1B, respectively. The amino acid sequence alignment of light chain variable region of N1 and N4 variants derived from affinity maturation are shown in FIG. 9 with Kabat defined CDRs (Complementary Determining Regions) being underlined and marked in bold, and the amino acid sequence alignment of heavy chain variable region of N1 and N4 variants derived from affinity maturation are shown in FIG. 10 with Kabat defined CDRs (Complementary Determining Regions) being underlined and marked in bold. These selected variable sequences were then cloned into human IgG2 Fc backbone to become full-length antibodies. The amino acid sequences of the light chain constant region and the heavy chain constant region of the human antibody can be selected as follows (no limitation on the amino acid sequences of the light and heavy chain variable regions herein):

wtIgG2 isotype heavy chain constant region (SEQ ID NO: 112)

mtIgG2 isotype heavy chain constant region (SEQ ID NO: 113)

tmtIgG1 isotype heavy chain constant region (SEQ ID NO: 114)

Light chain constant region (SEQ ID NO: 115)

N1 #2-P heavy chain (SEQ ID NO: 116)

N1 #9-PH heavy chain (SEQ ID NO: 117)

N4 #6-3-P_heavy Chain (SEQ ID NO:118)

N4 #6-4-P heavy chain (SEQ ID NO: 119).

FIG. 14 shows the amino acid sequence alignment of light chain of N1 and N4 top variants with Kabat defined CDRs (Complementary Determining Regions) being underlined and marked in bold, and FIG. 15 shows the amino acid sequence alignment of heavy chain variable region of N1 and N4 top variants with Kabat defined CDRs (Complementary Determining Regions) being underlined and marked in bold. These sequences were then cloned into human IgG2 Fc backbone to become full-length antibodies.

Example 2. CD73 Binding Ability of Selected Antibodies

ELISA assays were performed to assess the binding of selected antibodies to recombinant human CD73-ECD/His proteins. Thirty nanograms per well of goat anti-human IgG Fd (or Fc) antibodies were coated on 96-well EIA microplate overnight at 4° C. After blocking with 5% skim milk (in PBS), serially diluted antibodies were added and incubated at RT for 1 hour. The unbound antibodies were removed, and wells were washed with 1×PBST containing 0.05% Tween 20 for three times. Thirty nanograms per well of biotin-labeled CD73-ECD/His proteins were added to the wells and incubated at RT for another 1 hour. The unbound biotin-labeled CD73-ECD/His were washed with 1×PBST containing 0.05% Tween 20 for three times. The avidin-HRP was then added to the wells and incubated at RT for 30 minutes. Excess secondary antibodies were removed by washing with 1×PBST containing 0.05% Tween 20 for three times. After washing, plates were developed using TMB. The absorbance was read at the wavelength of 450 nm by microplate reader.

Figure 2A:
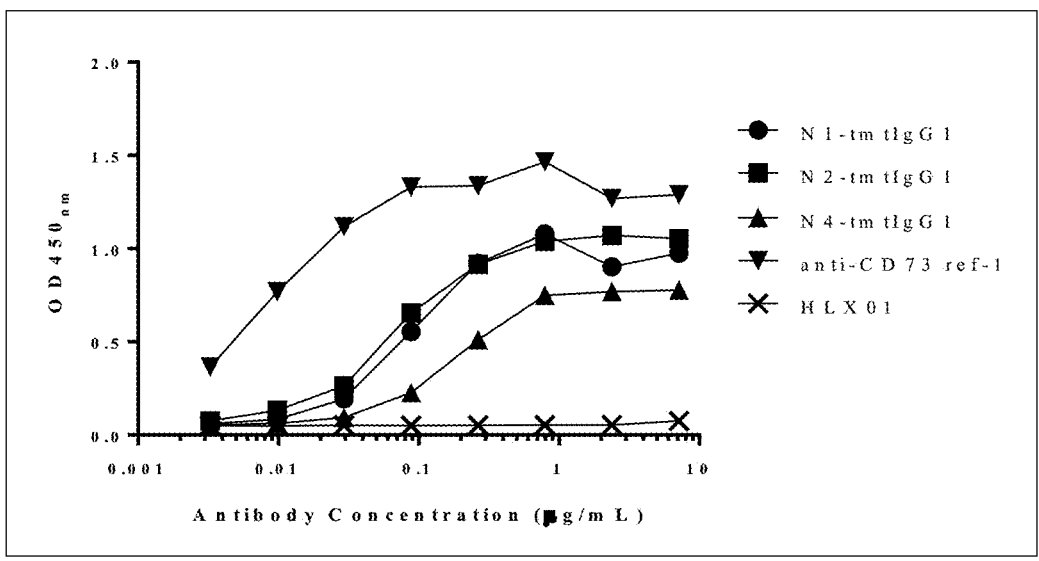
FIGS. 2A-2C. CD73 binding of selected antibodies. Selected antibodies were tested the binding to recombinant human CD73 proteins by ELISA (FIG. 2A), CD73-expressing human tumor cells MDA-MB-231 (human breast adenocarcinoma) cells (FIG. 2B), and NCI-H292 (human mucoepidermoid pulmonary carcinoma) cells (FIG. 2C) by flow cytometry. Anti-CD73 ref-1 antibody and HLX01 (anti-CD20) were used as the positive and negative control respectively.

Selected anti-CD73 antibodies were tested the binding to recombinant human CD73 proteins by ELISA, and the binding data are presented in FIG. 2A.

Figure 2B:
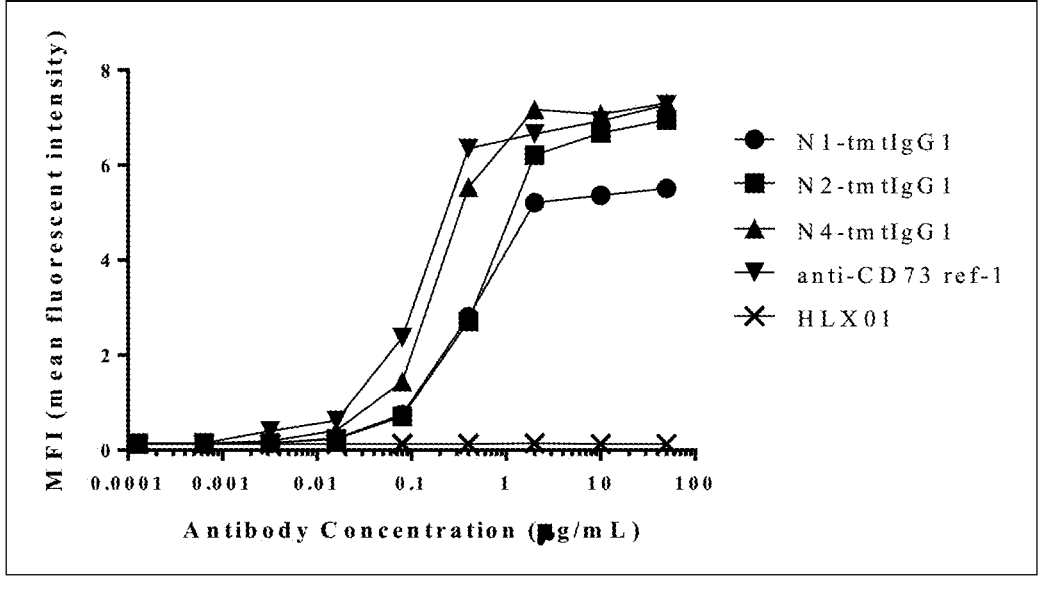
Figure 2C:
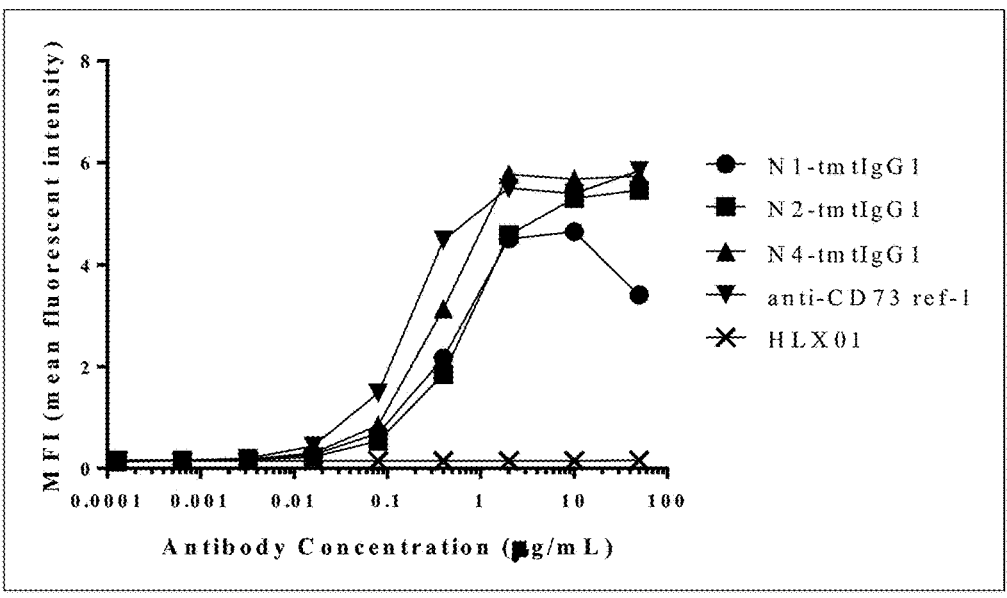

Whole cell binding ability of anti-CD73 antibodies were tested by incubating the MDA-MB-231 or NCI-H292 cells with the serial-diluted antibodies in FACS buffer (PBS with 2% FBS) at 4° C. for 30 minutes. Cells were washed with FACS buffer and the binding was detected with FITC-labeled goat anti-human IgG (H+L) antibodies (or PE-labeled goat anti-human IgG Fcγ) at 4° C. for another 30 minutes. The binding of antibodies to cell surface was measured by the mean fluorescent intensity (MFI) of staining. Flow cytometric analyses were performed using the Cytomics FC500 or CytoFLEX flow cytometry (Beckman Coulter Inc.). FIGS. 2B and 2C show selected anti-CD73 antibodies binding to CD73-expressing human tumor cells MDA-MB-231 (human breast adenocarcinoma) cells (FIG. 2B), and NCI-H292 (human mucoepidermoid pulmonary carcinoma) cells (FIG. 2C).

In these studies, anti-CD73 ref-1 antibody and HLX01 (anti-CD20) were used as the positive and negative control respectively. These data suggest all selected anti-CD73 antibodies can bind to both human CD73 recombinant proteins and CD73-expressing human tumor cells.

FIGS. 11A-11B also show CD73 binding of N1 and N4 variants. Selected variants were tested the binding to CD73-expressing MDA-MB-231 (FIG. 11A) and NCI-H292 (FIG. 11B) cells by flow cytometry. HLX01 (anti-CD20) was used as the negative control. These data indicate that, after affinity maturation, all of N1 and N4 variants can bind to CD73-expressing human tumor cells. N4 variants have better CD73 binding ability than N1 variants in these two cell lines. The rank of the whole cell binding ability is: N4 #5, N4 #6-4, N4 #6-5>N4 #6-2>N4 #4-3, N4 #6, N4 #6-3, N1 #9>N1 #2.

FIGS. 16A-16C show CD73 binding ability of N1 and N4 top variants. Anti-CD73 antibodies were tested the binding to recombinant human CD73 proteins by ELISA (FIG. 16A) and CD73-expressing human tumor cells, MDA-MB-231 (FIG. 16B) and NCI-H292 (FIG. 16C), by flow cytometry. Anti-CD73 ref-1 and anti-CD73 ref-2 antibodies were used as the positive controls, while HLX01 (anti-CD20) was used as the negative control. These data indicate that N4 #6-3-P, N4 #6-4-P, and N1 #9-PH bind with comparable affinity to recombinant CD73 and surface CD73 on MDA-MB-231 cells. The binding of N1 #9-PH to CD73-expressing NCI-H292 cells is slightly better than that of N4 #6-3-P and N4 #6-4-P.

Example 3. Effects of Anti-Cd73 Leads on Soluble and Cellular CD73 Enzyme Activity Anti-CD73 antibodies were tested for their ability to inhibit the enzyme activity of human recombinant CD73 protein and cell surface CD73. The CD73-catalyzed hydrolysis of AMP to adenosine and inorganic phosphate was analyzed by measuring the ATP-dependent oxidation of luciferin which is inhibited by AMP (CellTiter-Glo® assay; Promega). Fifteen nanograms of recombinant human CD73-ECD/His proteins were incubated with serially diluted anti-CD73 antibodies, ATP (final concentration 100 μM) and AMP (final concentration 300 μM) in the assay buffer (25 mM Tris, 5 mM $MgCl_2$, pH 7.46) at 37° C. The same volume of CellTiter-Glo® reagent was added to the reaction and mixed for 2 mins in white 96-well microplate. After a 10-min incubation, luminescence was measured.

CD73-expressing cells (5E3-1E4 cells/well) were resuspended in culture media and plated in 96-well microplate (or pre-seeded for 24 hours). Three-fold (or five-fold) serial dilutions of antibodies were added to each culture. After incubating at 37° C. for 15 minutes, AMP (final concentration 225 μM) was added and incubated for 4-20 hours. After centrifugation, culture supernatants were collected, put in white 96-well microplate and added ATP to the final concentration of 100 μM for a 2-min incubation. The same volume of CellTiter-Glo® reagent was added to each well and mixed for 2 mins. After a 10-min incubation, luminescence was measured.

Figure 3A:
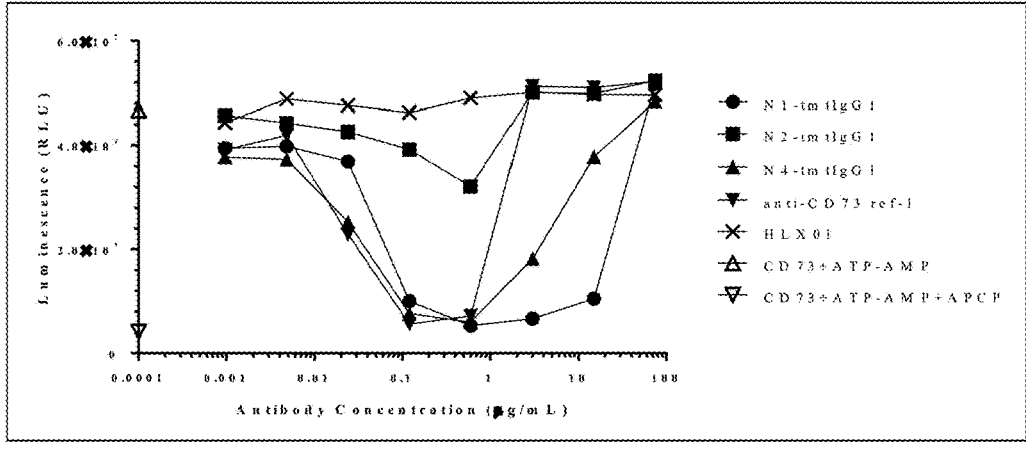
FIGS. 3A-3B. Effects of anti-CD73 leads on soluble CD73 enzyme activity and cellular CD73 enzyme activity. Anti-CD73 antibodies were tested for their ability to inhibit the enzyme activity of human recombinant CD73 protein and cell surface CD73. Recombinant CD73 proteins (FIG. 3A) and NCI-H292 cells (FIG. 3B) were incubated with anti-CD73 antibodies, ATP, and AMP. The AMP concentration in the sample was determined using the CellTiter-Glo® assay (purchased from Promega Corporation). CellTiter-Glo® measures the ATP-dependent oxidation of luciferin, which is inhibited by AMP. The luminescence reading value indicates the CD73 enzyme activity. Anti-CD73 ref-1 antibody and APCP were used as the positive controls, while HLX01 (anti-CD20) was used as the negative control.
Figure 3B:
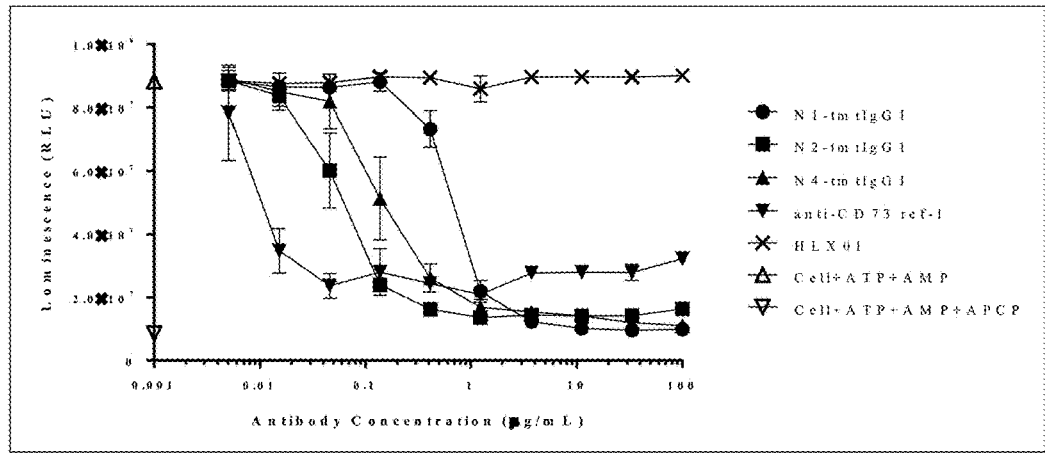

The data showing the effects of anti-CD73 leads on soluble and cellular CD73 enzyme activity are presented in FIGS. 3A and 3B respectively. These data suggest that all selected antibodies can inhibit the enzyme activity of both human soluble and surface CD73. In soluble CD73 enzyme activity assay, a loss of inhibition was observed when IgG was in stoichiometric excess relative to sCD73. This so-called "hook effect" can result from monovalent antibody binding driven by Fab arms on the same IgG molecule competing for limiting binding sites on the target antigen.

Anti-CD73 leads N1, N2, N4 with different IgG isotypes were tested for their ability to inhibit the cellular CD73 enzyme activity. MDA-MB-231 cells were incubated with anti-CD73 antibodies. ATP, AMP and CellTiter-Glo® reagent were added and the luminescence was recorded. APCP was used as the positive control in the enzyme activity assay. The effects of these anti-CD73 leads with different IgG Fc regions on cellular CD73 enzyme activity are shown in FIG. 6A (lead N1), 6B (lead N2), and 6C (lead N4).

These data indicate that the wtIgG2 isotype of N1 clone has better blocking activity than tmtIgG1 and mtIgG2 isotypes. The tmtIgG1 isotype of N2 clone has better blocking activity than wtIgG2 and mtIgG2 isotypes. The N4 with wtIgG2 isotype shows the best blocking activity than tmtIgG1 and mtIgG2 isotypes. The tmtIgG1 isotype has the following Fc site-specific changes: L234F, L235E, and P331S.

FIGS. 17A-17C also show the effects of N1 and N4 top variants on soluble CD73 enzyme activity (FIG. 17A) and cell surface CD73 enzyme activity (FIGS. 17B and 17C). Anti-CD73 antibodies were tested for their ability to inhibit the human recombinant CD73 protein and cell surface CD73 enzyme activity. Recombinant CD73 proteins (FIG. 17A), MDA-MB-231 (FIG. 17B) and NCI-H292 (FIG. 17C) cells were incubated with anti-CD73 antibodies. ATP, AMP and CellTiter-Glo® were added and the luminescence was recorded. Anti-CD73 ref-1 antibody, anti-CD73 ref-2 antibody, and APCP were used as the positive controls. HLX01 (anti-CD20) was used as the negative control.

The data presented in FIGS. 17A-17C show that the ability of N1 #9-PH to inhibit soluble CD73 enzyme activity was better than that of N4 #6-3-P and N4 #6-4-P. However, N1 #9-PH and N4 #6-4-P showed comparable blocking activity on cell surface CD73 enzyme activity.

Example 4. Antibody-Mediated CD73 Internalization of Anti-CD73 Leads

Tumor cells (5E4 to 1E5 cells/well) were suspended in culture media and incubated with anti-CD73 antibodies at different concentrations for 4 hours. After removing culture media, cells were suspended in FACS buffer (PBS with 2% FBS) and incubated with mouse anti-human CD73 antibodies (4G4) at 4° C. for 30 minutes. The cells were washed with FACS buffer and incubated with FITC-labeled goat anti-mouse IgG (H+L) antibodies or Alexa488-labeled goat anti-mouse IgG Fcγ antibodies. Flow cytometric analyses were performed using the Cytomics FC500 or CytoFLEX flow cytometry (Beckman Coulter Inc.). Anti-CD73 ref-1 antibody and HLX01 (anti-CD20) were used as the positive and negative control respectively.

Figure 4:
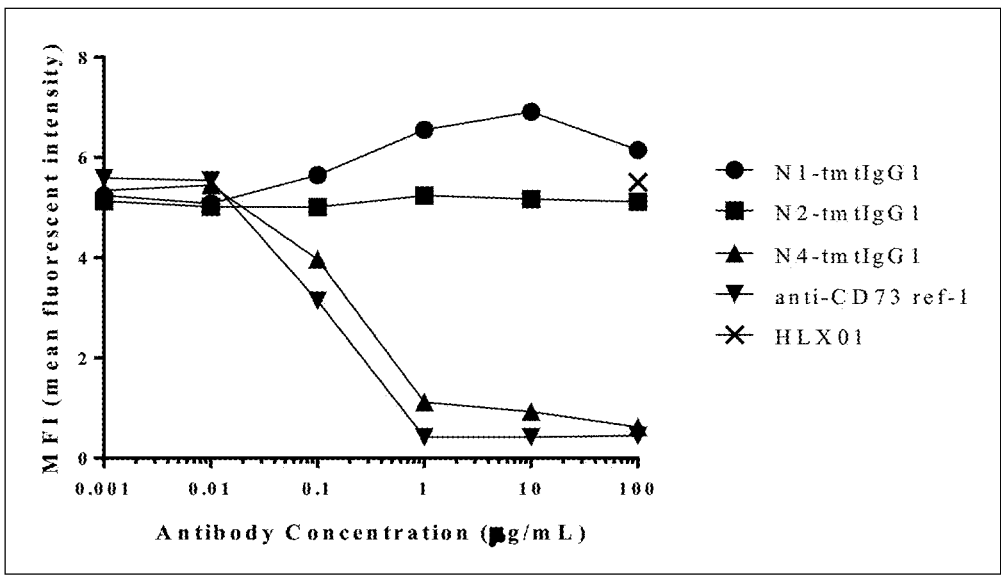
FIG. 4. Antibody-mediated CD73 internalization of anti-CD73 leads. Cell surface expression of CD73 was measured by flow cytometry after anti-CD73 antibody treatment. Anti-CD73 ref-1 antibody and HLX01 (anti-CD20) were used as the positive and negative control respectively.

The data presented FIG. 4 indicate only N4-tmtIgG1 can induce CD73 internalization. N1-tmtIgG1 and N2-tmtIgG1 cannot induce CD73 internalization.

FIG. 7 also illustrates antibody-mediated CD73 internalization of anti-CD73 antibodies with different IgG Fc regions. After incubating cells with different IgG isotypes of N1 (FIG. 7A), N2 (FIG. 7B), and N4 (FIG. 7C), the cell surface expression of CD73 was measured by flow cytometry. Anti-CD73 ref-1 antibody and HLX01 (anti-CD20) were used as the positive and negative control respectively. The data show that N4, but not N1 and N2, can induce CD73 internalization. There is no obvious difference between different IgG isotypes.

FIG. 13 also shows antibody-mediated CD73 internalization of N1 and N4 variants. The NCI-H292 cells were incubated with N1 and N4 variants, and the cell surface expression of CD73 was measured by flow cytometry. Anti-CD73 ref-1 antibody and anti-CD73 ref-2 antibody were used as the positive controls, while HLX01 (anti-CD20) was used as the negative control. The data indicate that, after affinity maturation, N4 variants can induce CD73 internalization and N1 variants still cannot induce CD73 internalization.

FIGS. 18A and 18B also show antibody-mediated CD73 internalization of N1 and N4 top variants. MDA-MB-231 (FIG. 18A) and NCI-H292 (FIG. 18B) cells were incubated with anti-CD73 N1 and N4 variants. After the incubation, the cell surface expression of CD73 was measured by flow cytometry. Anti-CD73 ref-1 and anti-CD73 ref-2 antibodies were used as the positive controls, while HLX01 (anti-CD20) was used as the negative control. These data indicate that N4 #6-3-P and N4 #6-4-P can induce CD73 internalization in both CD73-expressing cancer cells.

Example 5. CD73 Binding of Selected Antibodies with Different Igg Fc Region

The binding of anti-CD73 antibodies to cell surface CD73 were tested by incubating the MDA-MB-231 cells with the serially diluted biotin-labeled anti-CD73 antibodies in FACS buffer (PBS with 2% FBS) at 4° C. for 30 minutes. The cells were washed with FACS buffer and the binding was detected with streptavidin-FITC at 4° C. for 30 minutes. Flow cytometric analyses were performed using the Cytomics FC500 (Beckman Coulter Inc.).

The variable sequences of N1, N2 and N4 were cloned into human wild-type or C219S mutant IgG2 Fc backbone. Different IgG isotypes of N1 (FIG. 5A), N2 (FIG. 5B), N4

(FIG. 5C) were tested the binding to CD73-expressing human MDA-MB-231 cells by flow cytometry. Anti-CD73 ref-1 antibody and HLX01 (anti-CD20) were used as the positive and negative control respectively.

Figure 5A:
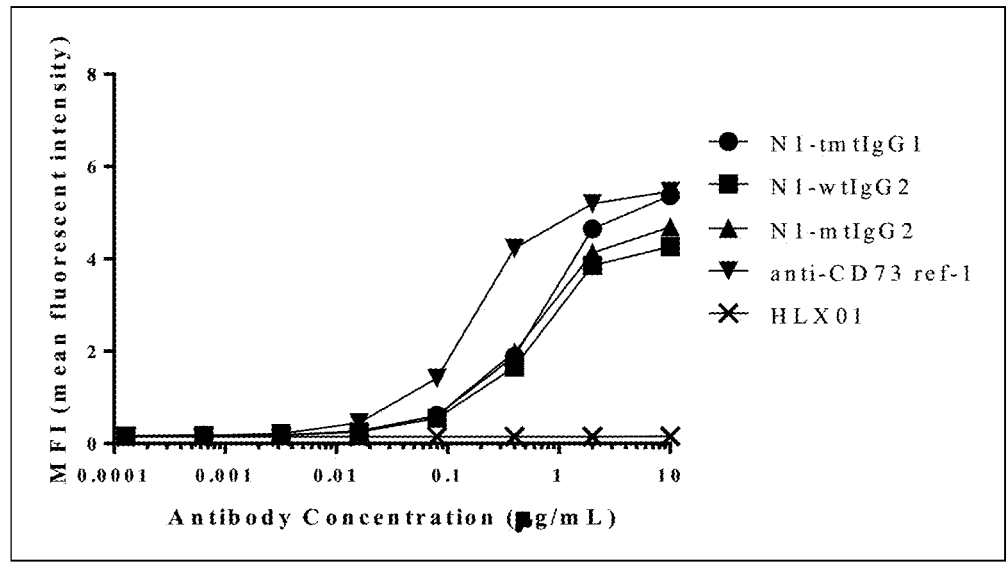
FIGS. 5A-5C. CD73 binding of selected antibodies with different IgG Fc regions. The variable sequences of N1, N2 and N4 were also cloned into human wild-type or C219S mutant IgG2 Fc backbone. Different IgG isotypes of N1 (FIG. 5A), N2 (FIG. 5B), N4 (FIG. 5C) were tested the binding to CD73-expressing human MDA-MB-231 cells by flow cytometry. Anti-CD73 ref-1 antibody and HLX01 (anti-CD20) were used as the positive and negative control respectively.
Figure 5B:
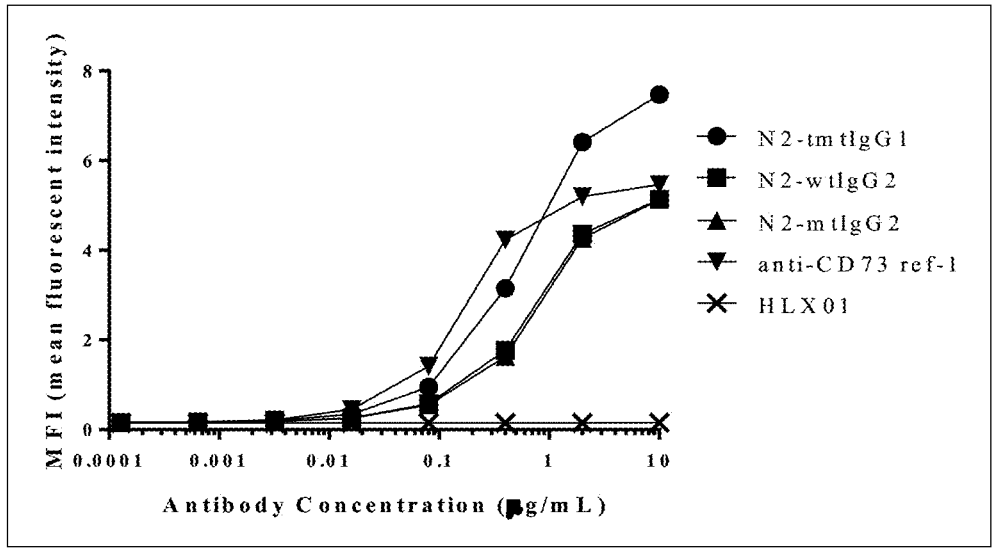
Figure 5C:
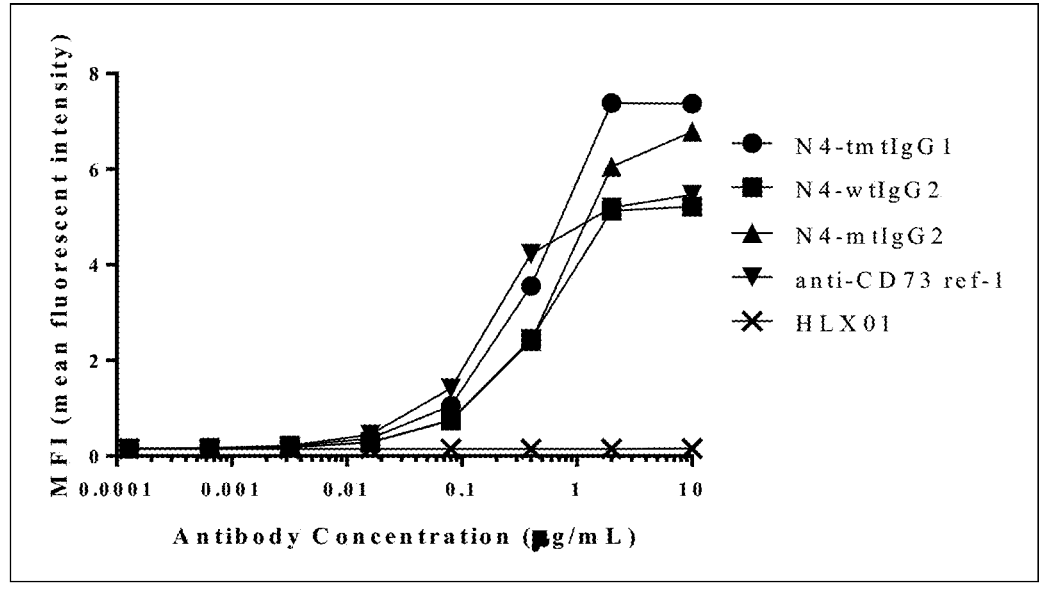

The data presented in FIGS. 5A-5C indicate that there is no difference between different IgG isotypes of N1 in CD73-binding ability. The data also show that N2 clone, tmtIgG1 isotype has better CD73-binding activity than wtIgG2 and mtIgG2 isotypes, and the N4 clone, tmtIgG1 isotype has better CD73-binding activity than wtIgG2 and mtIgG2 isotypes.

Example 6. Tumor Growth Inhibition Activity of Anti-Cd73 Leads in MDA-MB-231 (Human Triple-Negative Breast Cancer) Xenograft Mouse Model The in vivo activity of anti-human CD73 antibodies was investigated in xenograft mouse models using immunocompromised NOD/SCID (non-obese diabetic/severe combined immunodeficiency) mice. A total of 1E7 CD73-expressing human triple-negative breast cancer MDA-MB-231 cells in 100 μL of PBS were mixed with 100 μL of Matrigel (Corning, CA, USA) (in a 1:1 ratio) and subcutaneously implanted into both side flanks of female NOD/SCID mice (Biolasco, Taipei, Taiwan). When tumor size reached 150-300 mm$^3$ (day 14 after tumor inoculation), 5 mg/kg anti-CD73 antibodies or 10 mL/kg placebo were administered intraperitoneally twice per week or at indicated time. Tumors were observed and measured until day 45. Tumor volume was defined as TV (tumor volume)=(length× width$^2$)/2.

Tumor growth curves were shown in FIG. 8A. The individual tumor volume at day 45 was presented in FIG. 8B. All data points are the means±SEM. The data demonstrate that all anti-CD73 antibodies have anti-tumor activity in MDA-MB-231 xenograft model (TGI≥50%) except the tmtIgG1 isotype of N1, N2 and N4 clones. N1-wtIgG2, N1-mtIgG2, N2-wtIgG2, and N2-mtIgG2 almost completely inhibit tumor growth.

FIG. 20 also shows tumor growth inhibition activity of N1 and N4 top variants in MDA-MB-231 (human triple-negative breast cancer) xenograft mouse model. Mice (n=5 mice/group) were subcutaneously engrafted with MDA-MB-231 cells. The first dose of test article was administered 7 days after tumor inoculation when the engrafted tumor size reached about 100 mm$^3$. Mice were intraperitoneally treated with 10 mg/kg and 2 mg/kg of antibodies twice per week for 5-6 weeks. All data points are the means±SEM. These data demonstrates that all N1 and N4 top variants have anti-tumor activity against MDA-MB-231 xenografts in vivo. N4 #6-3-P, N4 #6-4-P and N1 #9-PH have better anti-tumor activity than anti-CD73 reference antibody.

Example 7. Effects of N1 and N4 Variants on Immobilized CD73 Enzyme Activity N1 and N4 variants were tested for their ability to inhibit the immobilized CD73 enzyme activity. Three hundred nanograms per well of goat anti-human IgG Fd antibodies were coated on white, high-affinity 96-well microplate overnight at 4° C. After blocking with 5% skim milk (in PBS), serially diluted antibodies were added and incubated at RT for 1 hour. The unbound antibodies were removed, and wells were washed with 1×PBST containing 0.05% Tween 20 for three times. Twenty-five microliter of 100 ng/mL CD73-ECD/His proteins in the assay buffer (25 mM Tris, 5 mM MgCl$_2$, pH 7.46) were added to the wells and incubated at RT for another 1 hour. Twenty-five microliter of 66 µM ATP and 200 µM AMP mixture were added and incubated at 37° C. for 9 minutes. The same volume of CellTiter-Glo® reagent was added to the reaction mixture and mixed contents for 2 mins (in white 96-well microplate). After a 10-min incubation, luminescence was measured. Anti-CD73 ref-1 antibody, anti-CD73 ref-2 antibody were used as the positive controls, while HLX01 (anti-CD20) was used as the negative control.

Effects of N1 and N4 variants on immobilized CD73 enzyme activity are shown in FIG. 12. The data indicate that, after affinity maturation, all of N1 and N4 variants can inhibit CD73 enzyme activity. The CD73 enzyme blocking activity of N1 variants were better than that of N4 variants and anti-CD73 ref-2 antibody, but comparable to that of anti-CD73 ref-1 antibody. Blocking immobilized CD73 enzyme activity: N1 #2, N1 #9>N4 #6-4, N4 #6-5>N4 #4-3, N4 #6-2>N4 #6-3, N4 #5>N4 #6.

Example 8. Reversing Suppressive Effects of Amp on T Cell Activity by N1 and N4 Top Variants CD73 catalyzes the extracellular generation of adenosine from adenosine monophosphate (AMP). Adenosine suppresses immune responses, including those of T cells, NK cells and dendritic cells through activation of A2aR and A2bR receptors. In addition to CD73 enzyme inhibition and internalization, the functional effect on T-cell proliferation of CD73 inhibition by anti-CD73 antibodies was examined.

Human T-cells were isolated from peripheral blood mononuclear cells (PBMCs) using the Magni Sort Human T cell Enrichment Kit (eBioscience, Inc.) and suspended in the complete media (RPMI-1640 with 10% FBS) containing 50 IU/mL of recombinant human IL-2 (eBioscience, Inc.). T cells (5E4 cells/reaction) in a volume of 100 µL were mixed with Dynabeads™ Human T-Activator CD3/CD28 (Thermo Fisher Scientific) at 1:0.5 cell-to-bead ratio. AMP (1 mM) and serially diluted antibodies were added to each reaction in a volume of 100 µL. The reaction containing no activation beads (unstimulated group), CD3/CD28 beads alone (stimulated group), or CD3/CD28 beads plus AMP (AMP-mediated inhibition group) were used as assay controls. Anti-CD73 ref-1 antibody, anti-CD73 ref-2 antibody and APCP were used as positive controls. HLX04 (anti-VEGF) was used as a negative control. The cells were cultured for 4 days at 37° C. On day 4, the cells were collected, washed, and resuspended in fresh RPMI-1640 media. T cell proliferation was analyzed by CellTiter-Glo® assay. The culture supernatants were collected for cytokine measurement. The level of IFN-γ was measured using Human IFN-γ ELISA MAX™ Deluxe kits (BioLegend, Inc.).

Reversing suppressive effects of AMP on T cell activity by N1 and N4 top variants are shown in FIGS. 19A and 19B. Proliferation of CD3 T cells was followed by CellTiter-Glo® assay (FIG. 19A), and the IFN-γ secretion was measured using Human IFN-γ ELISA MAX™ Deluxe kits (FIG. 19B). Anti-CD73 ref-1 antibody, anti-CD73 ref-2 antibody and APCP were used as positive controls. HLX04 (anti-VEGF) was used as a negative control. The data illustrated in FIGS. 19A and 19B suggest that N1 and N4 top variants are able to enhance T-cell proliferation and IFN-γ secretion in a dose-dependent manner. The data further indicate that N4 #6-3-P, N4 #6-4-P and N1 #9-PH can relieve the AMP-mediated T cell suppression.

Example 9. Tumor Growth Inhibition Activity of N1 and N4 Top Variants in NCI-H292 (Human Mucoepidermoid Pulmonary Carcinoma) Xenograft Mouse Model The in vivo activity of anti-human CD73 antibodies was investigated in xenograft mouse models using immunocompromised BALB/c Nude mice. A total of 5E6 NCI-H292 cells in 100 µL of PBS were mixed with 100 µL of Matrigel (Corning, CA, USA) (in a 1:1 ratio) and subcutaneously implanted into both side flanks of male BALB/c Nude mice (Biolasco, Taipei, Taiwan). When tumor size reached 150-300 mm$^3$, anti-CD73 antibodies or placebo were administered intraperitoneally twice per week for 3 weeks. Tumors were observed and measured twice a week. Tumor volume was defined as TV (tumor volume)=(length×width$^2$)/2.

FIG. 21 shows the tumor growth inhibition activity of N1 and N4 top variants in NCI-H292 (human mucoepidermoid pulmonary carcinoma) xenograft mouse model. Mice (n=5 mice/group) were subcutaneously engrafted with NCI-H292 cells. The first dose of test article was administered 3 days after tumor inoculation. Mice were intraperitoneally treated with 50, 10 and 2 mg/kg of antibodies twice per week for 3 weeks. All data points are the means±SEM. The data demonstrate that N4 #6-4-P has better anti-tumor activity than other anti-CD73 antibodies in NCI-H292 xenograft model.

Example 10. Effects of N1 and N4 Top Variants on Cellular CD73 Enzyme Activity In NCI-H292 Xenograft Tumors A total of 5E6 NCI-H292 cells in 100 µL of PBS were mixed with 100 µL of Matrigel (Corning, CA, USA) (in a 1:1 ratio) and subcutaneously implanted into both side flanks of male BALB/c Nude mice (Biolasco, Taipei, Taiwan) 4 days before antibody administration. Mice were intraperitoneally treated with 30 mg/kg antibodies, APCP and placebo at day 0 and tumors were collected at day 1, 3 and 7. Tumor cells (2E4) were resuspended in the assay buffer (25 mM Tris, 5 mM MgCl$_2$, pH 7.46) and treated with ATP (final concentration 100 UM) and AMP (final concentration 300 µM) at 37° C. for 45 minutes. The same volume of CellTiter-Glo® reagent was added to the reaction mixture and mixed contents for 2 mins (in white 96-well microplate). After a 10-min incubation, luminescence was measured.

FIG. 22 shows the effects of N1 and N4 top variants on cellular CD73 enzyme activity in NCI-H292 xenograft tumors. N1 and N4 top variants were tested for their ability to inhibit the CD73 enzyme activity in NCI-H292 xenograft model. Mice (n=4 mice/group) were subcutaneously engrafted with NCI-H292 cells 4 days before the antibody treatment. Antibodies, APCP, and placebo were intraperitoneally injected at day 0. Tumors were resected at days 1, 3 and 7 after antibody administration. The CD73 enzyme activity in tumors were measured by CellTiter-Glo® assay.

The data demonstrate that N1 and N4 top variants can inhibit CD73 enzyme activity in NCI-H292 xenograft model. N4 #6-3-P and N4 #6-4-P blocked CD73 enzyme activity in tumors better than N1 #9-PH and anti-CD73 reference antibody.

Example 11. Effects of N1 and N4 Top Variants on Cd73 Expression and Cellular CD73 Enzyme Activity in MDA-MB-231 Xenograft Tumors A total of 1E7 MDA-MB-231 cells in 100 µL of PBS were mixed with 100 µL of Matrigel (Corning, CA, USA) (in a 1:1 ratio) and subcutaneously implanted into both side flanks of female NOD/SCID mice (Biolasco, Taipei, Taiwan) 7 days before antibody administration. Mice were intraperitoneally treated with 2 mg/kg antibodies and 10 mL/kg placebo at day 0. Tumors were collected at day 1, 3 and 7. To measure the surface CD73 expression level, 5E4 tumor cells were resuspended in FACS buffer (PBS with 2% FBS) and treated with anti-human and anti-mouse FcR blocking reagent at 4° C. for 30 minutes. After centrifugation, cells were then incubated with mouse anti-human CD73 antibodies (4G4) at 4° C. for 30 minutes. The cells were washed with FACS buffer and incubated with Alexa 488-labeled goat anti-mouse IgG Fcγ antibodies at 4° C. for another 30 minutes. Flow cytometric analyses were performed using the Cyto-FLEX flow cytometry (Beckman Coulter Inc.). A total of 2E4 tumor cells were resuspended in the assay buffer (25 mM Tris, 5 mM $MgCl_2$, pH 7.46) for CD73 enzyme activity measurement. The cell suspensions were treated with ATP (final concentration 100 μM) and AMP (final concentration 300 μM) at 37° C. for 45 minutes. The same volume of CellTiter-Glo® reagent was added to the reaction mixture and mixed for 2 mins (in white 96-well microplate). After a 10-min incubation, luminescence was measured.

FIGS. 23A and 23B show the effects of N1 and N4 top variants on CD73 expression and cellular CD73 enzyme activity in MDA-MB-231 xenograft tumors. The CD73 expression was measured by the mean fluorescent intensity (MFI) of staining (FIG. 23A) and the CD73 enzyme activity in tumors were measured by CellTiter-Glo® assay (FIG. 23B). The data demonstrate that, compared to the placebo group, N4 #6-4-P can downregulate surface CD73 expression and inhibit CD73 enzyme activity in MDA-MB-231 xenograft mouse model.

Example 12. Cross-Binding of N1 and N4 Top Variants to Mouse And Monkey CD73-Expressing Cells Binding of anti-CD73 antibodies was assessed by incubating the 4T1 or LLC-MK2 cells (1E5 cells/test) with the serially diluted antibodies in FACS buffer (PBS with 2% FBS) at 4° C. for 30 minutes. The cells were washed with FACS buffer and the binding was detected with FITC-labeled goat anti-human IgG (H+L) antibodies at 4° C. for another 30 minutes. The binding of antibodies to cell surface was measured by the mean fluorescent intensity (MFI) of staining. Flow cytometric analyses were performed using the Cytomics FC500 or CytoFLEX flow cytometry (Beckman Coulter Inc.).

FIGS. 24A and 24B illustrate cross-binding of N1 and N4 top variants to mouse and monkey CD73-expressing cells. Anti-CD73 antibodies were tested for the binding to CD73-expressing mouse mammary carcinoma 4T1 cells (FIG. 24A) and monkey kidney epithelial LLC-MK2 cells (FIG. 24B) by flow cytometry. HLX01 was used as the negative control. These data indicate that N1 and N4 top variants have cross-reactivity with monkey CD73-expressing cells. N1 and N4 top variants cannot cross-bind to mouse CD73.

The preceding Examples are offered for illustrative purposes only and are merely possible examples of implementations set forth for a clear understanding of the principles of the disclosure, and are not intended to limit the scope of the present disclosure in any way. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. An anti-CD73 antibody comprising:
a light chain variable domain (VL) sequence comprising a) a CDR-L1 comprising the amino acid sequence of SEQ ID NO:9, b) a CDR-L2 comprising the amino acid sequence of SEQ ID NO: 16, and c) a CDR-L3 comprising the amino acid sequence of SEQ ID NO:24, and a heavy chain variable domain (VH) sequence comprising a) a CDR-H1 comprising the amino acid sequence of SEQ ID NO:27, b) a CDR-H2 comprising the amino acid sequence of SEQ ID NO:37, and c) a CDR-H3 comprising the amino acid sequence of SEQ ID NO:45.

2. The anti-CD73 antibody according to claim 1, wherein the VL of the anti-CD73 antibody comprises the amino acid sequence of SEQ ID NO:91, and wherein the VH of the anti-CD73 antibody comprises the amino acid sequence of SEQ ID NO: 109.

3. An anti-CD73 antibody according to claim 2, wherein the light chain of the anti-CD73 antibody comprises the amino acid sequence of SEQ ID NO:96, and wherein the VH of the anti-CD73 antibody comprises the amino acid sequence of SEQ ID NO: 109.

4. The anti-CD73 antibody according to claim 1, comprising an antigen binding fragment selected from the group consisting of a Fab, a Fab', a F(ab')₂, a single-chain Fv (scFv), an Fv fragment, a diabody, and a linear antibody.

5. The anti-CD73 antibody according to claim 1, wherein the anti-CD73 antibody is a multispecific antibody.

6. The anti-CD73 antibody according to claim 1, which is conjugated to a therapeutic agent or a label.

7. The anti-CD73 antibody according to claim 6, wherein the label is selected from the group consisting of a radioisotope, a fluorescent dye, and an enzyme.

8. One or more isolated nucleic acid molecule that encodes the anti-CD73 antibody, according to claim 1.

9. One or more expression vector comprising the nucleic acid molecule of claim 8.

10. A method of producing the anti-CD73 antibody according to claim 1 comprising culturing a cell comprising one or more isolated nucleic acid molecule that encodes the anti-CD73 antibody according to claim 1 and recovering the anti-CD73 antibody from the cell culture.

11. A composition comprising the anti-CD73 antibody according to claim 1 and a pharmaceutically acceptable carrier.

12. A method for detecting a CD73 protein in a sample from a patient, comprising administering the anti-CD73 antibody according to claim 1 to the patient and obtaining a sample from the patient, or contacting the anti-CD73 antibody according to claim 1 with a sample from the patient, and detecting the anti-CD73 antibody bound to the CD73 protein.

13. The method of claim 12, wherein the contacting or the detecting comprises conducting an immunohistochemistry assay (IHC) or an enzyme-linked immunosorbent assay (ELISA).

14. A method for treating a CD73-expressing cancer in a subject, comprising administering the composition of claim 11 to the subject.

15. The method of claim 14, wherein the cancer is selected from the group consisting of melanoma, NSCLC, head and neck cancer, urothelial cancer, triple-negative breast cancer (TNBC), gastric cancer, classical Hodgkin's lymphoma (cHL), Non-Hodgkin lymphoma, primary mediastinal B-Cell lymphoma (NHL PMBCL), mesothelioma, ovarian cancer, lung cancer, esophageal cancer, nasopharyngeal carcinoma (NPC), biliary tract cancer, colorectal cancer, breast cancer, cervical cancer, thyroid cancer, prostate cancer, bladder cancer, pancreatic cancer, and salivary cancer.

16. The method of claim 14, wherein the subject is further administered a therapeutic agent selected from the group consisting of an anti-neoplastic agent, a chemotherapeutic agent, a growth inhibitory agent, a cytotoxic agent, and an immunotherapeutic agent.

17. The method of claim 14, wherein the subject is further administered radiation therapy and/or a surgical procedure is performed.

*     *     *     *     *

SEQUENCE LISTING

```
<160> NUMBER OF SEQ ID NOS: 119

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gly Ser Ser Ser Asn Ile Gly Ser Asn Thr Val Asn
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Cys Ser Gly Gly Arg Ile Ala Asn Asn Tyr Val Gln
1               5                   10

<210> SEQ ID NO 3
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 3

Thr Gly Thr Ser Ser Asn Ile Gly Ala Gly Tyr Asp Ile His
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Gly Ser Ser Ser Asn Ile Gly Gly Asn Thr Val Asn
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Ser Ser Ser Asn Ile Gly Ser Asn Lys Val Asn
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Gly Thr Ser Ser Asn Ile Gly Gln Gly Tyr Asp Ile His
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gly Thr Ser Ser Asn Ile Gly His Gly Tyr Asp Ile His
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Gly Thr Ser Ser Asn Ile Gly Leu Gly Tyr Asp Ile His
1               5                   10
```

```
<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Gly Thr Ser Ser Asn Ile Gly Ala Gly Phe Asp Ile His
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Gly Thr Ser Ser Asn Ile Gly Thr Gly Tyr Asp Ile His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Asn Asn Gln Arg Pro Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Asp Asn Leu Arg Pro Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Phe Thr Arg Arg Pro Ser
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 14

Arg Phe Val Arg Arg Pro Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Phe Asp Arg Arg Pro Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Phe Ser Arg Arg Pro Ser
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ala Trp Asp Asp Ser Leu Asn Gly Arg Val
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Tyr Asp Ser Asn Asp Gly Val Ala
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Ser Tyr Asp Ser Gly Leu Arg Gly Trp Val
1               5                   10

<210> SEQ ID NO 20
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Ala Ala Trp Asp Ile Ser Leu Asn Gly Arg Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Tyr Asp Ser Gly Leu Arg Gly Trp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Tyr Asp Ser Gly Leu Arg Gly Trp Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Tyr Asp Ser Gly Leu Arg Gly Leu Val
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Tyr Asp Ser Gly Gln Arg Gly Trp Val
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Tyr Ala Met His
1               5
```

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Tyr Tyr Trp Ser
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Tyr Ala Ile Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Tyr Ala Ile Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Tyr Ala Ile Ala
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ile Ser Trp Asn Ser Gly Ser Ile Gly Tyr Ala Asp Ser Val Arg
1               5                   10                  15

Gly

<210> SEQ ID NO 31
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 31

Glu Ile Asn His Ser Gly Ser Thr Asn Tyr Asn Pro Ser Leu Lys Ser
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ile Ile Pro Ile Phe Gly Thr Ala Asn Tyr Ala Gln Lys Phe Gln
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ile Ser Trp Asn Ser Asn Ser Ile Gly Tyr Ala Asp Pro Val Arg
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ile Ile Pro Ile Phe Gly Thr Thr Asn Tyr Ala Gln Lys Phe Gln
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ile Ile Pro Ile Phe Gly Thr Val Asn Tyr Ala Gln Lys Phe Gln
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 36

Arg Ile Ile Pro Ile Phe Gly Thr Thr Asn Tyr Ala Gln Lys Phe Gln
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Met Ile Ile Pro Ile Phe Gly Thr Ala Asn Tyr Ala Gln Lys Phe Gln
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ile Ser Trp Asn Ser Asn Ser Ile Gly Tyr Ala Asp Ser Val Arg
1               5                   10                  15

Gly

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Met Gly Trp Glu Leu Leu Lys Thr Tyr Tyr Tyr Gly Met Asp Val
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Arg Tyr Asp Phe Trp Ser Gly Tyr Tyr Ala Tyr Phe Asp Tyr
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

-continued

Asp Gly Ala Val Ala Ala Tyr Asp Ala Phe Asp Ile
1               5                   10

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Met Gly Trp Glu Leu Leu Lys Thr Ser Tyr Tyr Gly Met Asp Val
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Met Gly Trp Ser Leu Leu Lys Thr Asn Tyr Tyr Gly Met Asp Val
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Gly Ala Val Ala Ala Tyr Asp Ala Phe Ser Ile
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Gly Ala Val Ala Ala Tyr Asp Ala Phe Leu Ile
1               5                   10

<210> SEQ ID NO 46
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
cagactgtgg tgactcagga gccctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc agggagtcct    180
gaccgattct ctggctccaa gtctggcatc tcagcctccc tggccatcag tgggctccag    240

-continued

```
tctgaggatg aggctgatta ttactgtgca gcatgggatg acagcctgaa tggtcgggtg      300
ttcggcggag ggaccaagct gaccgtccta ggtcagccca aggctgcccc ctcggtcact      360
ctgttcccgc cctcctctga ggagcttcaa gccaacaagg ccacactggt gtgtctcata      420
agtgacttct acccgggagc cgtgacagtg gcctggaagg cagatagcag ccccgtcaag      480
gcgggagtgg agaccaccac accctccaaa caaagcaaca caagtacgc ggccagcagc       540 tacctgagcc tgacgcctga gcagtggaag tcccacaaaa gctacagctg ccaggtcacg      600
catgaaggga gcaccgtgga gaagacagtt gcccttacag aatgttcata a               651
```

<210> SEQ ID NO 47
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
cttaattttta tgctgactca gccccactct gtgtcggagt ctccggggaa gacggtgacc       60
atctcctgca catgcagcgg tggcagaatt gccaacaact atgtgcagtg gtaccagcag      120
cgcccgggca cttcccccac cactgtgatc tatgaggata acctaagacc ctctggggtc      180
cctgatcgct tctctggctc gatcgacagg gcctccaatt ctgcctccct caccatctct      240
gacctgagga ctgaggacga ggctcactat tattgccagt cttatgattc caacgatggg      300
gtggctttcg gcggcgggac caaactgacc gtcctgggtc agcccaaggc tgcccctcg       360 gtcactctgt tcccgccctc ctctgaggag cttcaagcca acaaggccac actggtgtgt      420
ctcataagtg acttctaccc gggagccgtg acagtggcct ggaaggcaga tagcagcccc      480
gtcaaggcgg gagtggagac caccacaccc tccaaacaaa gcaacaacaa gtacgcggcc      540
agcagctatc tgagcctgac gcctgagcag tggaagtccc acagaagcta cagctgccag      600
gtcacgcatg agggagcac cgtggagaag acagtggccc ttacagaatg ttcataa          657
```

<210> SEQ ID NO 48
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
caggctgtgc tgactcagcc gtcctcagtg tctggggccc cagggcaaag ggtcaccatc       60
tcctgcaccg ggaccagttc caacatcggg gcaggttatg atatccactg gtatcaacaa      120
cttccaggaa cagcccccaa gctcctcatg taccgtttca ccagacggcc ctcagggggtc     180 cctgaccgat tctctggctc caagtctggc acttctgcct ccctgaccat cactggcctc      240
caggtagagg atgaagctga ttattactgc cagtcctatg acagcggcct gcgtggttgg      300
gtgttcggcg gagggaccaa gctggccgtc ctaggtcagc ccaaggctgc ccctcggtc       360 actctgttcc cacccctcctc tgaggagctt caagccaaca aggccacact ggtgtgtctc     420
ataagtgact tctacccggg agccgtgaca gtggcctgga aggcagatag cagccccgtc      480
aaggcgggag tggagaccac cacaccctcc aaacaaagca acagcaagta cgcggccagc      540
agctacctga gcctgacgcc tgagcagtgg aagtcccaca gaagctacag ctgccaggtc      600
acgcatgaag ggagcaccgt ggagaagaca gttgccctta cagaatgttc ataa            654
```

-continued

<210> SEQ ID NO 49
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
cagactgtgg tgactcagga gccctcagcg tctgggaccc ccgggcagag ggtcaccatc          60
tcttgttctg gaagcagctc caacatcgga ggtaatactg taaattggta ccagcagctc         120
ccaggaacgg cccccaaact cctcatctat agtaataatc agcggccctc aggggtccct         180
gaccgattct ctggctccaa gtctggcatc tcagcctccc tggccatcag tgggctccag         240
tctgaggatg aggctgatta ttactgtgca gcttgggatg acagcctgaa tggtcgggtg         300
ttcggcggag ggaccaagct gaccgtccta                                          330

<210> SEQ ID NO 50
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cagactgtgg tgactcagga gccctcagcg tctgggaccc ccgggcagag ggtcaccatc          60
tcttgttctg gaagcagctc caacatcgga agtaataagg taaattggta ccagcagctc         120
ccaggaacgg cccccaaact cctcatctat agtaataatc agcggccctc aggggtccct         180
gaccgattct ctggctccaa gtctggcatc tcagcctccc tggccatcag tgggctccag         240
tctgaggatg aggctgatta ttactgtgca gcatgggata ttagcctgaa tggtcgggtg         300
ttcggcggag ggaccaagct gaccgtccta                                          330

<210> SEQ ID NO 51
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
caggctgtgc tgactcagcc gtcctcagtg tctggggccc cagggcaaag ggtcaccatc          60
tcctgcaccg ggaccagttc caacatcggg gcaggttatg atatccactg gtatcaacaa         120
cttccaggaa cagcccccaa gctcctcatg taccgtttca ccagacggcc ctcaggggtc         180
cctgaccgat tctctggctc caagtctggc acttctgcct ccctgaccat cactggcctc         240
caggtagagg atgaagctga ttattactgc cagtcctatg acagcggcct gcgtggttgg         300
tacttcggcg gagggaccaa gctgaccgtc cta                                       333

<210> SEQ ID NO 52
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide -continued

```
<400> SEQUENCE: 52
caggctgtgc tgactcagcc gtcctcagtg tctggggccc cagggcaaag ggtcaccatc     60
tcctgcaccg ggaccagttc caacatcggg gcaggttatg atatccactg gtatcaacaa    120
cttccaggaa cagcccccaa gctcctcatg taccgtttca ccagacggcc ctcaggggtc    180
cctgaccgat tctctggctc caagtctggc acttctgcct ccctgaccat cactggcctc    240
caggtagagg atgaagctga ttattactgc cagtcctatg acagcggcct acgtggttgg    300
gcgttcggcg gagggaccaa gctgaccgtc cta                                 333

<210> SEQ ID NO 53
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caggctgtgc tgactcagcc gtcctcagtg tctggggccc cagggcaaag ggtcaccatc     60
tcctgcaccg ggaccagttc caacatcggg gcaggttatg atatccactg gtatcaacaa    120
cttccaggaa cagcccccaa gctcctcatg taccgtttca ccagacggcc ctcaggggtc    180
cctgaccgat tctctggttc caagtctggc acttctgcct ccctgaccat cactggcctc    240
caggtagagg atgaagctga ttattactgc cagtcctatg acagcggcct gcgtggtctt    300
gtgttcggcg gagggaccaa gctgaccgtc cta                                 333

<210> SEQ ID NO 54
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caggctgtgc tgactcagcc gtcctcagtg tctggggccc cagggcaaag ggtcaccatc     60
tcctgcaccg ggaccagttc caacatcggg gcaggttatg atatccactg gtatcaacaa    120
cttccaggaa cagcccccaa gctcctcatg taccgtttca ccagacggcc ctcaggggtc    180
cctgaccgat tctctggctc caagtctggc acttctgcct ccctgaccat cactggcctc    240
caggtagagg atgaagctga ttattactgc cagtcctatg acagcggcca gcgtggttgg    300
gtgttcggcg ggggggaccaa gctgaccgtc cta                                333

<210> SEQ ID NO 55
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
caggctgtgc tgactcagcc gtcctcagtg tctggggccc cagggcaaag ggtcaccatc     60
tcctgcaccg ggaccagttc caacatcggg caggttatg atatccactg gtatcaacaa     120
cttccaggaa cagcccccaa gctcctcatg taccgtttca cccggcggcc ctcaggggtc    180
cctgaccgat tctctggctc caagtctggc acttctgcct ccctgaccat cactggcctc    240
```
caggtagagg atgaagctga ttattactgc cagtcctatg acagcggcct acgtggttgg        300
gcgttcggcg gagggaccaa gctgaccgtc cta                                     333

<210> SEQ ID NO 56
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
caggctgtgc tgactcagcc gtcctcagtg tctggggccc cagggcaaag ggtcaccatc        60
tcctgcaccg ggaccagttc caacatcggg catggttatg atatccactg gtatcaacat       120
cttccaggaa cagcccccaa gctcctcatg taccgtttcg ttagacggcc ctcaggggtc       180
cctgaccgat tctctggctc caagtctggc acttctgcct ccctgaccat cactggcctc       240
caggtagagg atgaagctga ttattactgc cagtcctatg acagcggcca gcgtggttgg       300
gtgttcggcg gagggaccaa gctgaccgtc cta                                     333

<210> SEQ ID NO 57
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
caggctgtgc tgactcagcc gtcctcagtg tctggggccc cagggcaaag ggtcaccatc        60
tcctgcaccg ggaccagttc caacatcggg ctgggttatg atatccactg gtatcaacat       120
cttccaggaa cagcccccaa gctcctcatg taccgtttcg atagacggcc ctcaggggtc       180
cctgaccgat tctctggctc caagtctggc acttctgcct ccctgaccat cactggcctc       240
caggtagagg atgaagctga ttattactgc cagtcctatg acagcggcca gcgtggttgg       300
gtgttcggcg gagggaccaa gctgaccgtc cta                                     333

<210> SEQ ID NO 58
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
caggctgtgc tgactcagcc gtcctcagtg tctggggccc cagggcaaag ggtcaccatc        60
tcctgcaccg ggaccagttc caacatcggg gcaggttttg atattcactg gtatcaacaa       120
cttccaggaa cagcccccaa gctcctcatg taccgtttca gtagacggcc ctcaggggtc       180
cctgaccgat tctctggctc caagtctggc acttctgcct ccctgaccat cactggcctc       240
caggtagagg atgaagctga ttattactgc cagtcctatg acagcggcca gcgtggttgg       300
gtgttcggcg gagggaccaa gctgaccgtc cta                                     333

<210> SEQ ID NO 59
<211> LENGTH: 333
<212> TYPE: DNA
<213> ORGANISM: Artificial Sequence
<220> FEATURE:

-continued

<223> OTHER INFORMATION: Description of Artificial Sequence: Synthetic
      polynucleotide

<400> SEQUENCE: 59

```
caggctgtgc tgactcagcc gtcctcagtg tctggggccc cagggcaaag ggtcaccatc      60
tcctgcaccg ggaccagttc caacatcggg actggttatg atatccactg gtatcaacaa     120
cttccaggaa cagcccccaa gctcctcatg taccggttca ccagacggcc ctcaggggtc     180
cctgaccgat tctctggctc caagtctggc acttctgcct ccctgaccat cactggcctc     240
caggtagagg atgaagctga ttattactgc cagtcctatg acagcggcca gcgtggttgg     300
gtgttcggcg gagggaccaa gctgaccgtc cta                                  333
```

<210> SEQ ID NO 60
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
cagactgtgg tgactcagga gccctcagcg tctgggaccc ccgggcagag ggtcaccatc      60
tcttgttctg gaagcagctc caacatcgga ggtaatactg taaattggta ccagcagctc     120
ccaggaacgg cccccaaact cctcatctat agtaataatc agcggccctc aggggtccct     180
gaccgattct ctggctccaa gtctggcatc tcagcctccc tggccatcag tgggctccag     240
tctgaggatg aggctgatta ttactgtgca gcttgggatg acagcctgaa tggtcgggtg     300
ttcggcggag ggaccaagct gaccgtccta ggtcagccca aggctgcccc ctcggtcact     360
ctgttcccgc cctcctctga ggagcttcaa gccaacaagg ccacactggt gtgcctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
tacctgagcc tgacgcctga gcagtggaag tcccacaaaa gctacagctg ccaggtcacg     600
catgaaggga gcaccgtgga gaagacagtt gcccctacag aatgttcata a               651
```

<210> SEQ ID NO 61
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
cagactgtgg tgactcagga gccctcagcg tctgggaccc ccgggcagag ggtcaccatc      60
tcttgttctg gaagcagctc caacatcgga agtaataagg taaattggta ccagcagctc     120
ccaggaacgg cccccaaact cctcatctat agtaataatc agcggccctc aggggtccct     180
gaccgattct ctggctccaa gtctggcatc tcagcctccc tggccatcag tgggctccag     240
tctgaggatg aggctgatta ttactgtgca gcatgggata ttagcctgaa tggtcgggtg     300
ttcggcggag ggaccaagct gaccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca acaagtacgc ggccagcagc     540
```

-continued

```
tacctgagcc tgacgcctga gcagtggaag tcccacaaaa gctacagctg ccaggtcacg      600
catgaaggga gcaccgtgga gaagacagtt gcccctacag aatgttcata a              651

<210> SEQ ID NO 62
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
caggctgtgc tgactcagcc gtcctcagtg tctggggccc cagggcaaag ggtcaccatc       60
tcctgcaccg ggaccagttc caacatcggg ctgggttatg atatccactg gtatcaacaa      120
cttccaggaa cagcccccaa gctcctcatg taccgtttcg atagacggcc ctcaggggtc      180
cctgaccgat tctctggctc caagtctggc acttctgcct ccctgaccat cactggcctc      240
caggtagagg atgaagctga ttattactgc cagtcctatg acagcggcca gcgtggttgg      300
gtgttcggcg gagggaccaa gctgaccgtc ctaggtcagc ccaaggctgc cccctcggtc      360
actctgttcc cgccctcctc tgaggagctt caagccaaca aggccacact ggtgtgtctc      420
ataagtgact tctacccggg agccgtgaca gtggcctgga aggcagatag cagccccgtc      480
aaggcgggag tggagaccac cacaccctcc aaacaaagca acaacaagta cgcggccagc      540
agctacctga gcctgacgcc tgagcagtgg aagtcccaca aaagctacag ctgccaggtc      600
acgcatgaag ggagcaccgt ggagaagaca gttgcccta cagaatgttc ataa           654

<210> SEQ ID NO 63
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
caggctgtgc tgactcagcc gtcctcagtg tctggggccc cagggcaaag ggtcaccatc       60
tcctgcaccg ggaccagttc caacatcggg gcaggttttg atattcactg gtatcaacaa      120
cttccaggaa cagcccccaa gctcctcatg taccgtttca gtagacggcc ctcaggggtc      180
cctgaccgat tctctggctc caagtctggc acttctgcct ccctgaccat cactggcctc      240
caggtagagg atgaagctga ttattactgc cagtcctatg acagcggcca gcgtggttgg      300
gtgttcggcg gagggaccaa gctgaccgtc ctaggtcagc ccaaggctgc cccctcggtc      360
actctgttcc cgccctcctc tgaggagctt caagccaaca aggccacact ggtgtgtctc      420
ataagtgact tctacccggg agccgtgaca gtggcctgga aggcagatag cagccccgtc      480
aaggcgggag tggagaccac cacaccctcc aaacaaagca acaacaagta cgcggccagc      540
agctacctga gcctgacgcc tgagcagtgg aagtcccaca aaagctacag ctgccaggtc      600
acgcatgaag ggagcaccgt ggagaagaca gttgcccta cagaatgttc ataa           654

<210> SEQ ID NO 64
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 64
gaggtgcagc tggtggagtc cgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaggggccg attcaccatc tccagagaca acgccaagaa ctccctgtat     240
ctgcaaatga acagtctgag agctgaggac acggccttgt attactgtgc aaaagatatg     300
gggtgggagc tactaaaaac ctactactac ggtatggacg tctggggcca agggaccacg     360
gtcaccgtct caagc                                                       375

<210> SEQ ID NO 65
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caggtgcagc tacagcagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca gagtcgagt caccatatca gtagacacgt ccaagaacca gttctccctg      240
aagctgagct ctgtgaccgc cgcggacacg gctgtgtatt actgtgcgag aggccggtac     300
gatttttgga gtggttatta tgcgtacttt gactactggg gccagggcac cctggtcacc     360
gtctcaagc                                                              369

<210> SEQ ID NO 66
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
caggtccagc tggtacaatc tggggctgag gtgaagaagt ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag catagcctac     240
atggagctga gcagcctgag atctgaggac acggccgtgt attactgtgc gagtgatgga     300
gcagtggctg cttatgatgc ttttgatatc tggggccaag gacaatggt caccgtctca      360 agc                                                                    363

<210> SEQ ID NO 67
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
gaggtgcagc tggtggagtc cgggggaggc ttggtacagc ctggcaggtc cctgagactc      60
```

```
tcctgtgcag cctctggact caccttttgat gattatgcca tgcactgggt ccggcaagct    120
ccagggaagg gcctggagtg ggtctcaggt attagttgga atagtaatag cataggctat    180
gcggaccctg tgaggggccg attcaccatc tccagagaca acgccaagaa ctccctgtat    240
ctgcaaatga acagtctgag agctgaggac acggccttgt attactgtgc aaaagatatg    300
gggtgggagc tactaaaaac ctcttactac ggtatggacg tctggggcca agggaccacg    360
gtcaccgtct caagc                                                      375
```

<210> SEQ ID NO 68
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gaggtgcagc tggtggagtc cgggggaggc ttggtacagc ctggcaggtc cctgagactc     60
tcctgtgcag cctctggatt caccttttgat gattatgcca tgcactgggt ccggctagct    120
ccagggaagg gcctggagtg ggtctcaggt attagttgga atagtggtag cataggctat    180
gcggactctg tgaggggccg attcaccatc tccagagaca acgccaagaa ctccctgtat    240
ctgcaaatga acagtctgag agctgaggac acggccttgt attactgtgc aaaagatatg    300
gggtggagtc tactaaaaac caactactac ggtatggacg tctggggcca agggaccacg    360
gtcaccgtct caagc                                                      375
```

<210> SEQ ID NO 69
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
caggtccagc tggtacaatc tggggctgag gtgaagaagt ctgggtcctc ggtgaaggtc     60
tcctgcaagg cctctggata taccttcagc agctatgcta tcacttgggt gcgacaggcc    120
cctggacaag gcttgagtg gatgggaggg atcatcccta tctttggtac agcaaaactac   180 gcacagaagt tccagggcag agtcacgatt accgcggacg aatccacgag catagcctac    240
atggagctga gcagcctgag atctgaggac acggccgtgt attactgtgc gagtgatgga    300
gcagtggctg cttatgatgc ttttgatatt tggggccaag gacaatggt caccgtctca    360 agc                                                                   363
```

<210> SEQ ID NO 70
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
caggtccagc tggtacaatc tggggctgag gtgaagaagt ctgggtcctc ggtgaaggtc     60
tcctgcaagg cttctggagg caccttcgct agctatgcta ttagttgggt gcgacaggcc    120
cctggacaag gcttgagtg gatgggaggg atcatcccta tctttggtac aacaaactac    180
```

```
gcacagaagt tccagggcag agtcacgatt accgcggacg aatccacgag catagcctac      240
atggagctga gcagcctgag atctgaggac acggccgtgt attactgtgc gagtgatgga      300
gcagtggctg cttatgatgc ttttgatatt tgggggccaag ggacaatggt caccgtctca      360
agc                                                                   363
```

<210> SEQ ID NO 71
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
caggtccagc tggtacaatc tgggggctgag gtgaagaagt ctgggtcctc ggtgaaggtc       60
tcctgcaagg cttctggagg caccttcagc agctatgcta tcgcttgggt gcgacaggcc      120
cctggacaag ggcttgagtg gatgggaggg atcatcccta tctttggtac agtaaactac      180
gcacagaagt tccagggcag agtcacgatt accgcggacg aatccacgag catagcctac      240
atggagctga gcagcctgag atctgaggac acggccgtgt attactgtgc gagtgatgga      300
gcagtggctg cttatgatgc ttttagtata tgggggccaag ggacaatggt caccgtctca      360
agc                                                                   363
```

<210> SEQ ID NO 72
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
caggtccagc tggtacaatc tgggggctgag gtgaagaagt ctgggtcctc ggtgaaggtc       60
tcctgcaagg cttctggagg cacgttcagc agctatgcta tcagttgggt gcgacaggcc      120
cctggacaag ggcttgagtg gatgggaggg atcatcccta tctttggtac aacaaactac      180
gcacagaagt tccagggcag agtcacgatt accgcggacg aatccacgag catagcctac      240
atggagctga gtagcctgag atctgaggac acggccgtgt attactgtgc gagtgatgga      300
gcagtggctg cttatgatgc ttttctgatc tgggggccaag ggacaatggt caccgtctca      360
agc                                                                   363
```

<210> SEQ ID NO 73
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
caggtccagc tggtacaatc tgggggctgag gtgaagaagt ctgggtcctc ggtgaaggtc       60
tcctgcaagg cttctggagg caccttcgct agctatgcta ttagttgggt gcgacaggcc      120
cctggacaag ggcttgagtg gatgggaggg atcatcccta tctttggtac agttaactac      180
gcacagaagt tccagggcag agtcacgatt accgcggacg aatccacgag catagcctac      240
atggagctga gcagcctgag atctgaggac acggccgtgt attactgtgc gagtgatgga      300
```

-continued

```
gcagtggctg cttatgatgc ttttgatatt tggggccaag ggacaatggt caccgtctca      360
agc                                                                    363

<210> SEQ ID NO 74
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtccagc tggtacaatc tggggctgag gtgaagaagt ctgggtcctc ggtgaaggtc       60
tcctgcaagg cttctggagg cacgttcagc agctatgcta tcagttgggt gcgacaggcc      120
cctggacaag ggcttgagtg gatgggaagg atcatcccta tctttggtac aacaaactac      180
gcacagaagt tccagggcag agtcacgatt accgcggacg aatccacgag catagcctac      240
atggagctga gtagcctgag atctgaggac acggccgtgt attactgtgc gagtgatgga      300
gcagtggctg cttatgatgc ttttctgatc tggggccaag ggacaatggt caccgtctca      360
agc                                                                    363

<210> SEQ ID NO 75
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
caggtccagc tggtacaatc tggggctgag gtgaagaagt ctgggtcctc ggtgaaggtc       60
tcctgcaagg cttctggagg cacgttcagc agctatgcta tcagttgggt gcgacaggcc      120
cctggacaag ggcttgagtg gatgggaggg atcatcccta tctttggtac agcaaactac      180
gcacagaagt tccagggcag agtcacgatt accgcggacg aatccacgag catagcctac      240
atggagctga gtagcctgag atctgaggac acggccgtgt attactgtgc gagtgatgga      300
gcagtggctg cttatgatgc ttttctgatc tggggccaag ggacaatggt caccgtctca      360
agc                                                                    363

<210> SEQ ID NO 76
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
caggtccagc tggtacaatc tggggctgag gtgaagaagt ctgggtcctc ggtgaaggtc       60
tcctgcaagg cttctggagg cacgttcagc agctatgcta tcagttgggt gcgacaggcc      120
cctggacaag ggcttgagtg gatgggaatg atcatcccta tctttggtac agcaaactac      180
gcacagaagt tccagggcag agtcacgatt accgcggacg aatccacgag catagcctac      240
atggagctga gtagcctgag atctgaggac acggccgtgt attactgtgc gagtgatggg      300
gcagtggctg cttatgatgc ttttctgatc tggggccaag ggacaatggt caccgtctca      360
agc                                                                    363
```

-continued

<210> SEQ ID NO 77
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
caggtccagc tggtacaatc tgggggctgag gtgaagaagt ctgggtcctc ggtgaaggtc      60
tcctgcaagg cttctggagg cacgttcagc agctatgcta tcagttgggt gcgacaggcc     120
cctggacaag ggcttgagtg gatgggaagg atcatccta tctttggtac aacaaactac      180
gcacagaagt tccagggcag agtcacgatt accgcggacg aatccacgag catagcctac     240
atggagctga gtagcctgag atctgaggac acggccatgt attactgtgc gagtgatgga     300
gcagtggctg cttatgatgc ttttctgatc tggggccaag ggacaatggt caccgtctcg     360
agc                                                                  363

<210> SEQ ID NO 78
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gaggtgcagc tggtggagtc cggggggaggc ttggtacagc ctggcaggtc cctgagactc      60
tcctgtgcag cctctggatt caccttttgat gattatgcca tgcactgggt ccggcaagct     120
ccagggaagg gcctggagtg ggtctcaggt attagttgga atagtaatag cataggctat      180
gcggactctg tgaggggccg attcaccatc tccagagaca acgccaagaa ctccctgtat      240
ctgcaaatga acagtctgag agctgaggac acggccttgt attactgtgc aaaagatatg      300
gggtgggagc tactaaaaac ctcttactac ggtatggacg tctggggcca agggaccacg     360
gtcaccgtct caagc                                                      375

<210> SEQ ID NO 79
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Thr Val Val Thr Gln Glu Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

```
Asn Gly Arg Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
            195                 200                 205

Thr Val Ala Leu Thr Glu Cys Ser
            210                 215

<210> SEQ ID NO 80
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Asn Phe Met Leu Thr Gln Pro His Ser Val Ser Glu Ser Pro Gly
1               5                   10                  15

Lys Thr Val Thr Ile Ser Cys Thr Cys Ser Gly Gly Arg Ile Ala Asn
                20                  25                  30

Asn Tyr Val Gln Trp Tyr Gln Gln Arg Pro Gly Thr Ser Pro Thr Thr
            35                  40                  45

Val Ile Tyr Glu Asp Asn Leu Arg Pro Ser Gly Val Pro Asp Arg Phe
            50                  55                  60

Ser Gly Ser Ile Asp Arg Ala Ser Asn Ser Ala Ser Leu Thr Ile Ser
65                  70                  75                  80

Asp Leu Arg Thr Glu Asp Glu Ala His Tyr Tyr Cys Gln Ser Tyr Asp
                85                  90                  95

Ser Asn Asp Gly Val Ala Phe Gly Gly Gly Thr Lys Leu Thr Val Leu
            100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
            130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Gly Gly Ser Thr Val
            195                 200                 205

Glu Lys Thr Val Ala Leu Thr Glu Cys Ser
            210                 215

<210> SEQ ID NO 81
```

-continued

<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
            20                  25                  30

Tyr Asp Ile His Trp Tyr Gln Gln Leu Pro Gly Thr Ala Pro Lys Leu
        35                  40                  45

Leu Met Tyr Arg Phe Thr Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Leu Arg Gly Trp Val Phe Gly Gly Gly Thr Lys Leu Ala Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Ser Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Leu Thr Glu Cys Ser
    210                 215

<210> SEQ ID NO 82
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Thr Val Val Thr Gln Glu Pro Ser Ala Ser Gly Thr Pro Gly Gln
1               5                   10                  15

Arg Val Thr Ile Ser Cys Ser Gly Ser Ser Ser Asn Ile Gly Gly Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

```
Asn Gly Arg Val Phe Gly Gly Gly Thr Lys Leu Thr Val Leu
            100                 105                 110

<210> SEQ ID NO 83
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Thr Val Val Thr Gln Glu Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Lys Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Asp Tyr Tyr Cys Ala Ala Trp Asp Ile Ser Leu
                85                  90                  95

Asn Gly Arg Val Phe Gly Gly Gly Thr Lys Leu Thr Val Leu
            100                 105                 110

<210> SEQ ID NO 84
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
            20                  25                  30

Tyr Asp Ile His Trp Tyr Gln Gln Leu Pro Gly Thr Ala Pro Lys Leu
        35                  40                  45

Leu Met Tyr Arg Phe Thr Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Leu Arg Gly Trp Tyr Phe Gly Gly Gly Thr Lys Leu Thr Val Leu
            100                 105                 110

<210> SEQ ID NO 85
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85
```

-continued

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
                20                  25                  30

Tyr Asp Ile His Trp Tyr Gln Gln Leu Pro Gly Thr Ala Pro Lys Leu
            35                  40                  45

Leu Met Tyr Arg Phe Thr Arg Arg Pro Ser Gly Val Pro Asp Arg Phe
        50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Leu Arg Gly Trp Ala Phe Gly Gly Gly Thr Lys Leu Thr Val Leu
            100                 105                 110
```

```
<210> SEQ ID NO 86
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86
```

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
                20                  25                  30

Tyr Asp Ile His Trp Tyr Gln Gln Leu Pro Gly Thr Ala Pro Lys Leu
            35                  40                  45

Leu Met Tyr Arg Phe Thr Arg Arg Pro Ser Gly Val Pro Asp Arg Phe
        50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Leu Arg Gly Leu Val Phe Gly Gly Gly Thr Lys Leu Thr Val Leu
            100                 105                 110
```

```
<210> SEQ ID NO 87
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87
```

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
                20                  25                  30

Tyr Asp Ile His Trp Tyr Gln Gln Leu Pro Gly Thr Ala Pro Lys Leu
            35                  40                  45

Leu Met Tyr Arg Phe Thr Arg Arg Pro Ser Gly Val Pro Asp Arg Phe
        50                  55                  60

Ser Gly Ser Lys Ser Gly Thr Ser Ala Ser Leu Thr Ile Thr Gly Leu
65                  70                  75                  80
```

```
Gln Val Glu Asp Glu Ala Asp Tyr Tyr Cys Gln Ser Tyr Asp Ser Gly
                85                   90                   95

Gln Arg Gly Trp Val Phe Gly Gly Gly Thr Lys Leu Thr Val Leu
        100                 105                 110

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Gln Gly
            20                  25                  30

Tyr Asp Ile His Trp Tyr Gln Gln Leu Pro Gly Thr Ala Pro Lys Leu
        35                  40                  45

Leu Met Tyr Arg Phe Thr Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Leu Arg Gly Trp Ala Phe Gly Gly Gly Thr Lys Leu Thr Val Leu
        100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly His Gly
            20                  25                  30

Tyr Asp Ile His Trp Tyr Gln His Leu Pro Gly Thr Ala Pro Lys Leu
        35                  40                  45

Leu Met Tyr Arg Phe Val Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Gln Arg Gly Trp Val Phe Gly Gly Gly Thr Lys Leu Thr Val Leu
        100                 105                 110

<210> SEQ ID NO 90
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 90

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Leu Gly
            20                  25                  30

Tyr Asp Ile His Trp Tyr Gln His Leu Pro Gly Thr Ala Pro Lys Leu
        35                  40                  45

Leu Met Tyr Arg Phe Asp Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Gln Arg Gly Trp Val Phe Gly Gly Gly Thr Lys Leu Thr Val Leu
            100                 105                 110
```

<210> SEQ ID NO 91
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
            20                  25                  30

Phe Asp Ile His Trp Tyr Gln Gln Leu Pro Gly Thr Ala Pro Lys Leu
        35                  40                  45

Leu Met Tyr Arg Phe Ser Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Gln Arg Gly Trp Val Phe Gly Gly Gly Thr Lys Leu Thr Val Leu
            100                 105                 110
```

<210> SEQ ID NO 92
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Thr Gly
            20                  25                  30

Tyr Asp Ile His Trp Tyr Gln Gln Leu Pro Gly Thr Ala Pro Lys Leu
        35                  40                  45

Leu Met Tyr Arg Phe Thr Arg Arg Pro Ser Gly Val Pro Asp Arg Phe
    50                  55                  60

Ser Gly Ser Lys Ser Gly Thr Ser Ala Ser Leu Thr Ile Thr Gly Leu
```

-continued

```
65              70              75              80

Gln Val Glu Asp Glu Ala Asp Tyr Tyr Cys Gln Ser Tyr Asp Ser Gly
                85              90              95

Gln Arg Gly Trp Val Phe Gly Gly Gly Thr Lys Leu Thr Val Leu
            100             105             110

<210> SEQ ID NO 93
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Thr Val Val Thr Gln Glu Pro Ser Ala Ser Gly Thr Pro Gly Gln
1               5               10              15

Arg Val Thr Ile Ser Cys Ser Gly Ser Ser Ser Asn Ile Gly Gly Asn
                20              25              30

Thr Val Asn Trp Tyr Gln Gln Leu Pro Gly Thr Ala Pro Lys Leu Leu
            35              40              45

Ile Tyr Ser Asn Asn Gln Arg Pro Ser Gly Val Pro Asp Arg Phe Ser
        50              55              60

Gly Ser Lys Ser Gly Ile Ser Ala Ser Leu Ala Ile Ser Gly Leu Gln
65              70              75              80

Ser Glu Asp Glu Ala Asp Tyr Tyr Cys Ala Ala Trp Asp Asp Ser Leu
                85              90              95

Asn Gly Arg Val Phe Gly Gly Gly Thr Lys Leu Thr Val Leu Gly Gln
            100             105             110

Pro Lys Ala Ala Pro Ser Val Thr Leu Phe Pro Pro Ser Ser Glu Glu
        115             120             125

Leu Gln Ala Asn Lys Ala Thr Leu Val Cys Leu Ile Ser Asp Phe Tyr
    130             135             140

Pro Gly Ala Val Thr Val Ala Trp Lys Ala Asp Ser Ser Pro Val Lys
145             150             155             160

Ala Gly Val Glu Thr Thr Thr Pro Ser Lys Gln Ser Asn Asn Lys Tyr
                165             170             175

Ala Ala Ser Ser Tyr Leu Ser Leu Thr Pro Glu Gln Trp Lys Ser His
            180             185             190

Lys Ser Tyr Ser Cys Gln Val Thr His Glu Gly Ser Thr Val Glu Lys
        195             200             205

Thr Val Ala Pro Thr Glu Cys Ser
    210             215

<210> SEQ ID NO 94
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Thr Val Val Thr Gln Glu Pro Ser Ala Ser Gly Thr Pro Gly Gln
1               5               10              15

Arg Val Thr Ile Ser Cys Ser Gly Ser Ser Ser Asn Ile Gly Ser Asn
                20              25              30

Lys Val Asn Trp Tyr Gln Gln Leu Pro Gly Thr Ala Pro Lys Leu Leu
```

-continued

```
                35                  40                  45
Ile Tyr Ser Asn Asn Gln Arg Pro Ser Gly Val Pro Asp Arg Phe Ser
    50                  55                  60

Gly Ser Lys Ser Gly Ile Ser Ala Ser Leu Ala Ile Ser Gly Leu Gln
65                  70                  75                  80

Ser Glu Asp Glu Ala Asp Tyr Tyr Cys Ala Ala Trp Asp Ile Ser Leu
                85                  90                  95

Asn Gly Arg Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Lys Ser Tyr Ser Cys Gln Val Thr His Glu Gly Ser Thr Val Glu Lys
                195                 200                 205

Thr Val Ala Pro Thr Glu Cys Ser
    210                 215

<210> SEQ ID NO 95
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Leu Gly
                20                  25                  30

Tyr Asp Ile His Trp Tyr Gln Gln Leu Pro Gly Thr Ala Pro Lys Leu
        35                  40                  45

Leu Met Tyr Arg Phe Asp Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Gln Arg Gly Trp Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175
```

```
Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
        195                 200                 205

Lys Thr Val Ala Pro Thr Glu Cys Ser
    210                 215
```

```
<210> SEQ ID NO 96
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96
```

```
Gln Ala Val Leu Thr Gln Pro Ser Ser Val Ser Gly Ala Pro Gly Gln
1               5                   10                  15

Arg Val Thr Ile Ser Cys Thr Gly Thr Ser Ser Asn Ile Gly Ala Gly
            20                  25                  30

Phe Asp Ile His Trp Tyr Gln Gln Leu Pro Gly Thr Ala Pro Lys Leu
        35                  40                  45

Leu Met Tyr Arg Phe Ser Arg Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Gln Val Glu Asp Glu Ala Asp Tyr Tyr Cys Gln Ser Tyr Asp Ser Gly
                85                  90                  95

Gln Arg Gly Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Lys Ser Tyr Ser Cys Gln Val Thr His Glu Gly Ser Thr Val Glu
        195                 200                 205

Lys Thr Val Ala Pro Thr Glu Cys Ser
    210                 215
```

```
<210> SEQ ID NO 97
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97
```

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30
```

-continued

```
Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Gly Trp Glu Leu Leu Lys Thr Tyr Tyr Tyr Gly Met
            100                 105                 110

Asp Val Trp Gly Gln Gly Thr Thr Val Thr Val Ser Ser
        115                 120                 125
```

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Tyr Asp Phe Trp Ser Gly Tyr Tyr Ala Tyr Phe Asp Tyr
            100                 105                 110

Trp Gly Gln Gly Thr Leu Val Thr Val Ser Ser
        115                 120
```

<210> SEQ ID NO 99
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Ile Ala Tyr
65                  70                  75                  80
```

-continued

```
Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Asp Ile Trp Gly
            100                 105                 110

Gln Gly Thr Met Val Thr Val Ser Ser
        115                 120

<210> SEQ ID NO 100
<211> LENGTH: 125
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 100

Glu Val Gln Leu Val Glu Ser Gly Gly Gly Leu Val Gln Pro Gly Arg
1               5                   10                  15

Ser Leu Arg Leu Ser Cys Ala Ala Ser Gly Leu Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asn Ser Ile Gly Tyr Ala Asp Pro Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Gly Trp Glu Leu Leu Lys Thr Ser Tyr Tyr Gly Met
            100                 105                 110

Asp Val Trp Gly Gln Gly Thr Thr Val Thr Val Ser Ser
        115                 120                 125

<210> SEQ ID NO 101
<211> LENGTH: 125
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 101

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Leu Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Gly Trp Ser Leu Leu Lys Thr Asn Tyr Tyr Gly Met
            100                 105                 110

Asp Val Trp Gly Gln Gly Thr Thr Val Thr Val Ser Ser
        115                 120                 125
```

-continued

<210> SEQ ID NO 102
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Lys Lys Ser Gly Ser
1               5                   10                  15

Ser Val Lys Val Ser Cys Lys Ala Ser Gly Tyr Thr Phe Ser Ser Tyr
                20                  25                  30

Ala Ile Thr Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Asp Ile Trp Gly
            100                 105                 110

Gln Gly Thr Met Val Thr Val Ser Ser
        115                 120

<210> SEQ ID NO 103
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ala Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Lys Phe
        50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Asp Ile Trp Gly
            100                 105                 110

Gln Gly Thr Met Val Thr Val Ser Ser
        115                 120

<210> SEQ ID NO 104
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ala Trp Val Arg Gln Ala Pro Gly Gln Gly Leu Glu Trp Met
        35                  40                  45

Gly Gly Ile Ile Pro Ile Phe Gly Thr Val Asn Tyr Ala Gln Lys Phe
    50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Ser Ile Trp Gly
            100                 105                 110

Gln Gly Thr Met Val Thr Val Ser Ser
        115                 120
```

<210> SEQ ID NO 105
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Leu Ile Trp Gly
            100                 105                 110

Gln Gly Thr Met Val Thr Val Ser Ser
        115                 120
```

<210> SEQ ID NO 106
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ala Ser Tyr
            20                  25                  30

Ala Ile Ser Trp Val Arg Gln Ala Pro Gly Gln Gly Leu Glu Trp Met
```

-continued

```
          35                40                45
```

Gly Gly Ile Ile Pro Ile Phe Gly Thr Val Asn Tyr Ala Gln Lys Phe
    50                55                60

Gln Gly Arg Val Thr Ile Thr Ala Asp Glu Ser Thr Ser Ile Ala Tyr
65                70                75                80

Met Glu Leu Ser Ser Leu Arg Ser Glu Asp Thr Ala Val Tyr Tyr Cys
                85                90                95

Ala Ser Asp Gly Ala Val Ala Ala Tyr Asp Ala Phe Asp Ile Trp Gly
               100                105                110

Gln Gly Thr Met Val Thr Val Ser Ser
          115                120

<210> SEQ ID NO 107
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Glu Val Lys Lys Ser Gly Ser
1                 5                 10                15

Ser Val Lys Val Ser Cys Lys Ala Ser Gly Gly Thr Phe Ser Ser Tyr
               20                25                30

Ala Ile Ser Trp Val Arg Gln Ala Pro Gly Gln Gly Leu Glu Trp Met
          35                40                45

Gly Arg Ile Ile Pro Ile Phe Gly Thr Thr Asn Tyr Ala Gln Lys Phe
    50                55                60

Gln Gly Arg Val Thr Ile Thr Ala Asp Glu Ser Thr Ser Ile Ala Tyr
65                70                75                80

Met Glu Leu Ser Ser Leu Arg Ser Glu Asp Thr Ala Val Tyr Tyr Cys
                85                90                95

Ala Ser Asp Gly Ala Val Ala Ala Tyr Asp Ala Phe Leu Ile Trp Gly
               100                105                110

Gln Gly Thr Met Val Thr Val Ser Ser
          115                120

<210> SEQ ID NO 108
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Ala Glu Val Lys Lys Ser Gly Ser
1                 5                 10                15

Ser Val Lys Val Ser Cys Lys Ala Ser Gly Gly Thr Phe Ser Ser Tyr
               20                25                30

Ala Ile Ser Trp Val Arg Gln Ala Pro Gly Gln Gly Leu Glu Trp Met
          35                40                45

Gly Gly Ile Ile Pro Ile Phe Gly Thr Ala Asn Tyr Ala Gln Lys Phe
    50                55                60

Gln Gly Arg Val Thr Ile Thr Ala Asp Glu Ser Thr Ser Ile Ala Tyr
65                70                75                80

Met Glu Leu Ser Ser Leu Arg Ser Glu Asp Thr Ala Val Tyr Tyr Cys
```

```
                        85                  90                  95

Ala Ser Asp Gly Ala Val Ala Ala Tyr Asp Ala Phe Leu Ile Trp Gly
            100                 105                 110

Gln Gly Thr Met Val Thr Val Ser Ser
        115                 120

<210> SEQ ID NO 109
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Met Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Leu Ile Trp Gly
            100                 105                 110

Gln Gly Thr Met Val Thr Val Ser Ser
        115                 120

<210> SEQ ID NO 110
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Phe Gly Thr Thr Asn Tyr Ala Gln Lys Phe
    50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Met Tyr Tyr Cys
                85                  90                  95

Ala Ser Asp Gly Ala Val Ala Ala Tyr Asp Ala Phe Leu Ile Trp Gly
            100                 105                 110

Gln Gly Thr Met Val Thr Val Ser Ser
        115                 120
```

-continued

```
<210> SEQ ID NO 111
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asn Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Gly Trp Glu Leu Leu Lys Thr Ser Tyr Tyr Gly Met
            100                 105                 110

Asp Val Trp Gly Gln Gly Thr Thr Val Thr Val Ser Ser
            115                 120                 125

<210> SEQ ID NO 112
<211> LENGTH: 326
<212> TYPE: PRT
<213> ORGANISM: Homo sapiens

<400> SEQUENCE: 112

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
```

-continued

```
                195                 200                 205
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 113
<211> LENGTH: 326
<212> TYPE: PRT
<213> ORGANISM: Homo sapiens

<400> SEQUENCE: 113

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

-continued

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 114
<211> LENGTH: 329
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Ser
1               5                   10                  15

Thr Ser Gly Gly Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
        50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Lys Thr His Thr Cys Pro Pro Cys Pro
                100                 105                 110

Ala Pro Glu Phe Glu Gly Gly Pro Ser Val Phe Leu Phe Pro Pro Lys
            115                 120                 125

Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Ser Ile Glu Lys Thr Ile Ser Lys Ala Lys Gly Gln
        210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285
```

-continued

```
Tyr Ser Lys Leu Thr Val Asp Lys Ser Arg Trp Gln Gln Gly Asn Val
    290             295             300

Phe Ser Cys Ser Val Met His Glu Ala Leu His Asn His Tyr Thr Gln
305             310             315             320

Lys Ser Leu Ser Leu Ser Pro Gly Lys
            325

<210> SEQ ID NO 115
<211> LENGTH: 106
<212> TYPE: PRT
<213> ORGANISM: Homo sapiens

<400> SEQUENCE: 115

Gly Gln Pro Lys Ala Ala Pro Ser Val Thr Leu Phe Pro Pro Ser Ser
1               5               10              15

Glu Glu Leu Gln Ala Asn Lys Ala Thr Leu Val Cys Leu Ile Ser Asp
            20              25              30

Phe Tyr Pro Gly Ala Val Thr Val Ala Trp Lys Ala Asp Ser Ser Pro
        35              40              45

Val Lys Ala Gly Val Glu Thr Thr Thr Pro Ser Lys Gln Ser Asn Asn
    50              55              60

Lys Tyr Ala Ala Ser Ser Tyr Leu Ser Leu Thr Pro Glu Gln Trp Lys
65              70              75              80

Ser His Lys Ser Tyr Ser Cys Gln Val Thr His Glu Gly Ser Thr Val
            85              90              95

Glu Lys Thr Val Ala Pro Thr Glu Cys Ser
            100             105

<210> SEQ ID NO 116
<211> LENGTH: 451
<212> TYPE: PRT
<213> ORGANISM: Homo sapiens

<400> SEQUENCE: 116

Glu Val Gln Leu Val Glu Ser Gly Gly Gly Leu Val Gln Pro Gly Arg
1               5               10              15

Ser Leu Arg Leu Ser Cys Ala Ala Ser Gly Phe Thr Phe Asp Asp Tyr
            20              25              30

Ala Met His Trp Val Arg Gln Ala Pro Gly Lys Gly Leu Glu Trp Val
        35              40              45

Ser Gly Ile Ser Trp Asn Ser Asn Ser Ile Gly Tyr Ala Asp Ser Val
    50              55              60

Arg Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Leu Tyr Tyr Cys
            85              90              95

Ala Lys Asp Met Gly Trp Glu Leu Leu Lys Thr Ser Tyr Tyr Gly Met
            100             105             110

Asp Val Trp Gly Gln Gly Thr Thr Val Thr Val Ser Ser Ala Ser Thr
        115             120             125

Lys Gly Pro Ser Val Phe Pro Leu Ala Pro Cys Ser Arg Ser Thr Ser
    130             135             140

Glu Ser Thr Ala Ala Leu Gly Cys Leu Val Lys Asp Tyr Phe Pro Glu
145             150             155             160

Pro Val Thr Val Ser Trp Asn Ser Gly Ala Leu Thr Ser Gly Val His
            165             170             175
```

-continued

```
Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Glu
            210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
            290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 117
<211> LENGTH: 451
<212> TYPE: PRT
<213> ORGANISM: Homo sapiens

<400> SEQUENCE: 117

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Leu Ala Pro Gly Lys Gly Leu Glu Trp Val
            35                  40                  45

Ser Gly Ile Ser Trp Asn Ser Gly Ser Ile Gly Tyr Ala Asp Ser Val
            50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
```

```
                    85                   90                   95

Ala Lys Asp Met Gly Trp Ser Leu Leu Lys Thr Asn Tyr Tyr Gly Met
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
            195                 200                 205

Asn Val Asp His Lys Pro Ser Asn Thr Lys Val Asp Lys Thr Val Glu
        210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
            275                 280                 285

His Asn Ala Lys Thr Lys Pro Arg Glu Glu Gln Phe Asn Ser Thr Phe
        290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 118
<211> LENGTH: 447
<212> TYPE: PRT
<213> ORGANISM: Homo sapiens

<400> SEQUENCE: 118
```

-continued

```
Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Leu Ile Trp Gly
            100                 105                 110

Gln Gly Thr Met Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

-continued

```
            420              425              430

His Asn His Tyr Thr Gln Lys Ser Leu Ser Leu Ser Pro Gly Lys
        435              440              445

<210> SEQ ID NO 119
<211> LENGTH: 447
<212> TYPE: PRT
<213> ORGANISM: Homo sapiens

<400> SEQUENCE: 119

Gln Val Gln Leu Val Gln Ser Gly Ala Glu Val Lys Lys Ser Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Met Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Ile Ala Tyr
65                  70                  75                  80

Met Glu Leu Ser Ser Leu Arg Ser Glu Asp Thr Ala Val Tyr Tyr Cys
                85                  90                  95

Ala Ser Asp Gly Ala Val Ala Ala Tyr Asp Ala Phe Leu Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350
```

-continued

```
Pro Ser Arg Glu Glu Met Thr Lys Asn Gln Val Ser Leu Thr Cys Leu
        355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Met Leu Asp Ser
385             390             395             400

Asp Gly Ser Phe Phe Leu Tyr Ser Lys Leu Thr Val Asp Lys Ser Arg
            405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys
        435             440             445
```